US012691160B2

(12) United States Patent
Park et al.

(10) Patent No.:     US 12,691,160 B2
(45) Date of Patent:          Jul. 28, 2026

(54) ENGINEERED FIBROBLAST GROWTH FACTOR 1 VARIANTS WITH INCREASED PROTEOLYTIC STABILITY

(71) Applicant: The Board of Trustees of the Leland Stanford Junior University, Stanford, CA (US)

(72) Inventors: Sung Jin Park, Stanford, CA (US); Jennifer R. Cochran, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 905 days.

(21) Appl. No.: 17/283,794

(22) PCT Filed: Oct. 9, 2019

(86) PCT No.: PCT/US2019/055448
§ 371 (c)(1),
(2) Date: Apr. 8, 2021

(87) PCT Pub. No.: WO2020/076987
PCT Pub. Date: Apr. 16, 2020

(65)         Prior Publication Data
US 2022/0249611 A1      Aug. 11, 2022

Related U.S. Application Data

(60) Provisional application No. 62/743,414, filed on Oct. 9, 2018.

(51) Int. Cl.
| | |
|---|---|
| *A61K 38/18* | (2006.01) |
| *A61K 47/00* | (2006.01) |
| *A61K 51/02* | (2006.01) |
| *A61P 27/00* | (2006.01) |
| *A61P 35/00* | (2006.01) |
| *C12N 15/01* | (2006.01) |

(52) U.S. Cl.
CPC .......... *A61K 38/1825* (2013.01); *A61K 47/00* (2013.01); *A61K 51/02* (2013.01); *A61P 27/00* (2018.01); *A61P 35/00* (2018.01); *C12N 15/01* (2013.01)

(58) Field of Classification Search
None
See application file for complete search history.

(56)         References Cited

U.S. PATENT DOCUMENTS

| | | | |
|---|---|---|---|
| 5,707,624 A | 1/1998 | Nickoloff et al. | |
| 5,997,868 A | 12/1999 | Goldberg et al. | |
| 7,179,786 B2 | 2/2007 | Gherardi et al. | |
| 7,790,682 B1 | 9/2010 | Blaber et al. | |
| 9,290,557 B2 * | 3/2016 | Ling .................. | A61K 38/1825 |
| 9,556,248 B2 | 1/2017 | Cochran et al. | |
| 2003/0036506 A1 | 2/2003 | Kranz et al. | |
| 2009/0215686 A1 | 8/2009 | Xu et al. | |
| 2013/0171068 A1 | 7/2013 | Cochran et al. | |
| 2017/0305985 A1 | 10/2017 | Cochran et al. | |
| 2018/0228869 A1 | 8/2018 | Evans et al. | |
| 2022/0023385 A1 | 1/2022 | Cochran et al. | |
| 2022/0033453 A1 | 2/2022 | Cochran et al. | |
| 2022/0184181 A1 | 6/2022 | Cochran et al. | |

FOREIGN PATENT DOCUMENTS

| | | |
|---|---|---|
| JP | 2010-528645 A | 8/2010 |
| WO | WO2002/088354 | 11/2002 |
| WO | 2008/149143 A2 | 12/2008 |
| WO | WO 2012/064658 A1 | 5/2012 |
| WO | WO 2013/090911 A1 | 6/2013 |
| WO | WO 2013/157973 A1 | 10/2013 |
| WO | WO 2017/044743 A1 | 3/2017 |
| WO | WO 2017/075260 A1 | 5/2017 |
| WO | WO 2018/018010 A1 | 1/2018 |

OTHER PUBLICATIONS

Olsen et al. (J. Biol. Chem. 278(36: 34226-34236, 2003).*
Seddon et al. Biochem. 35: 731-736, 1995.*
Boder, E T, and K D Wittrup. "Yeast surface display for screening combinatorial polypeptide libraries." Nature biotechnology vol. 15,6 (1997): 553-7. doi:10.1038/nbt0697-553.
Businesswire. CVBT Comments That Imaging Modalities Being Developed by Philips Medical Systems Have Direct Application to the Diagnosis and Treatment of Diseases CVBT Is Targeting with Cardio Vascu-Grow(TM). Feb. 24, 2006; https://www.businesswire.com/news/home/20060224005280/en/CVBT-Comments-Imaging-Modalities-Developed-Philips-Medical; p. 1 of 2, First Paragraph.
Chae, Young Kwang et al. "Inhibition of the fibroblast growth factor receptor (FGFR) pathway: the current landscape and barriers to clinical application." Oncotarget vol. 8,9 (2017): 16052-16074. doi:10.18632/oncotarget.14109.
Eveleth, David D et al. "An Engineered Human Fibroblast Growth Factor-1 Derivative, TTHX1114, Ameliorates Short-term Corneal Nitrogen Mustard Injury in Rabbit Organ Cultures." Investigative ophthalmology & visual science vol. 59,11 (2018): 4720-4730. doi:10.1167/iovs.18-24568.

(Continued)

*Primary Examiner* — Christine J Saoud
(74) *Attorney, Agent, or Firm* — Christina A. MacDougall; Xiaoqian Li; Morgan, Lewis & Bockius, LLP

(57)         ABSTRACT

The present invention provides methods of screening for proteolytically stable growth factor variants, including, for example variants of human fibroblast growth factor 1 (FGF1) The present invention also provides for FGF1 variants comprising at least one amino acid substitution, an amino acid deletion, an amino acid addition and combinations thereof, wherein the resulting FGF1 variant exhibits increased proteolytic stability as compared to wild-type FGF1, as well as related uses.

9 Claims, 37 Drawing Sheets
(16 of 37 Drawing Sheet(s) Filed in Color)
Specification includes a Sequence Listing.

(56) References Cited

OTHER PUBLICATIONS

Grant DS, Kleinman HK, Goldberg ID, Bhargava MM, Nickoloff BJ, Kinsella JL, Polverini P, Rosen EM. Scatter factor induces blood vessel formation in vivo. Proc Natl Acad Sci U S A. Mar. 1, 1993;90(5):1937-41. doi: 10.1073/pnas.90.5.1937. PMID: 7680481; PMCID: PMC45995.

Liu, L et al. "An optimised protocol for the production of autologous serum eyedrops." Graefe's archive for clinical and experimental ophthalmology = Albrecht von Graefes Archiv fur klinische und experimentelle Ophthalmologie vol. 243,7 (2005): 706-14. doi:10.1007/s00417-004-1106-5.

Ljubimov, Alexander V, and Mehrnoosh Saghizadeh. "Progress in corneal wound healing." Progress in retinal and eye research vol. 49 (2015): 17-45. doi:10.1016/j.preteyeres.2015.07.002.

López-Plandolit, Silvia et al. "Plasma rich in growth factors as a therapeutic agent for persistent corneal epithelial defects." Cornea vol. 29,8 (2010): 843-8. doi:10.1097/ICO.0b013e3181a81820.

Mitchell, Aaron C et al. "Engineering growth factors for regenerative medicine applications." Acta biomaterialia vol. 30 (2016): 1-12. doi:10.1016/j.actbio.2015.11.007.

Protein Data Bank in Europe. EMBL-EBI. Crystal Structure of L26A/D28N Mutant of Human Acidic Fibroblast Growth Factor. 2012; p. 1 of 3.

Zakrzewska, Malgorzata et al. "Highly stable mutants of human fibroblast growth factor-1 exhibit prolonged biological action." Journal of molecular biology vol. 352,4 (2005): 860-75. doi:10.1016/j.jmb.2005.07.066.

Cherf, Gerald M, and Jennifer R Cochran. "Applications of Yeast Surface Display for Protein Engineering." Methods in molecular biology (Clifton, N.J.) vol. 1319 (2015): 155-75. doi:10.1007/978-1-4939-2748-7_8.

Zakrzewska, Malgorzata et al. "FGF-1: from biology through engineering to potential medical applications." Critical reviews in clinical laboratory sciences vol. 45,1 (2008): 91-135. doi:10.1080/10408360701713120.

Andrae, J., et al. "Role of platelet-derived growth factors in physiology and medicine." Genes Dev. 1276-1312 (2008).

Anitua, E., et al. "Delivering growth factors for therapeutics." Trends Pharmacol. Sci. 29, 37-41 (2008).

Bader et al., "Leukemia Inhibitory Factor Modulates Cardiogenesis in Embryoid Bodies in Opposite Fashions", Institute of Biochemistry, pp. 787-794, 2000.

Backer et al. "Molecular imaging of VEGF receptors in angiogenic vasculature with single-chain VEGF-based probes" (2006) Nat. Med. 13(4):504-509.

Beenken, A et al. "The FGF family: biology, pathophysiology and therapy." Nat Rev Drug Discov. 8, 235-253 (2009).

Belch, J. et al. "Effect of fibroblast growth factor NVIFGF on amputation and death: A randomised placebo-controlled trial of gene therapy in critical limb ischaemia." Lancet 377, 1929-1937 (2011).

Böttger, R., et al. "Differential stability of therapeutic peptides with different proteolytic cleavage sites in blood, plasma and serum." PLoS One 12, 1-15 (2017).

Breitling, J. et al., "M. N-Linked Protein Glycosylation in the Endoplasmic Reticulum." Cold Spring Harb. Perspect. Biol. (2013). doi: 10. I 101/cshperspect.a013359.

Buchtova, M. et al. "Instability restricts signaling of multiple fibroblast growth factors." Cell. Mal. Life Sci. 72, 2445-2459 (2015).

Burgess et al. "Fully Human Monoclonal Antibodies to Hepatocyte Growth Factor with Therapeutic Potential against Hepatocyte Growth Factor/c-Met-Dependent Human Tumors" (2006) Cancer Res. 66: 1721-1729.

Cao et al. "Neutralizing monoclonal antibodies to hepatocyte growth factor / scatter factor (HGF/SF) display antitumor activity in animal models" (2001) Proc. Natl. Acad. Sci. USA 98: 7443-7448.

Carmeliet, P. "Fibroblast growth factor-I stimulates branching and survival of myocardial arteries: A goal for therapeutic angiogenesis?" Circ. Res. 87, 176-178 (2000).

Carmeliet, P. "VEGF as a key mediator of angiogenesis in cancer." Oncology 69, 4-10 (2005).

Chaffee et al. "IgG antibody response to polyethylene glycol-modified adenosine deaminase with adenosine deaminase deficiency" J. Clin. Invest. 89; 1643-1651 (1992).

Cochran, J. R., et al. "Improved mutants from directed evolution are biased to orthologous substitutions." Protein Eng. Des. Sel. 19, 245-253 (2006).

Comerota, A J. et al. "Naked plasmid DNA encoding fibroblast growth factor type I for the treatment of end-stage unreconstructible lower extremity ischemia: Preliminary results of a phase I trial." J Vase. Surg. 35, 930-936 (2002).

Cook, A. L., et al., "Purification and analysis of proteinase-resistant mutants of recombinant platelet-derived growth factor-BB exhibiting improved biological activity." Biochem. J. 281, 57-65 (1992).

Copeland, R. A. et al., "The structure of human acidic fibroblast growth factor and its interaction with heparin." Arch. Biochem. Biophys. 289, 53-61 (1991).

Draghia-Akli, R. et al. "Myogenic expression of an injectable protease-resistant growth hormone-releasing hormone augments long-term growth in pigs." Nat. Biotechnol. 17, 1179-1183 (1999).

Dubey, V. K., et al. "Spackling the Crack: Stabilizing Human Fibroblast Growth Factor-I by Targeting the N and C terminus□-Strand Interactions." J Mal. Biol. 371, 256-268 (2007).

Ericsson, U. B., et al. "Thermofluor-based high-throughput stability optimization of proteins for structural studies." Anal. Biochem. 357, 289-298 (2006).

Eswarakumar, V. P., Lax, I. & Schlessinger, J. "Cellular signaling by fibroblast growth factor receptors." Cytokine Growth Factor Rev. 16, 139-149 (2005).

Feldhaus et al., "Flow Cytometric Isolation of Human Antibodies from a Nonimmune *Saccharomyces cerevisiae* Surface Display Library", Dept. Chem. Engineering., (2003).

Gai, S.A., et al, "Yeast surface display for protein engineering and characterization," Current Opinion in Structural Biology, 17:4 pp. 467-473 (2007).

Gherardi et al. "Structural basis of hepatocyte growth factor/scatter factor and MET signalling." PNAS, 103(11): 4046-4051 (2006).

Gosalia, D. N., et al. "High Throughput Substrate Specificity Profiling of Serine and Cysteine Proteases Using Solution-phase Fluorogenic Peptide Microarrays." Mal. Cell. Proteomics 4, 626-636 (2005).

Hervio, L. S. et al. "Negative selectivity and the evolution of protease cascades: the specificity of plasmin for peptide and protein substrates." Chem. Biol. 7, 443-453 (2000).

Holler et al., "Fas triggers an alternative, caspase-8-independent cell death pathway using the kinase RIP as effect or molecule", Nature America Inc., pp. 489-495, 2000.

Jones et al. "Developing therapeutic proteins by engineering ligand-receptor interactions," Trends in Biotechnology, 26:9, pp. 498-505 (2008).

Jones et al. "Engineered Hepatocyte Growth Factor Fragments Function as MET Receptor Antagonists by Inhibiting Ligand-Induced Dimerization," AIChE Annual Meeting (2010).

Jones, D. S., Tsai, P.-C. & Cochran, J. R. "Engineering hepatocyte growth factor fragments with high stability and activity as Met receptor agonists and antagonists." Proc. Natl. Acad Sci. 108, 13035-13040 (2011).

Jones D.S.,2nd, et al. "Engineering hepatocyte growth factor fragments with high stability and activity as met receptor agonists and antagonists." Proc Natl Acad Sci US A. 2011; 108(32): 13035-13040.

Kapur, S. et al., "Engineered ligand-based VEGFR antagonists with increased receptor binding affinity more effectively inhibit angiogenesis." Bioeng. Transl. Med. 2, 81-91 (2017).

Katre et al. "Chemical modification of recombinant interleukin 2 by polyethylene glycol increases its potency in the murine Meth A sarcoma model" Proc. Natl. Acad. Sci. USA. 84; 1487-1491 (1987).

Kay EP, et al. "TGF-J3s stimulate cell proliferation via an autocrine production of FGF-2 in corneal stromal fibroblasts." Curr Eye Res. 1998; 17(3):286-293.

(56)　　　　　References Cited

OTHER PUBLICATIONS

Kitamura et al. "Polyethlene Glycol Modification of the Monoclonal Antibody A7 enhances its tumor localization" Biochem. Biophys. Res. Commun. 28: 1397-1394 (1990).

Kitamura, M. et al., "Randomized Placebo-Controlled and Controlled Non-Inferiority Phase III Trials Comparing Trafermin, a Recombinant Human Fibroblast Growth Factor 2, and Enamel Matrix Derivative in Periodontal Regeneration in Intrabony Defects." J. Bone. Miner. Res. 31, 806-814 (2016).

Knights, V., et al. "De-regulated FGF receptors as therapeutic targets in cancer." Pharmacol. Ther. 125, 105-117 (2010).

Kobielak, A. et al., Protease Resistant Variants of FGF1 with Prolonged Biological Activity. Protein Pept. Lett. 434-443 (2014).

Korc, M., et al. "The role of fibroblast growth factors in tumor growth." Curr. Cancer Drug Targets 9, 639-51 (2009).

Kowalski, J.M., et al. "Secretion Efficiency in *Saccharomyces cerevisiae* of Bovine Pancreatic Trypsin Inhibitor Mutants Lacking Disulfide Bonds Is Correlated with Thermodynamic Stability." Biochemistry 37, 1264-1273 (1998).

Lan Y, et al. "Kinetics and function of mesenchymal stem cells in corneal InjuryMSCs in corneal injury." Invest Ophthalmol Vis Sci. 2012;53(7):3638-3644.

Lavinder, J. J., et al. "High-throughput thermal scanning: a general, rapid dye-binding thermal shift screen for protein engineering." J Am Chem Soc. 131, 3794-3795 (2009).

Lee, J., et al. "A Logical OR Redundancy within the Asx-Pro-Asx-Gly Type I ??-Turn Motif" J Mal. Biol. 377, 1251-1264 (2008).

Lee, J. et al., "Increased Functional Half-life of Fibroblast Growth Factor-1 by Recovering a Vestigial Disulfide Bond." Proteins and Protoeconomics 1, 37-42 (2010).

Liu C.J., et al. "An engineered dimeric fragment of hepatocyte growth factor is a potent c-MET agonist." FEES Lett. 2014;588(24):4831-4837.

Mason, I. "Initiation to end point: The multiple roles of fibroblast growth factors in neural development." Nat. Rev. Neurosci. 8, 583-596 (2007).

Mittal S.K., et al. "Restoration of corneal transparency by mesenchymal stem cells." Stem cell reports. 2016;7(4):583-590.

Miyagi H, et al. "The role of hepatocyte growth factor in corneal wound healing." Exp Eye Res. 2017.

Mori, S. et al. "A Dominant-Negative FGFI Mutant (the R50E Mutant) Suppresses Tumorigenesis and Angiogenesis." PLoS One 8, (2013).

Motomura, K et al., "An FGF1-FGF2 chimeric growth factor exhibits universal FGF receptor specificity, enhanced stability and augmented activity useful for epithelial proliferation and radioprotection." Biochem. Biophys. Acta-Gen. Subj. 1780, 1432-1440 (2008).

Nikol, S. et al. "Therapeutic angiogenesis with intramuscular NVIFGF improves amputation-free survival in patients with critical limb ischemia." Mal. Ther. 16, 972-978 (2008).

Papo, N., et al. "Antagonistic VEGF variants engineered to simultaneously bind to and inhibit VEGFR2 and v3 integrin." Proc. Natl. Acad. Sci. 108, 14067-14072 (2011).

Park, S. et al. "Limitations of yeast surface display in engineering proteins of high thermostability." Protein Eng. Des. Se!. 19, 211-217 (2006).

Pastor J.C., et al. "Epidermal growth factor and corneal wound healing: A multicenter study." Cornea. 1992;11(4):311-314.

Presta, M. et al. "Fibroblast growth factor/fibroblast growth factor receptor system in angiogenesis." Cytokine Growth Factor Rev. 16, 159-178 (2005).

Rafii M, et al. "Identifying and filling the unmet need." Review of Ophthalmology. 2015.

Rogers GFC, et al. "Synergistic corneal wound healing effects of human mesenchymal stem cell secreted factors and hyaluronic acid-based viscoelastic gel." Invest Ophthalmol Vis Sci. 2018;59(9):2989-2989.

Rosengart, T. K., et al. "Heparin protects heparin-binding growth factor-I from proteolytic inactivation in vitro." Biochem. Biophys. Res. Commun. 152, 432-440 (1988).

Schumacher, B., et al. "Induction of neoangiogenesis in ischemic myocardium by human growth factors: first clinical results of a new treatment of coronary heart disease." Circulation 97, 645-650 (1998).

Sharrocks, AD. "Cell Cycle: Sustained ERK Signalling Represses the Inhibitors." 16, 540-542.

Steele A.N., et al. "A novel protein-engineered hepatocyte growth factor analog released via a shear-thinning injectable hydrogel enhances post-infarction ventricular function." Biotechnol Bioeng. 2017; I 14(10):2379-2389.

Suarez S.L. et al. "Degradable acetalated dextran microparticles for tunable release of an engineered hepatocyte growth factor fragment." ACS biomaterials science & engineering. 2016;2(2): 197-204.

Teven, C. M., et al. "Fibroblast growth factor (FGF) signaling in development and skeletal diseases." Genes Dis. 1, 199-213 (2014).

Tripathi RC, et al. "Fibroblast growth factor in the eye and prospects for its therapeutic use." Drug Dev Res. 1990; 19(3):225-237.

Turner, N., et al. "Fibroblast growth factor signalling: From development to cancer." Nat Rev. Cancer 10, 116-129 (2010).

VanAntwerp, et al., "Fine Affinity Discrimination by Yeast Surface Display and Flow Cytometry", Biotechnol pp. 31-37, 2000.

Weaver-Feldhaus et al., "Directed evolution for the development of conformation-specific affinity reagents using yeast display," Protein Engineering Design and Selection Sep. 26, 2005 18(11): 527-536.

Weber, J. D., et al. "Sustained activation of extracellular-signal-regulated kinase I (ERK.I) is required for the continued expression of cyclin DI in G I phase." Biochem. J 68, 61-68 (1997).

Werb, Z., et al. "Matrix-degrading proteases and angiogenesis during development and tumor formation." Apmis 107, 11-18 (1997).

Yamaji, S. et al. "A Novel Fibroblast Growth Factor-I ( FGFI ) Mutant that Acts as an FGF Antagonist." PLoS One 5, (2010).

Youles et al. "Engineering the NK1 Fragment of Hepatocyte Growth Factor/Scatter Factor as a MET Receptor Antagonist," J. Mol. Biol., 377:3, pp. 616-622 (2008).

Yun, Y. et al. "Fibroblast Growth Factors: Biology, Function, and Application for Tissue Regeneration." J Tissue Eng. (2010). doi:10.4061/2010/218142.

Zakrzewska, M. et al. "Increased protein stability of FGF1 can compensate for its reduced affinity for heparin." J. Biol. Chem. 284, 25388-25403 (2009).

Zhang, J., et al. "Therapeutic uses of FGFs." Semin. Cell Dev. Biol. 53, 144-154 (2016).

Shane, Thomas, International Search Report and Written Opinion for International Patent Application No. PCT/US2019/055448, 14 pages, published Jun. 4, 2020.

Young, Lee, International Search Report and Written Opinion for International Patent Application No. PCT/US2020/030116, 9 pages, published Nov. 5, 2020.

Brero, Alessandro, International Search Report and Written Opinion for International Patent Application No. PCT/US2011/029271, 17 pages, published Apr. 19, 2012.

Shane, Thomas, International Search Report and Written Opinion for International Patent Application No. PCT/US2019/055453, 9 pages, published Apr. 16, 2020.

* cited by examiner

1.5 µM plasmin
12 hour incubation

1.25 µM plasmin
24 hour incubation 36 hour incubation

| | 1 | 2 | 3 | AVG |
|---|---|---|---|---|
| FGF1 | 55.2 | 56.3 | 54.4 | 55.30 ± 0.55 |
| L131R | 56.5 | 56.1 | 57.1 | 56.57 ± 0.29 |

NIH3T3 ERK
Phosphorylation 15 hour pulse, α-phosphoERK

Sample #
1 = Untreated
2 = 1 nM FGF1
3 = 1 nM L131R

4 = 1 nM FGF1 + 1 nM L131R
5 = 1 nM FGF1 + 10 nM L131R
6 = 1 nM FGF1 + 100 nM L131R 10 hour pulse NIH3T3 ERK Phosphorylation NIH3T3 ERK phosphorylation (15 min)

SEQUENCE LISTING

<160> NUMBER OF SEQ ID NOS: 15

<210> SEQ ID NO 1
<211> LENGTH: 140
<212> TYPE: PRT
<213> ORGANISM: Artificial Sequence
<220> FEATURE:
<223> OTHER INFORMATION: FGF1 Polypeptide

<400> SEQUENCE: 1

```
Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140
```

<210> SEQ ID NO 2
<211> LENGTH: 14
<212> TYPE: PRT
<213> ORGANISM: Artificial Sequence
<220> FEATURE:
<223> OTHER INFORMATION: Linker amino acid

<400> SEQUENCE: 2

```
Lys Glu Ser Cys Ala Lys Lys Gln Arg Gln His Met Asp Ser
1               5                   10
```

<210> SEQ ID NO 3
<211> LENGTH: 140
<212> TYPE: PRT
<213> ORGANISM: Artificial Sequence
<220> FEATURE:
<223> OTHER INFORMATION: FGF1 variant BS4M1

<400> SEQUENCE: 3

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asn Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Arg Phe Leu Pro Leu Pro Val Ser Ser Asp
    130                 135                 140

<210> SEQ ID NO 4
<211> LENGTH: 140
<212> TYPE: PRT
<213> ORGANISM: Artificial Sequence
<220> FEATURE:
<223> OTHER INFORMATION: FGF1 variant PM2

<400> SEQUENCE: 4

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Pro His Ile Gln Leu Gln Leu Ile Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn Gly Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 5
<211> LENGTH: 140
<212> TYPE: PRT
<213> ORGANISM: Artificial Sequence
<220> FEATURE:

-continued

```
<223> OTHER INFORMATION: FGF1 variant PM3

<400> SEQUENCE: 5

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asn Gly Thr Val Asp
            20                  25                  30

Gly Thr Arg Asp Arg Ser Asp Pro His Ile Gln Leu Gln Leu Ile Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn Gly Tyr Asn Thr
                85                  90                  95

Tyr Ile Ser Lys Lys His Ala Glu Lys Asn Trp Phe Val Gly Leu Lys
                100                 105                 110

Lys Asn Gly Ser Cys Lys Arg Gly Pro Arg Thr His Tyr Gly Gln Lys
            115                 120                 125

Ala Ile Arg Phe Leu Pro Leu Pro Val Ser Ser Asp
    130                 135                 140

<210> SEQ ID NO 6
<211> LENGTH: 140
<212> TYPE: PRT
<213> ORGANISM: Artificial Sequence
<220> FEATURE:
<223> OTHER INFORMATION: FGF1 variant polypeptide

<400> SEQUENCE: 6

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
                100                 105                 110

Lys Asn Gly Ser Cys Lys Arg Gly Pro Arg Thr His Tyr Gly Gln Lys
            115                 120                 125

Ala Ile Arg Phe Leu Pro Leu Pro Val Ser Ser Asp
    130                 135                 140

<210> SEQ ID NO 7
<211> LENGTH: 140
<212> TYPE: PRT
<213> ORGANISM: Artificial Sequence
<220> FEATURE:
<223> OTHER INFORMATION: FGF1 variant polypeptide

<400> SEQUENCE: 7

Phe Asn Leu Pro Pro Gly Asn Tyr Lys Lys Pro Lys Leu Leu Tyr Cys
```

```
1                  5                    10                   15

Ser Asn Gly Gly His Phe Leu Arg Ile Leu Pro Asp Gly Thr Val Asp
                20                  25                  30

Gly Thr Arg Asp Arg Ser Asp Gln His Ile Gln Leu Gln Leu Ser Ala
                35                  40                  45

Glu Ser Val Gly Glu Val Tyr Ile Lys Ser Thr Glu Thr Gly Gln Tyr
            50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
                100                 105                 110

Lys Asn Gly Ser Cys Lys Arg Gly Pro Arg Thr His Tyr Gly Gln Lys
            115                 120                 125

Ala Ile Lys Phe Leu Pro Leu Pro Val Ser Ser Asp
            130                 135                 140

<210> SEQ ID NO 8
<211> LENGTH: 330
<212> TYPE: PRT
<213> ORGANISM: Artificial Sequence
<220> FEATURE:
<223> OTHER INFORMATION: Immunoglobulin IgG1

<400> SEQUENCE: 8

Ala Ser Thr Lys Gly Pro Ser Val Phe Pro Leu Ala Pro Ser Ser Lys
1                  5                    10                   15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
```

-continued

```
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 326
<212> TYPE: PRT
<213> ORGANISM: Artificial Sequence
<220> FEATURE:
<223> OTHER INFORMATION: Immunoglobulin IgG2

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
```

-continued

```
                260                 265                 270
Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325
```

```
<210> SEQ ID NO 10
<211> LENGTH: 377
<212> TYPE: PRT
<213> ORGANISM: Artificial Sequence
<220> FEATURE:
<223> OTHER INFORMATION: Immunoglobulin IgG3

<400> SEQUENCE: 10

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
            130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
            210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
```

-continued

```
              290                 295                 300
Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 11
<211> LENGTH: 327
<212> TYPE: PRT
<213> ORGANISM: Artificial Sequence
<220> FEATURE:
<223> OTHER INFORMATION: Immunoglobulin IgG4

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
```

-continued

```
                275                    280                    285

Arg Leu Thr Val Asp Lys Ser Arg Trp Gln Glu Gly Asn Val Phe Ser
        290                    295                    300

Cys Ser Val Met His Glu Ala Leu His Asn His Tyr Thr Gln Lys Ser
305                    310                    315                    320

Leu Ser Leu Ser Leu Gly Lys
                    325

<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

His Thr Thr Ser
1

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

Arg Thr Thr Thr Ser
1                  5

<210> SEQ ID NO 14

<400> SEQUENCE: 14

000

<210> SEQ ID NO 15
<211> LENGTH: 4
<212> TYPE: PRT
<213> ORGANISM: Artificial Sequence
<220> FEATURE:
<223> OTHER INFORMATION: stability of FGF1

<400> SEQUENCE: 15

Asx Pro Asx Gly
1
```

ENGINEERED FIBROBLAST GROWTH FACTOR 1 VARIANTS WITH INCREASED PROTEOLYTIC STABILITY

CROSS REFERENCE TO RELATED APPLICATION

The present application is a National Phase entry of International Patent Application No. PCT/US2019/055448, filed on Oct. 9, 2019, which claims priority to U.S. Provisional Patent Application No. 62/743,414, filed on Oct. 9, 2018, entitled "Engineered Fibroblast Growth Factor Variants As Receptor Antagonists", which are hereby incorporated by reference in their entirety.

FIELD OF THE INVENTION

The invention pertains to the field of polypeptide variants, in particular variants of fibroblast growth factor (FGF).

REFERENCE TO SEQUENCE LISTING

This invention incorporated by reference the Sequence Listing text copy submitted herewith, which was created on Aug. 27, 2024, titled "52400513_068597-5040-US_Revised_Sequence_Listing_ST25.txt" which is 20,983 bytes in size.

BACKGROUND OF THE INVENTION

Human growth factors play a pivotal role in orchestrating many complex processes, such as wound healing, tissue regeneration, angiogenesis, and tumor formation[1-4]. Thus, there is immense interest in utilizing growth factors as protein therapeutics for accelerating wound healing and regenerative processes, or inhibiting cancer growth and angiogenesis in a variety of diseases and conditions[5-7]. However, even though numerous recombinant growth factors have been developed as therapeutics, only a few candidates have been effective enough to receive clinical approval[8,9]. This is due, in large part, to the short effective half-life of growth factors in vivo, stemming from their generally poor stability and fast blood clearance[5,10]. Therapeutic growth factors must remain active in the wound area for an extended period to be efficacious. However, growth factors can become denatured or degraded upon exposure to physiological temperatures and proteases[11,12] Resistance to protease-mediated degradation can be particularly important, as proteases such as plasmin and metalloproteinases are especially active in tissue remodeling[13].

Various growth factors have previously been modified to improve their thermal and proteolytic stability, and this has been shown to enhance their biological activity in both in vitro functional assays and in vivo experiments[14-17]. For example, a growth hormone-releasing hormone (GHRH) designed to be more resistant to serine proteases, oxidation, and dipeptidyl peptidase IV was found to be more potent than wild type GHRH in inducing weight gain in pigs[18]. However, many of these constructs have been rationally designed based on protein-specific hypotheses and tested in a low-throughput manner. Thus, it can be a difficult and slow process to generate new growth factor variants with improved stability. For engineering proteins with increased proteolytic stability, single mutations are often made directly adjacent to the predicted cleavage site, which is based on primary sequence specificity or mass spectroscopy after proteolysis[17,19]. However, this method is far from reliable, as proteolytic stability against a specific protease is multifactorial. First, the activity of a protease in cleaving a specific amino acid sequence is greatly affected by multiple amino acids near the cleavage site. Up to 8 amino acids can determine whether cleavage occurs at a specific site and at what rate cleavage occurs, even if the amino acid directly upstream of the predicted cleavage site (P1) matches the primary specificity of the protease. In a publication by Gosalia et al., they find that even combinatorially varying the two amino acids (P2, P3) upstream of a correct P1 site will drastically affect the proteolytic cleavage rate of a peptide substrate[20]. Second, the proteolytic cleavage of a protein substrate is also determined by the steric accessibility of the cleavage site by the protease's enzymatic binding pocket. Although computational methods have improved for predicting how mutations may affect protein structure, it remains computationally expensive and technically challenging to predict how mutations may change the accessibility of a potential cleavage site by a protease. Thus, there are severe limitations in predicting mutations which would increase proteolytic stability through rational design. The lack of easily adaptable methods for engineering proteolytic stability may partially explain the limited development of proteolytically stable growth factors to date.

The present invention meets this need by providing methods for engineering proteolytically stable growth factors. The present invention also provides proteolytically stable FGF peptide variants generated by the described method, as well as uses of such FGF peptide variants.

BRIEF SUMMARY OF THE INVENTION

The present invention provides a variant of human fibroblast growth factor 1 (FGF1) comprising at least one member selected from an amino acid substitution, an amino acid deletion, an amino acid addition and combinations thereof, wherein the resulting FGF1 variant exhibits increased proteolytic stability as compared to wild-type FGF1 of SEQ ID NO:1.

In some embodiments, the FGF1 variant comprises an amino acid substitution, an amino acid deletion, an amino acid addition and combinations thereof in the β-loop or near the C-terminus.

In some embodiments, the FGF1 variant is a fibroblast growth factor receptor (FGFR) antagonist.

In some embodiments, the FGF1 variant comprises at least one amino acid substitution at position 28, 40, 47, 93 or 131.

In some embodiments, the FGF1 variant comprise at least one amino acid substitution selected from the group consisting of D28N, Q40P, S47I, H93G, L131R, and L131K.

In some embodiments, the FGF1 variant comprises amino acid substitution L131R.

In some embodiments, the FGF1 variant comprises amino acid substitution L131K.

In some embodiments, the FGF1 variant comprises amino acid substitutions D28N and L131R.

In some embodiments, the FGF1 variant comprises amino acid substitutions D28N and L131K.

In some embodiments, the FGF1 variant comprises amino acid substitutions Q40P, S47I, H93G, and L131R.

In some embodiments, the FGF1 variant comprises amino acid substitutions Q40P, S47I, H93G, and L131K.

In some embodiments, the FGF1 variant comprises amino acid substitutions D28N, Q40P, S47I, H93G, and L131R.

In some embodiments, the FGF1 variant comprises amino acid substitutions D28N, Q40P, S47I, H93G, and L131K.

US 12,691,160 B2

3

In some embodiments, the FGF1 variant does not comprise the amino acid substitution L131A.

In some embodiments, the FGF1 variant is conjugated to a member selected from a detectable moiety, a water-soluble polymer, a water-insoluble polymer, a therapeutic moiety, a targeting moiety and a combination thereof.

In some embodiments, the FGF1 variant is conjugated to a detectable moiety selected from a radioisotope, a paramagnet, a fluorophore and combinations thereof.

In some embodiments, the FGF1 variant is a diagnostic imaging agent.

The present invention also provides a pharmaceutical formulation comprising a FGF1 variant according to claim 1, wherein said variant is in combination with a pharmaceutically acceptable carrier. A method of inhibiting or preventing angiogenesis a subject in need thereof, comprising administering a variant according to claim 1 to the subject in need thereof, thereby preventing or inhibiting angiogenesis.

In some embodiments, the subject has cancer.

In some embodiments, the subject is treated to prevent neovascularization in the eye.

The present invention also provides a method of treating cancer in a subject in need of the treatment, the method comprising administering to the subject a therapeutically effective amount of an FGF1 variant as provided herein, thereby treating the cancer.

The present invention also provides a method of reducing a process which is a member selected from tumor progression, angiogenesis, metastasis and combinations thereof in a subject, the method comprising administering to said subject an amount of a variant according to claim 1 sufficient to reduce the process.

In some embodiments, the cancer is a member selected from colorectal, oral, hepatocellular, renal, breast, lung, ovarian, stomach, brain, prostate, and combinations thereof.

The present invention also provides nucleic acids encoding the FGF1 variant polypeptides as described herein.

The present invention also provides isolated cells comprising the nucleic acids encoding the FGF1 variant polypeptides as described herein, and which are capable of expressing the FGF1 variant polypeptides as described herein.

The present invention also provides a method of screening for proteolytically stable growth factor variants, said method comprising:

i. expressing a library of growth factor variants in a yeast display system;

ii. testing the yeast displayed growth factor variants from i) for proper folding by measuring binding activity of the yeast displayed growth factor variants to the relevant growth factor receptor;

iii. incubating the yeast displayed growth factor variants from ii) with at least one protease;

iv. determining the protease cleavage of the yeast displayed growth factor variants from iii) as compared to the protease cleavage of the wild-type growth factor; and v. selecting the variants from iv) that exhibit reduced protease cleavage by and/or increased proteolytic stability to at least one protease as compared to the protease cleavage of the wild-type growth factor by the same protease, wherein said selected growth factor variants are proteolytically stable growth factor variants.

In some embodiments, the at least one protease is a protease capable of cleaving the wild-type growth factor.

In some embodiments, the at least one protease is capable of selectively cleaving the growth factor and which exhibits minimal and/or no non-specific cleavage of the yeast display proteins In some embodiments, the at least one protease is selected from the group consisting of serum, trypsin, chymotrypsin, and plasmin.

In some embodiments, the at least one protease is serum.

In some embodiments, the at least one protease is trypsin.

In some embodiments, the at least one protease is chymotrypsin.

In some embodiments, the at least one protease is plasmin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 Proteolytic stability assay with fetal bovine serum. Yeast cells displaying an FGF1 mutant library were incubated with different concentrations of fetal bovine serum. After washing cells and incubation with 10 nM FGFR1-Fc, cells were stained with fluorescent antibodies for c-myc and the Fc domain of the soluble receptor. Analysis by flow cytometry shows that increasing the concentration of FBS has relatively little effect on the FGF1-specific cleavage signal as well as the FGFR1-Fc binding signal.

FIG. 8A-FIG. 8B FGF1-specific cleavage by chymotrypsin. Yeast cells displaying FGF1 were incubated with different concentrations of trypsin. After washing, cells were stained with fluorescent antibodies for HA and c-myc. Analysis by flow cytometry shows that increasing the concentration of chymotrypsin leads to loss of c-myc signal but not of HA signal, indicating that FGF1-specific cleavage occurs.

FIG. 11 Validation of proteolytic stability assay by differentiation of wild type FGF1 and proteolytically stable PM2. Plasmin enables differentiation between wild type FGF1 and proteolytically stable mutant (PM2) by yeast surface display after 2-day incubation at various plasmin concentrations. This demonstrates the ability of the plasmin-based screen to identify new proteolytically stable mutants.

After a final wash, cells were stained with fluorescent antibodies for expression (α-c-myc) and FGFR1 binding (α-FGFR1-Fc). Fluorescence activated cell sorting (FACS) was used to analyze and gate for cells that exhibited high c-myc signal and high FGFR1-Fc signal. The FACS dot plots are shown for FGF1. The final conditions used for gating and collection of cells for enrichment are noted. The same gate is drawn for all conditions of a given FGF. The percentage of cells that were collected from the total population is shown next to the drawn gates on the dot plots. Bottom Panel: Retain binding to FGFR1-Fc after incubation with 3.75 µM plasmin for 36 hours.

Figure 19:
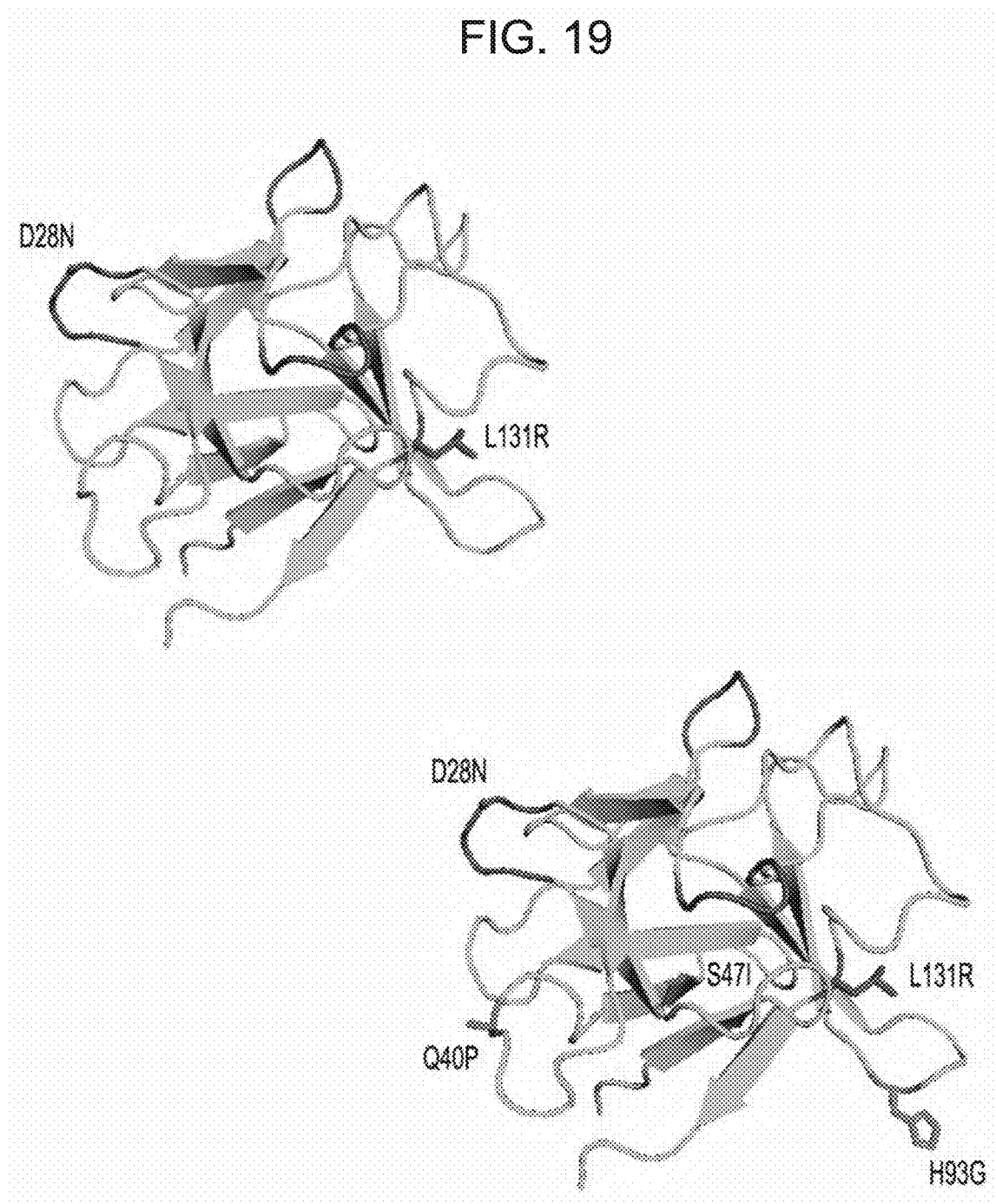

FIG. 19 BS4M1 mutations on FGF1 structure (PDB code 1E0O). Enriched mutations identified by screen for proteolytic stability are highlighted in dark. D28N mutation is located in one of three β-hairpins that stabilize six-stranded β-barrel structure. L131R mutation is located near the C-terminus of the protein, where there is a lack of a stabilizing β-hairpin between the N- and C-termini.

Figures 20A, 20B:
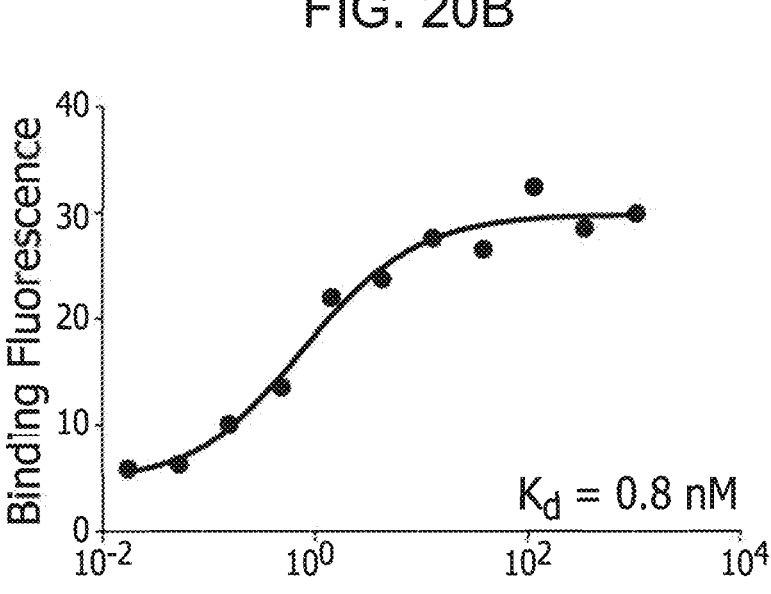

FIG. 20A-FIG. 20B Recombinant expression of soluble wild-type FGF1. (A) Purified wild-type FGF1 was analyzed by non-reduced Coomassie-stained gel (left) and Western blot against FGF1 (right). Two significant bands indicate the presence of FGF1 monomer (19.7 kDa) and dimer (39.4 kDa). (B) Proper folding of FGF1 is confirmed by observing specific binding to yeast-displayed FGFR3 construct.

Figure 21A:
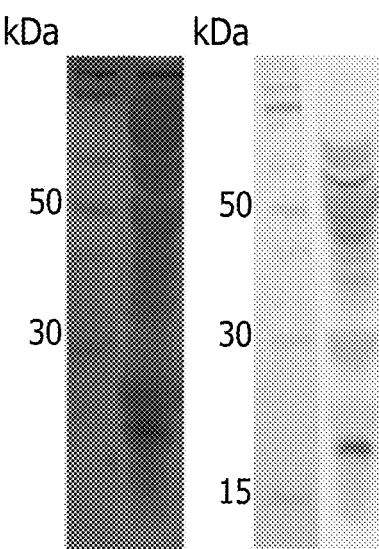
Figure 21B:
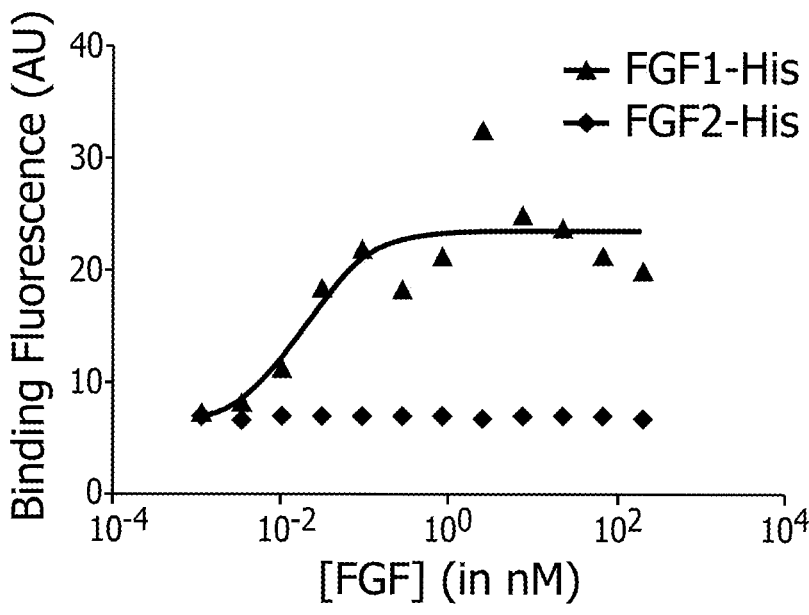

FIG. 21A-FIG. 21B Recombinant expression of FGF2 in pBAD vector. (A) Wild-type FGF2-His expressed in pBAD and purified was analyzed by reduced Coomassie-stained gel (left) and Western blot against FGF2 (right). Both indicate aggregation by the expressed FGF2. (B) FGF2-His expressed in pBAD is unable to bind to yeast-displayed FGFR3 construct.

Figure 22:
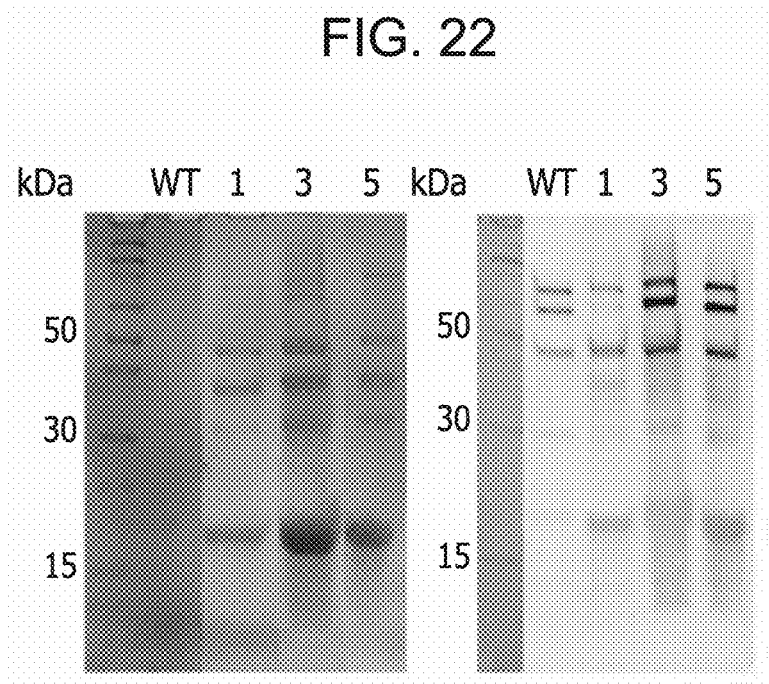

FIG. 22 Recombinant expression of FGF2 in pET28b vector. Wild-type FGF2 and FGF2 mutants (BS5M1, BS5M3, BS5M5) were expressed as fusions to superfolder GFP in the pET28b vector. Wild-type FGF2-His expressed in pBAD and purified was analyzed by reduced Coomassie-stained gel (left) and Western blot against FGF2 (right). Wild type FGF2 is poorly expressed, while the FGF2 mutants shows signs of aggregation and/or oligomerization.

Figure 23:
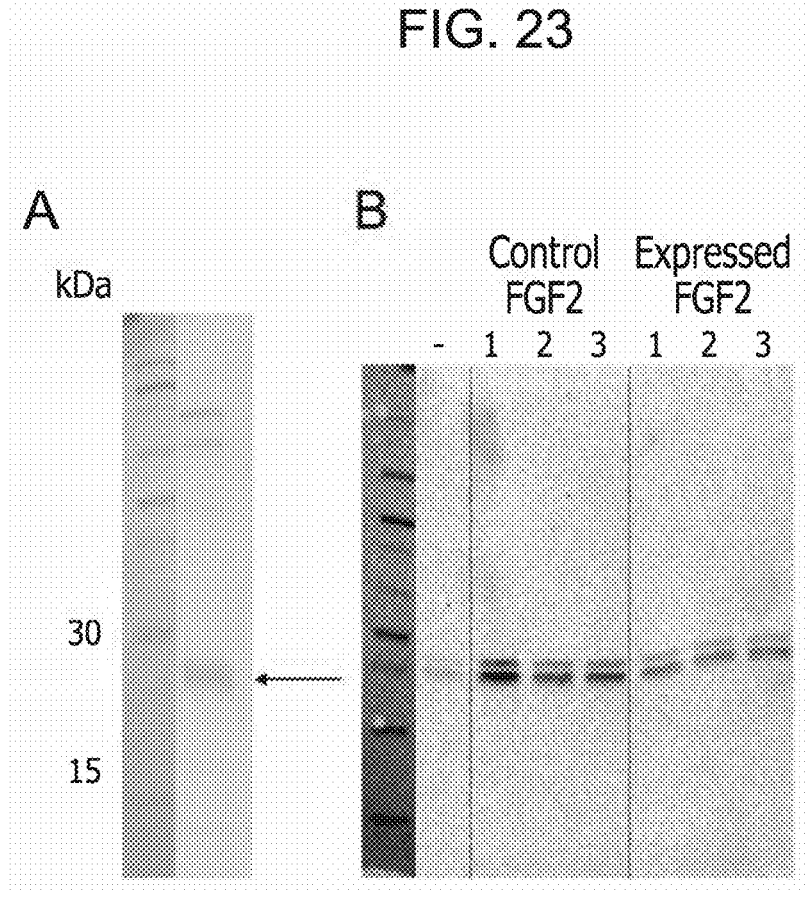

FIG. 23 Recombinant expression of wild-type FGF2 in pET32a vector. (A) FGF2 was expressed as a fusion to thioredoxin in the pET32a vector. After cleavage with TEV and purification by Ni-NTA and size exclusion chromatography, we analyzed the protein by Western blot against FGF2. We confirmed successful purification of FGF2 (19.3 kDa).

Figure 24A:
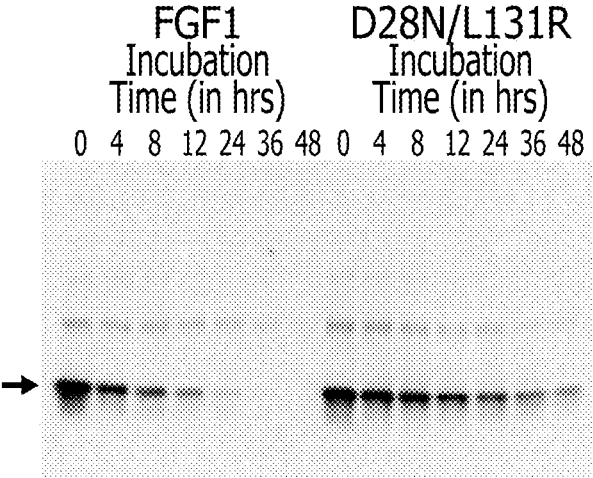
Figure 24B:
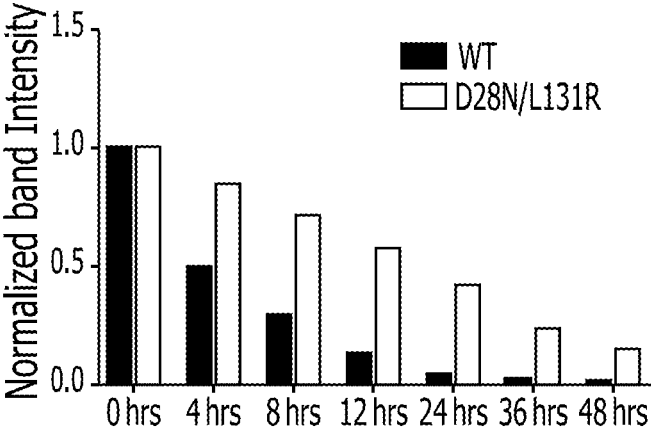

FIG. 24A-FIG. 24B Proteolytic stability assay of FGF1 WT and BS4M1 in plasmin. The FGF1 BS4M1 (D28N/L131R) mutant shows greater proteolytic stability in plasmin as compared to wild-type FGF1. 100 ng of FGF1 was incubated with 600 nM plasmin for various incubation times at 37° C. The incubated samples were run on separate lanes of a Western blot against FGF1 to measure the extent of protein degradation at each time point. The band intensities of the protein bands indicated by the arrow were quantified by image analysis to measure the amount of remaining protein. The band intensities were normalized by the time point t=0 for each protein and plotted.

Figure 25A:
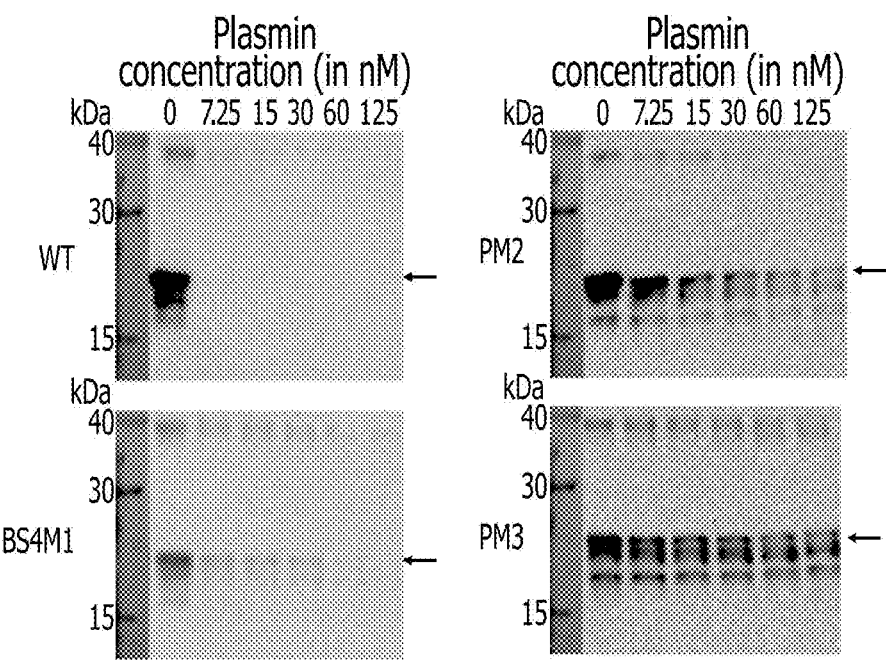
Figure 25B:
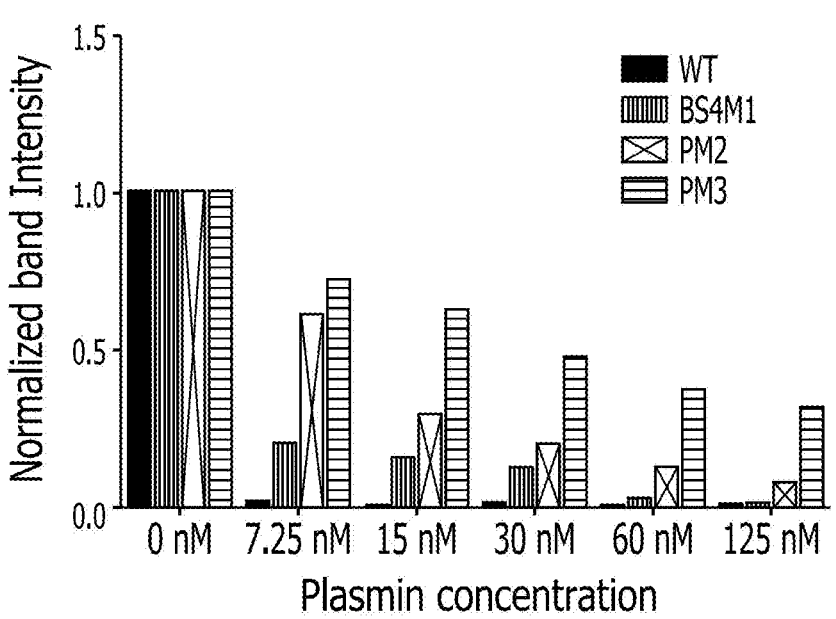

FIG. 25A-FIG. 25B Proteolytic stability assay of FGF1 WT, BS4M1, PM2, and PM3 in plasmin. The mutations from BS4M1 (D28N, L131R) are combined with those from PM2 (Q40P, S47I, H93G) to create PM3. PM3 shows greater proteolytic stability in plasmin as compared to either BS4M1 or PM2. 125 ng of FGF1 was incubated for 48 hours at 37° C. with various concentrations of plasmin. The incubated samples were run on separate lanes of a Western blot against FGF1 to measure the extent of protein degradation at each time point. The band intensities of the protein bands indicated by the arrow were quantified by image analysis to measure the amount of remaining protein. The band intensities were normalized by the amount of protein for each construct when incubated with 0 µM plasmin and plotted.

Figure 26A:
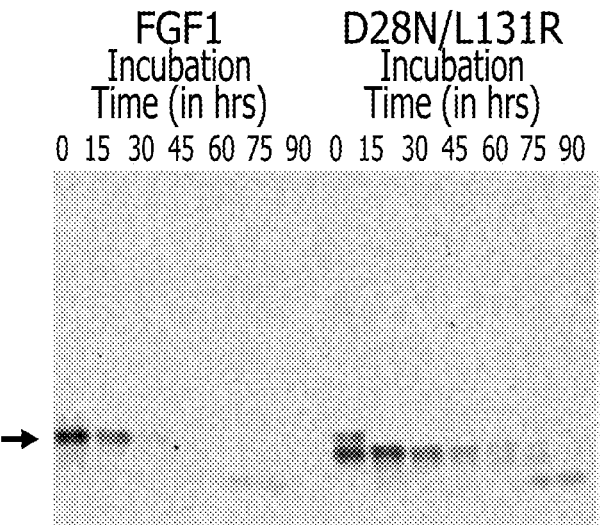
Figure 26B:
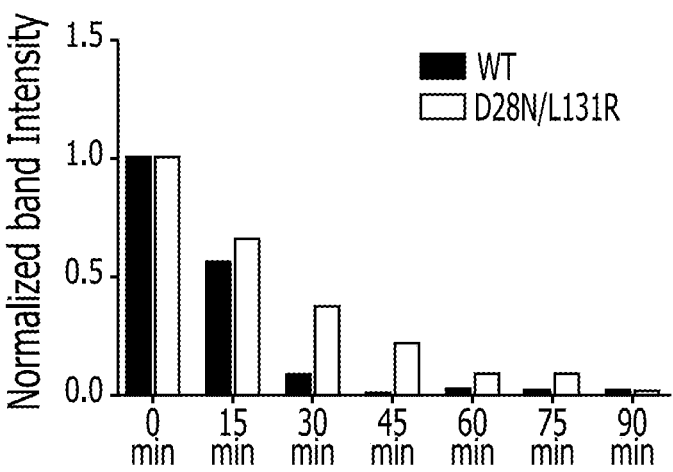

FIG. 26A-FIG. 26B Proteolytic stability assay of FGF1 WT and BS4M1 in trypsin. The FGF1 BS4M1 (D28N/L131R) mutant shows greater proteolytic stability in trypsin as compared to wild-type FGF1. 100 ng of FGF1 was incubated with 1:20 molar ratio of trypsin to FGF1 for various incubation times at 37° C. The incubated samples were run on separate lanes of a Western blot against FGF1 to measure the extent of protein degradation at each time point. The band intensities of the protein bands indicated by the arrow were quantified by image analysis to measure the amount of remaining protein. The band intensities were normalized by the amount of protein for each construct at the time point t=0 and plotted.

Figure 27A:
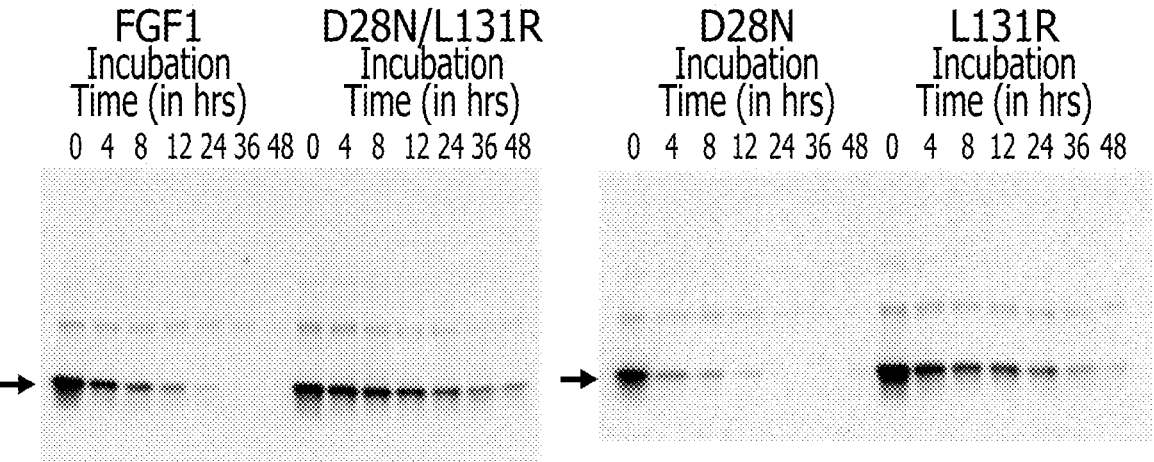
Figure 27B:
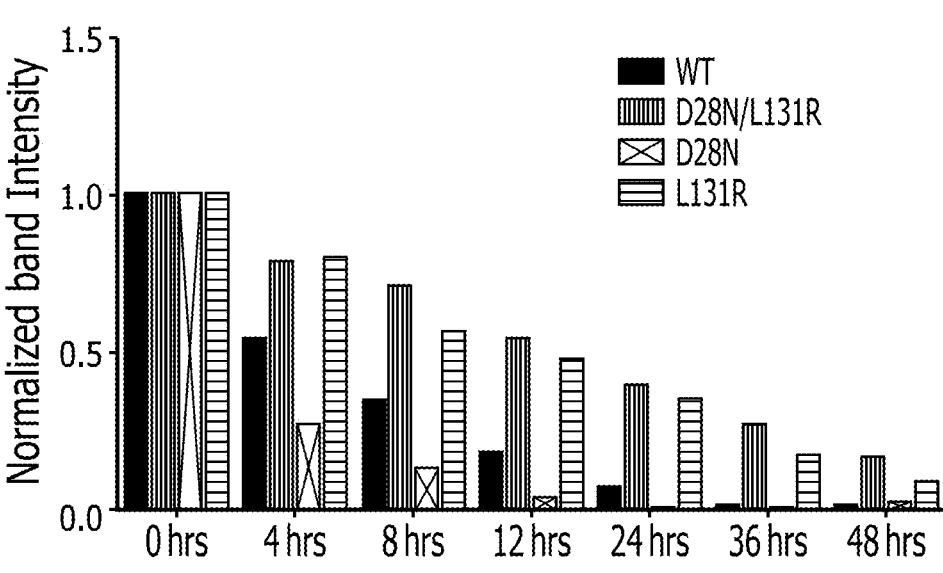

FIG. 27A-FIG. 27B Proteolytic stability assay of FGF1 WT, BS4M1, D28N, and L131R in plasmin. The FGF1 L131R single mutant retains most of its proteolytic stability as compared to BS4M1. The FGF1 D28N single mutant has a lower proteolytic stability even as compared to wild-type FGF1. 100 ng of FGF1 was incubated for 48 hours at 37° C. with various concentrations of plasmin. The incubated samples were run on separate lanes of a Western blot against FGF1 to measure the extent of protein degradation at each time point. The band intensities of the protein bands indicated by the arrow were quantified by image analysis to measure the amount of remaining protein. The band intensities were normalized by the amount of protein for each construct when incubated with 0 µM plasmin and plotted.

Figure 28A:
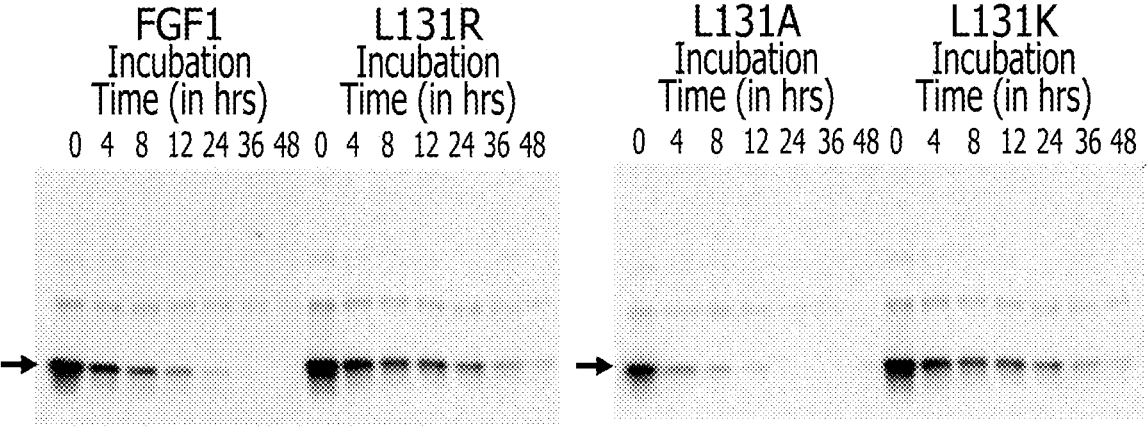
Figure 28B:
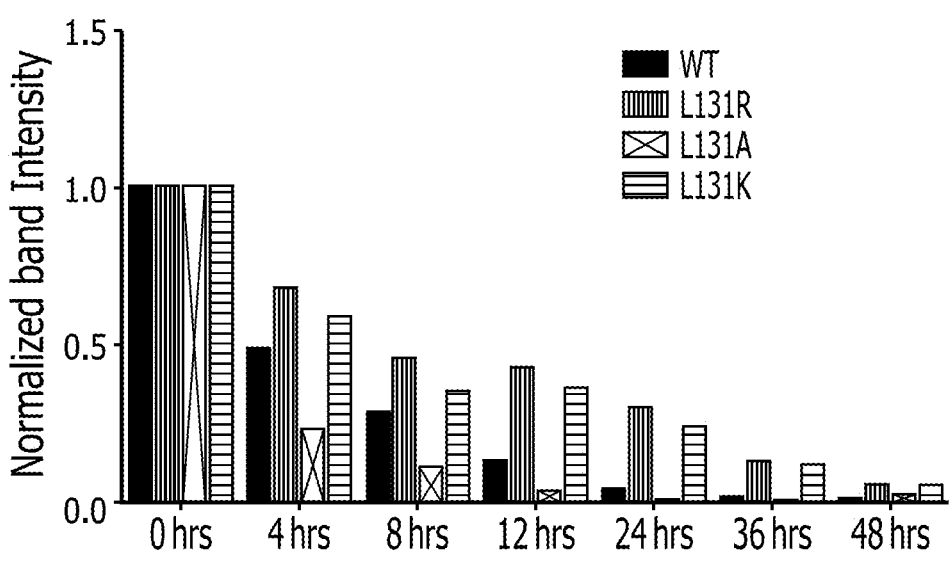

FIG. 28A-FIG. 28B Proteolytic stability assay of FGF1 WT, L131R, L131A, and L131K in plasmin. The FGF1 L131K single mutant retains most of its proteolytic stability as compared to FGF1 L131R. The FGF1 L131A single mutant has a lower proteolytic stability even as compared to wild-type FGF1. 100 ng of FGF1 was incubated for 48 hours at 37° C. with various concentrations of plasmin. The incubated samples were run on separate lanes of a Western blot against FGF1 to measure the extent of protein degradation at each time point. The band intensities of the protein bands indicated by the arrow were quantified by image analysis to measure the amount of remaining protein. The band intensities were normalized by the amount of protein for each construct when incubated with 0 µM plasmin and plotted.

Figure 29A:
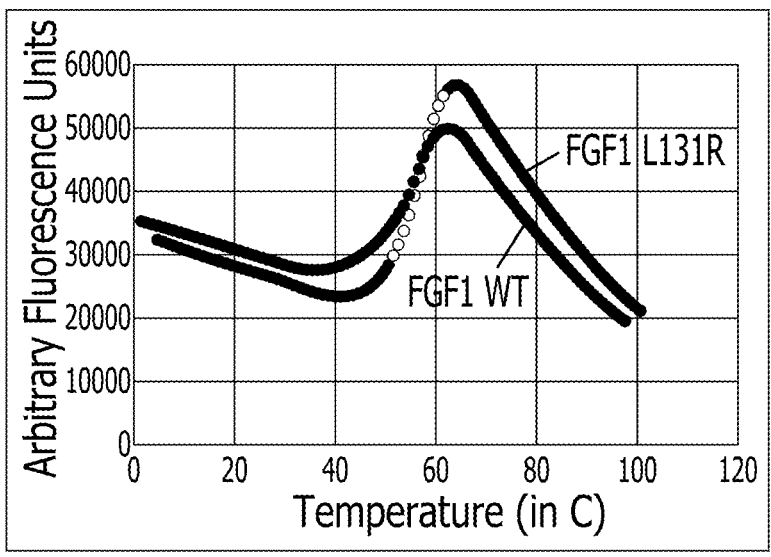
Figure 29B:
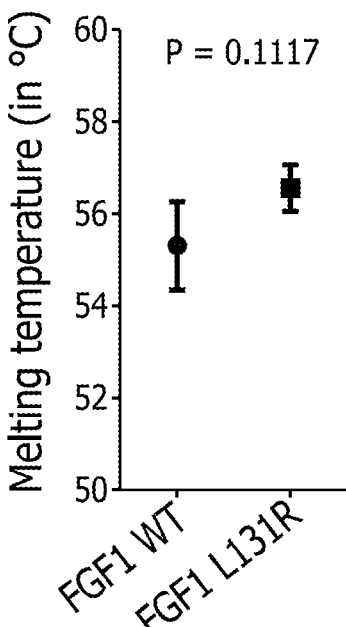

FIG. 29A-FIG. 29B ThermoFluor assay of FGF1 wild-type and L131R mutant. The melting temperatures of FGF1 wild-type and the L131R mutant were measured in triplicate and plotted. There was no statistically significant difference between the melting temperatures of the two proteins.

Figure 30A:
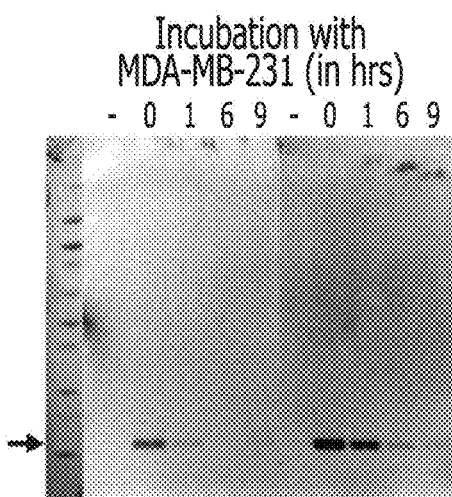
Figure 30B:
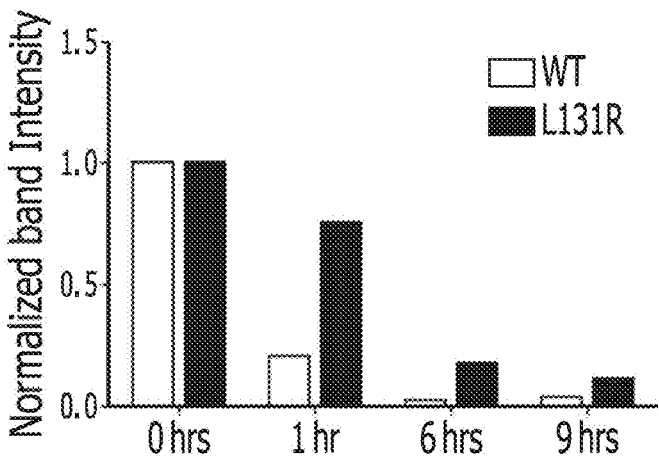

FIG. 30A-FIG. 30B Stability of FGF1 wild-type and L131R mutant in MDA-MB-231 culture. The FGF1 L131R mutant shows greater stability in culture with MDA-MB-231 as compared to wild-type FGF1. 500 ng of FGF1 was incubated with MDA-Mb-231 cells for various incubation times at 37° C. The incubated samples were concentrated and run on separate lanes of a Western blot against FGF1 to measure the extent of protein degradation at each time point. The band intensities of the protein bands indicated by the arrow were quantified by image analysis to measure the amount of remaining protein. The band intensities were normalized by the time point t=0 for each protein and plotted.

Figure 31A:
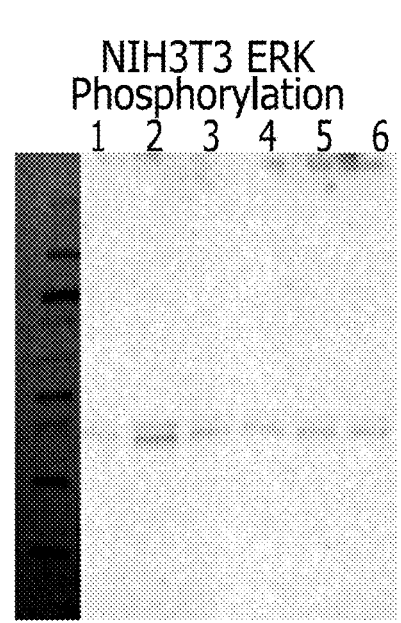
Figure 31A:
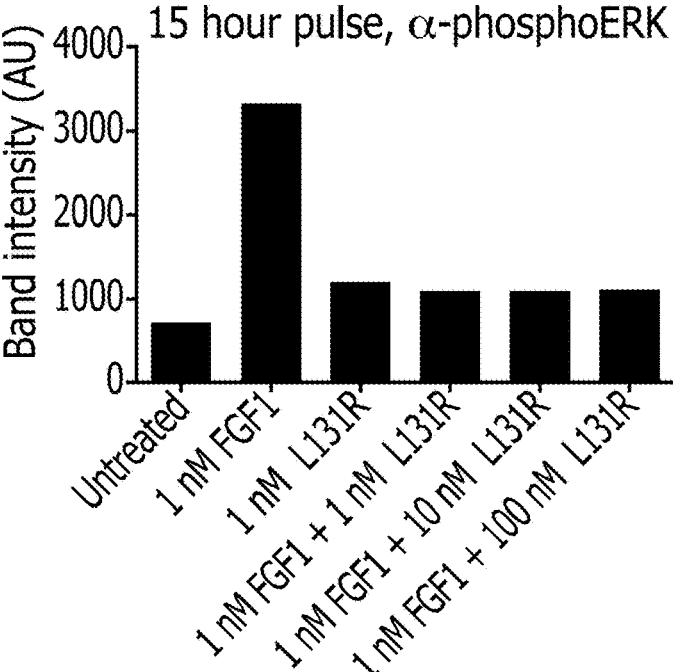
Figure 31B:
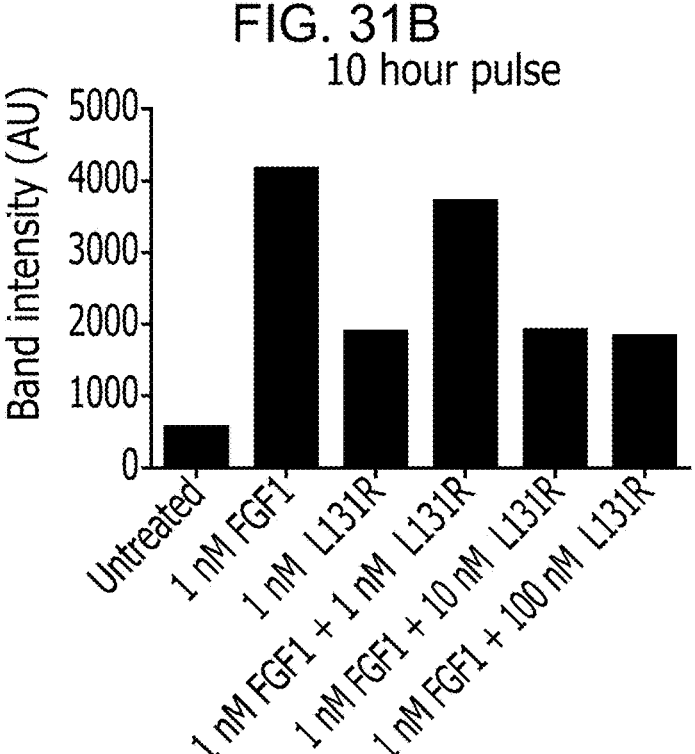

FIG. 31A-FIG. 31B NIH3T3 ERK Phosphorylation assay. The FGF1 L131R mutant inhibits NIH3T3 ERK phosphorylation by wild-type FGF1. NIH3T3 cells were stimulated for 15 hours with FGF1 wild-type and/or various concentrations of FGF1 L131R mutant. Cells were lysed and the lysate was probed with anti-phosphoERK on a Western blot. The band intensities were quantified by image analysis to measure the extent of FGF pathway activation. Bottom panel: NIH3T3 cells were stimulated for 10 hours with FGF1 wild-type and/or various concentrations of FGF1 L131R mutant.

Figure 32A:
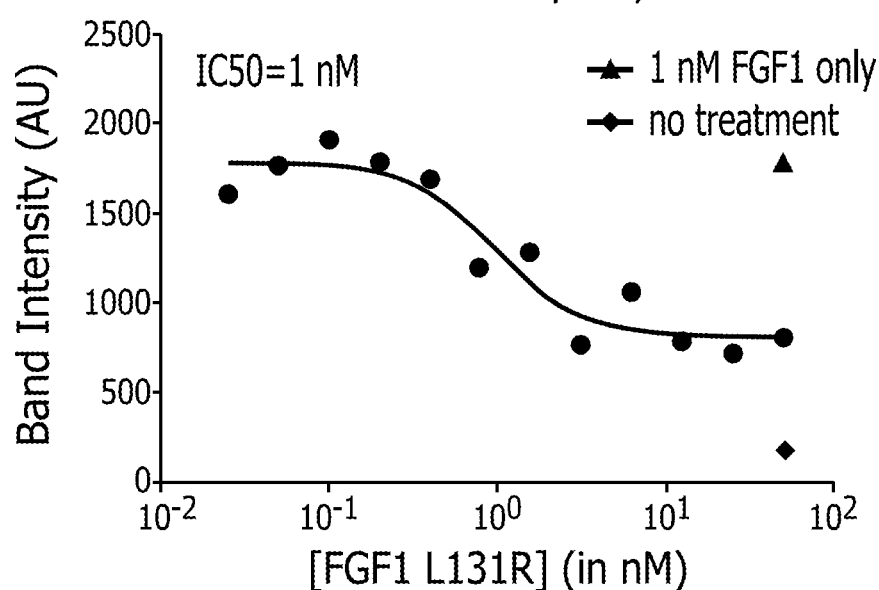
Figure 32B:
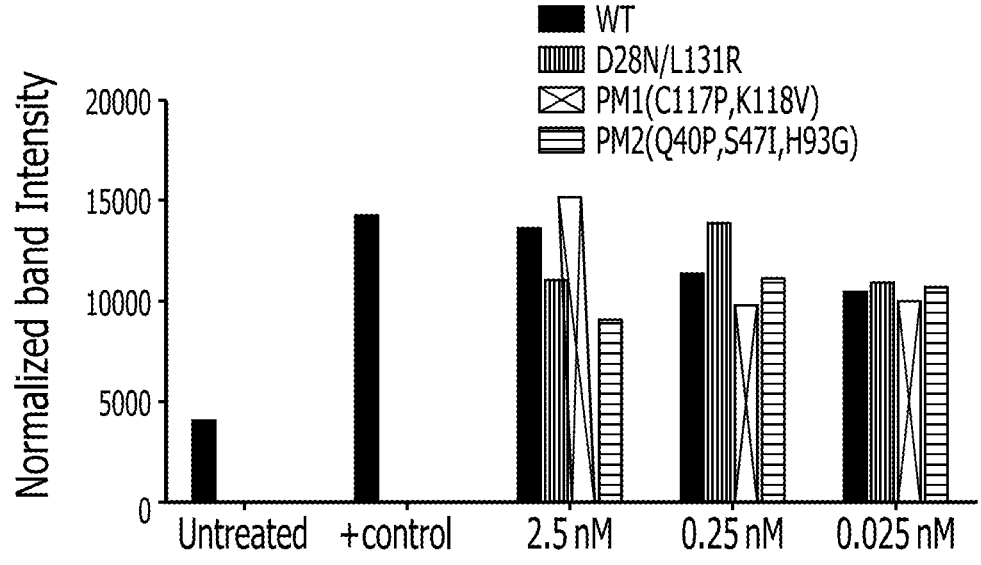

FIG. 32A-FIG. 32B Inhibition of FGF1-stimulated ERK phosphorylation by FGF1 L131R mutant in NIH3T3 cells. NIH3T3 cells were incubated with 1 nM FGF1 and various concentrations of FGF1 L131R. The extent of ERK phosphorylation for each condition is measured by Western blot against phosphoERK. The band intensities were quantified by image analysis and plotted to obtain an IC50 value.

Figure 33:
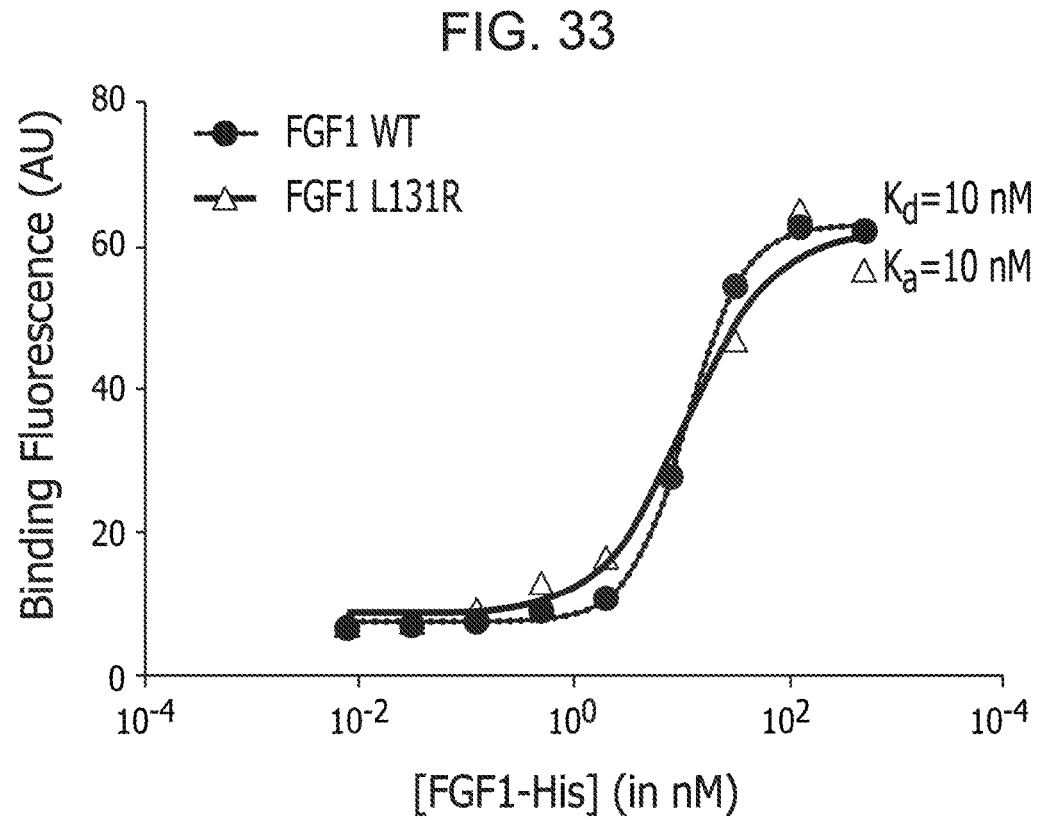

FIG. 33 Binding of FGF1 wild-type and L131R mutant to NIH3T3 cells. Equilibrium binding titrations of His-tagged FGF1 WT and L131R mutant to FGFR-expressing NIH3T3 cells. Cells were incubated at 4° C. with varying concentrations of each protein, and stained with fluorescent antibody against His to quantify binding to the cells.

Figure 34A:
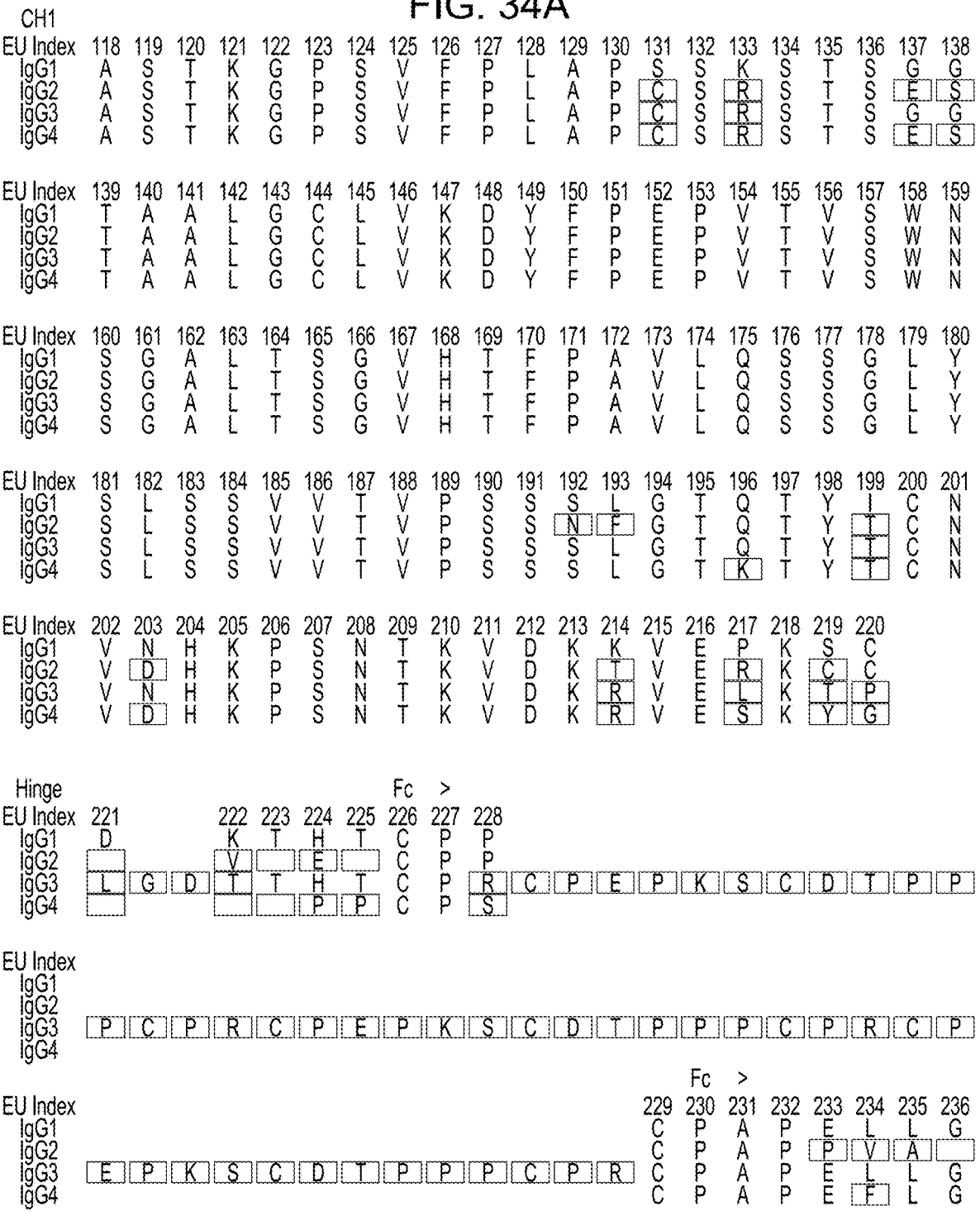
Figure 34B:
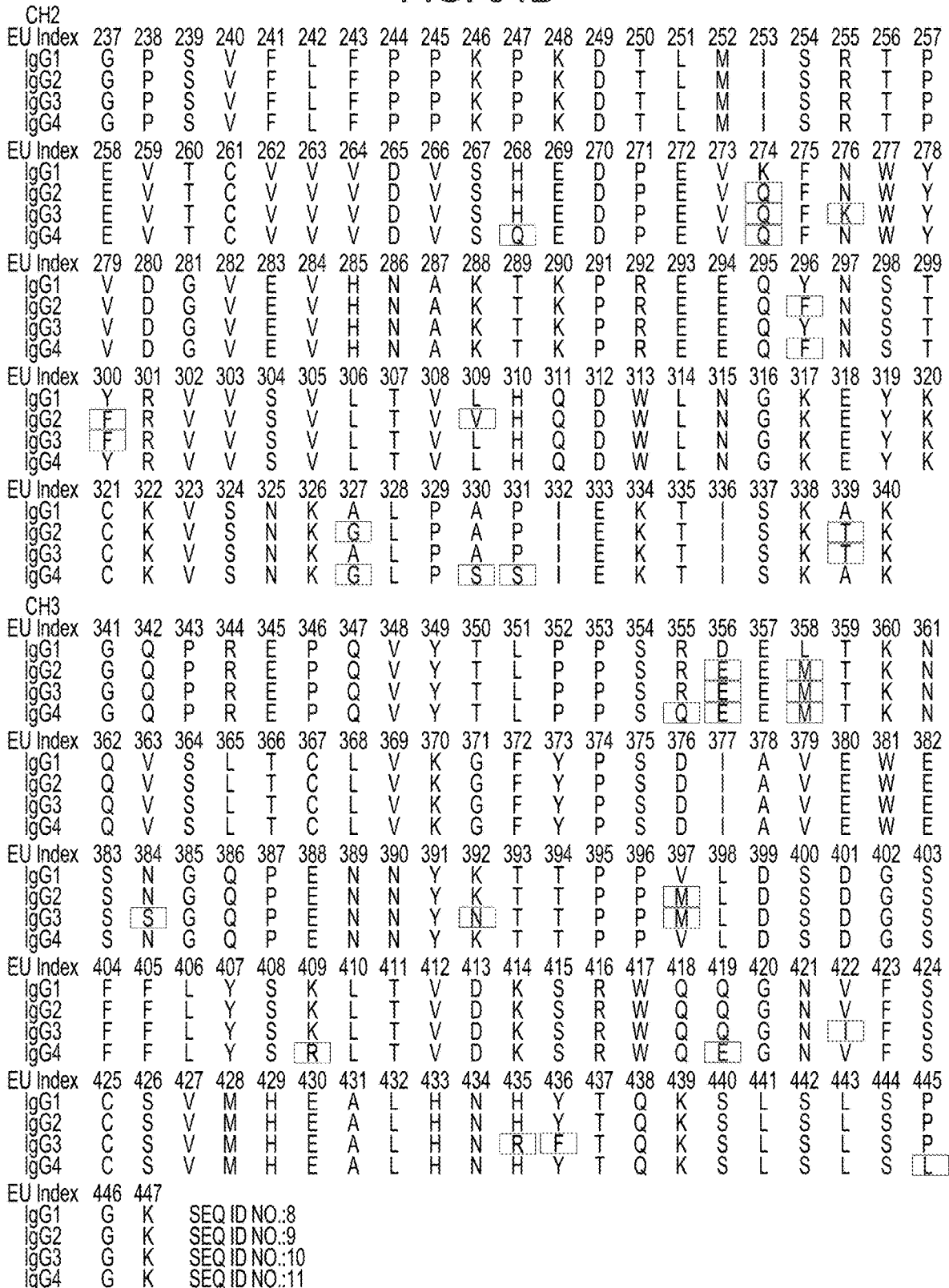

FIG. 34A-FIG. 34B Provides examples of IgG1(SEQ ID NO: 8), IgG2 (SEQ ID NO:9), IgG3 (SEQ ID NO:10), and IgG4 sequences (SEQ ID NO: 11).

DETAILED DESCRIPTION OF THE INVENTION

I. Introduction

The fibroblast growth factors are a family of cell signaling proteins that are involved in a wide variety of processes, most notably as crucial elements for normal development. These growth factors generally act as systemic or locally circulating molecules of extracellular origin that activate cell surface receptors. The mammalian fibroblast growth factor receptor family has 4 members, FGFR1, FGFR2, FGFR3, and FGFR4. The FGFRs consist of three extracellular immunoglobulin-type domains (D1-D3), a single-span transmembrane domain and an intracellular split tyrosine kinase domain. FGFs interact with the D2 and D3 domains, with the D3 interactions primarily responsible for ligand-binding specificity (see below). Heparan sulfate binding is mediated through the D3 domain. A short stretch of acidic amino acids located between the D1 and D2 domains has auto-inhibitory functions. This 'acid box' motif interacts with the heparan sulfate binding site to prevent receptor activation in the absence of FGFs. Each FGFR binds to a specific subset of the FGFs. Similarly, most FGFs can bind to several different FGFR subtypes. FGF1 is sometimes referred to as the 'universal ligand' as it is capable of activating all 7 different FGFRs. In contrast, FGF7 (keratinocyte growth factor, KGF) binds only to FGFR2b (KGFR).

The present invention provides methods for a combinatorial approach to engineering proteolytically stable growth factors using the yeast display platform and flow-activated cell sorting (FACS) for screening. The process of setting up the screening method using FGF1 as a model example is described and methods for engineering an exemplary proteolytically stable growth factor are provided. The present invention also provides the characterization of a proteolytically stable FGF1 mutant.

II. Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures of analytical and synthetic organic chemistry described below are those well-known and commonly employed in the art. Standard techniques, or modifications thereof, are used for chemical syntheses and chemical analyses.

The terms "BS4M1" and "PM2", and "PM3 refer to variants of SEQ ID NO:1 having the following substitutions: (i) BS4M1 (D28N and L131R), (ii) PM2 (Q40P, S47I, H93G), and (iii) PM3 (D28N, Q40P, S47I, H93G, L131R). FGF1: FNLPPGNYKKPKLLYCSNGGHFLRIL-PDGTVDGTRDRSDQHIQLQLSAESVGEVYIKS TETGQYLAMDTDGLLYGSQTPNEECLFLERLEEN-HYNTYISKKHAEKNWFVGLKKN GSCKRGPR-THYGQKAILFLPLPVSSD (SEQ ID NO:1). SEQ ID NO:1 is the FGF1 sequence without the propeptide (uniprot.org/blast/?about=P05230[16-155] &key=Chain&id=PRO_0000008908). The numbering described herein is based on the first amino acid of the sequence above being position 1 (ex: F1, N2, etc.). Other numbering for FGF1 can include the propeptide sequence in the numbering, which would cause the numbering to be larger by 14. However, the numbering herein is based on SEQ ID NO:1 and does not include the FGF1 propeptide.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene. Moreover, as used herein, a nucleic acid encoding a polypeptide variant of the invention is defined to include the nucleic acid sequence complementary to this nucleic acid sequence.

The term "gene" means the segment of DNA involved in producing a polypeptide chain. It may include regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure. An isolated nucleic acid can be a component of an expression vector.

Typically, isolated polypeptides of the invention have a level of purity preferably expressed as a range. The lower end of the range of purity for the polypeptide is about 60%, about 70% or about 80% and the upper end of the range of purity is about 70%, about 80%, about 90%, about 95%, or more than about 95%. When the polypeptides are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, mass-spectroscopy, or a similar means).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), His (H), Glu (E), Asn (N), Gln (Q), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include His (H), Arg (R) and Lys (K).

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:125-142. Exemplary hydrophobic amino acids include Ile (I), Phe (F), Val (V), Leu (L), Trp (W), Met (M), Ala (A), Gly (G), Tyr (Y), Pro (P), and proline analogues.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently (C$_1$-C$_6$) alkyl, substituted (C$_1$-C$_6$) alkyl, (C$_1$-C$_6$) alkenyl, substituted (C$_1$-C$_6$) alkenyl, (C$_1$-C$_6$) alkynyl, substituted (C$_1$-C$_6$) alkynyl, (C$_1$-C$_{21}$)) aryl, substituted (C$_5$-C$_{20}$) aryl, (C$_6$-C$_{26}$) alkaryl, substituted (C$_6$-C$_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The amino acid residue Cys (C) is unusual in that it can form disulfide bridges with other Cys (C) residues or other sulfonyl-containing amino acids. The ability of Cys (C) residues (and other amino acids with -SH containing side chains) to exist in a peptide in either the reduced free-SH or oxidized disulfide-bridged form affects whether Cys (C) residues contribute net hydrophobic or hydrophilic character to a peptide. While Cys (C) exhibits a hydrophobicity of 0.29 according to the normalized consensus scale of Eisenberg (Eisenberg, 1984, supra), it is to be understood that for purposes of the present invention Cys (C) is categorized as a polar hydrophilic amino acid, notwithstanding the general classifications defined above.

The term "linker" refers to an amino-acid polypeptide spacer that covalently links two or more polypeptides. The linker can be 1-15 amino acid residues. Preferably the linker is a single cysteine residue. The linker can also have the amino acid sequence SEQ ID NO:2 KES-CAKKQRQHMDS.

As will be appreciated by those of skill in the art, the above-defined categories are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, especially in light of the detailed disclosure provided herein.

Certain amino acid residues, called "helix breaking" amino acids, have a propensity to disrupt the structure of α-helices when contained at internal positions within the helix. Amino acid residues exhibiting such helix-breaking properties are well-known in the art (see, e.g., Chou and Fasman, Ann. Rev. Biochem. 47:251-276) and include Pro (P), Gly (G) and potentially all D-amino acids (when contained in an L-peptide; conversely, L-amino acids disrupt helical structure when contained in a D-peptide) as well as a proline analogue. While these helix-breaking amino acid residues fall into the categories defined above, with the exception of Gly (G) (discussed infra), these residues should not be used to substitute amino acid residues at internal positions within the helix—they should only be used to substitute 1-3 amino acid residues at the N-terminus and/or C-terminus of the peptide.

While the above-defined categories have been exemplified in terms of the genetically encoded amino acids, the amino acid substitutions need not be, and in certain embodiments preferably are not, restricted to the genetically encoded amino acids. Indeed, many of the preferred peptides of formula (I) contain genetically non-encoded amino acids. Thus, in addition to the naturally occurring genetically encoded amino acids, amino acid residues in the core peptides of formula (I) may be substituted with naturally occurring non-encoded amino acids and synthetic amino acids.

Certain commonly encountered amino acids which provide useful substitutions for the core peptides of formula (I) include, but are not limited to, β-alanine(β-Ala) and other omega-amino acids such as 3-aminopropionic acid, 2, 3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); omithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-chlorophenylalanine (Phe (4-Cl)); 2-fluorophenylalanine (Phe (2-F)); 3-fluorophenylalanine (Phe (3-F)); 4-fluorophenylalanine (Phe (4-F)); penicillamine (Pen); 1/2/3/4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe (pNH2)); N-methyl valine (MeVal); homocysteine (hCys), homophenylalanine (hPhe) and homoserine (hSer); hydroxyproline (Hyp), homoproline (hPro), N-methylated amino acids and peptoids (N-substituted glycines). In addition, in some embodiments the amino acid proline in the core peptides of formula (I) is substantiated with a proline analogue, including, but not limited to, azetidine-2-carboxylate (A2C), L-Thiazolidine-4-carboxylic Acid, cis-4-hydroxy-L-proline (CHP), 3,4-dehydroproline, thioproline, and isonipecotic acid (Inp).

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure, therefore, consider functional or biological equivalents of a polypeptide or protein as set forth above. In particular, embodiments of the invention provide variants having about 50%, 60%, 70%, 80%, 90%, and 95% sequence identity to the parent polypeptide. In various embodiments, the invention provides variants having this level of identity to a portion of the parent polypeptide sequence, e.g., the wild-type growth factor including for example wild-type FGF1 (SEQ ID NO: 1). In various embodiments, the variant has at least about 95%, 96%, 97%, 98% or 99% sequence identity to the parent polypeptide or to a portion of the parent polypeptide sequence, e.g., the wild-type growth factor including for example wild-type FGF1 (SEQ ID NO:1), as defined herein.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

"Identity," as known in the art, is a relationship between two or more polypeptide or protein sequences, as determined by comparing the sequences. In the art, "identity" also refers to the degree of sequence relatedness between polypeptides or proteins, as determined by the match between strings of such sequences. "Identity" can be readily calculated by known bioinformational methods.

"Peptide" refers to a polymer in which the monomers are amino acids and are joined together through amide bonds. Peptides of the present invention can vary in size, e.g., from two amino acids to hundreds or thousands of amino acids. A larger peptide (e.g., at least 10, at least 20, at least 30 or at least 50 amino acid residues) is alternatively referred to as a "polypeptide" or "protein". Additionally, unnatural amino acids, for example, β-alanine, phenylglycine, homoarginine and homophenylalanine are also included. Amino acids that are not gene-encoded may also be used in the present invention. Furthermore, amino acids that have been modified to include reactive groups, glycosylation sequences, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" or "polypeptide" refers to both glycosylated and non-glycosylated peptides or "polypeptides". Also included are polypeptides that are incompletely glycosylated by a system that expresses the polypeptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

In the present application, amino acid residues are numbered (typically in the superscript) according to their relative positions from the N-terminal amino acid (e.g., N-terminal methionine) of the polypeptide, which is numbered "1". The N-terminal amino acid may be a methionine (M), numbered "1". The numbers associated with each amino acid residue can be readily adjusted to reflect the absence of N-terminal methionine if the N-terminus of the polypeptide starts without a methionine. It is understood that the N-terminus of an exemplary polypeptide can start with or without a methionine. Accordingly, in instances in which an amino acid linker is added to the N-terminus of a wild-type polypeptide, the first linker amino acid adjoined to the N-terminal amino acid is number −1 and so forth. For example, if the linker has the amino acid sequence KESCAKKQRQHMDS, (SEQ ID NO:2) with the S residue adjoined to the N-terminal amino acid of the wild-type polypeptide, then the most N-terminal linker amino acid K would be −14, while the most C-terminal linker amino acid S would be −1. In this way, the numbering of amino acids in the wild type polypeptide and linker bound wild type polypeptide is preserved.

The term "parent polypeptide" refers to a wild-type polypeptide and the amino acid sequence or nucleotide sequence of the wild-type polypeptide is part of a publicly accessible protein database (e.g., EMBL Nucleotide Sequence Database, NCBI Entrez, ExPasy, Protein Data Bank and the like).

The term "mutant polypeptide" or "polypeptide variant" or "mutein" or "variant polypeptide" refers to a form of a polypeptide, wherein its amino acid sequence differs from the amino acid sequence of its corresponding wild-type (parent) form, naturally existing form or any other parent form. A mutant polypeptide can contain one or more mutations, e.g., replacement, insertion, deletion, etc. which result in the mutant polypeptide.

The term "corresponding to a parent polypeptide" (or grammatical variations of this term) is used to describe a polypeptide of the invention, wherein the amino acid sequence of the polypeptide differs from the amino acid sequence of the corresponding parent polypeptide only by the presence of at least amino acid variation. Typically, the amino acid sequences of the variant polypeptide and the parent polypeptide exhibit a high percentage of identity. In one example, "corresponding to a parent polypeptide" means that the amino acid sequence of the variant polypeptide has at least about 50% identity, at least about 60%, at least about 70%, at least about 80%, at least about 90%, at least about 95% or at least about 98% identity to the amino acid sequence of the parent polypeptide. In another example, the nucleic acid sequence that encodes the variant polypeptide has at least about 50% identity, at least about 60%, at least about 70%, at least about 80%, at least about 90%, at least about 95% or at least about 98% identity to the nucleic acid sequence encoding the parent polypeptide. In some embodiments, the parent polypeptide corresponds to the FGF1 of SEQ ID NO:1.

The term "introducing (or adding etc.) a variation into a parent polypeptide" (or grammatical variations thereof), or "modifying a parent polypeptide" to include a variation (or grammatical variations thereof) do not necessarily mean that the parent polypeptide is a physical starting material for such conversion, but rather that the parent polypeptide provides the guiding amino acid sequence for the making of a variant polypeptide. In one example, "introducing a variant into a parent polypeptide" means that the gene for the parent polypeptide is modified through appropriate mutations to create a nucleotide sequence that encodes a variant polypeptide. In another example, "introducing a variant into a parent polypeptide" means that the resulting polypeptide is theoretically designed using the parent polypeptide sequence as a guide. The designed polypeptide may then be generated by chemical or other means.

The term "library" refers to a collection of different polypeptides each corresponding to a common parent polypeptide. Each polypeptide species in the library is referred to as a member of the library. Preferably, the library of the present invention represents a collection of polypeptides of sufficient number and diversity to afford a population from which to identify a lead polypeptide. A library includes at least two different polypeptides. In one embodiment, the library includes from about 2 to about 100,000,000 members. In another embodiment, the library includes from about 10,000 to about 100,000,000 members. In yet another embodiment, the library includes from about 100,000 to about 100,000,000 members. In a further embodiment, the library includes from about 1,000,000 to about 100,000,000 members. In another embodiment, the library includes from about 10,000,000 to about 100,000,000 members. In yet another embodiment, the library includes more than 100 members.

The members of the library may be part of a mixture or may be isolated from each other. In one example, the members of the library are part of a mixture that optionally includes other components. For example, at least two poly-peptides are present in a volume of cell-culture broth. In another example, the members of the library are each expressed separately and are optionally isolated. The iso-lated polypeptides may optionally be contained in a multi-well container, in which each well contains a different type of polypeptide. In another example, the members of the library are each expressed as fusions to a yeast or bacteria cell or phage or viral particle.

As used herein, the term "polymeric modifying group" is a modifying group that includes at least one polymeric moiety (polymer). The polymeric modifying group added to a polypeptide can alter a property of such polypeptide, for example, its bioavailability, biological activity or its half-life in the body. Exemplary polymers include water soluble and water insoluble polymers. A polymeric modifying group can be linear or branched and can include one or more indepen-dently selected polymeric moieties, such as poly(alkylene glycol) and derivatives thereof. In one example, the polymer is non-naturally occurring. In an exemplary embodiment, the polymeric modifying group includes a water-soluble poly-mer, e.g., poly(ethylene glycol) and derivatives thereof (PEG, m-PEG), poly(propylene glycol) and derivatives thereof (PPG, m-PPG) and the like. In a preferred embodi-ment, the poly(ethylene glycol) or poly(propylene glycol) has a molecular weight that is essentially homodisperse. In one embodiment the polymeric modifying group is not a naturally occurring polysaccharide.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include anti-bodies, antibody fragments, transferrin, HS-glycoprotein, coagulation factors, serum proteins, β-glycoprotein, G-CSF, GM-CSF, M-CSF, EPO and the like.

The term "Fc-fusion protein", as used herein, is meant to encompass proteins, in particular therapeutic proteins, com-prising an immunoglobulin-derived moiety, which will be called herein the "Fc-moiety", and a moiety derived from a second, non-immunoglobulin protein, which will be called herein the "therapeutic moiety", irrespective of whether or not treatment of disease is intended.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g., multivalent agents.

Therapeutic moiety also includes proteins and constructs that include proteins.

As used herein, "anti-tumor drug" means any agent useful to combat cancer including.

As used herein, "a cytotoxin or cytotoxic agent" means any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracinedione, mitoxantrone, mithramycin, actinomycin D, 1-dehydrotestosterone, glucocorticoids, procaine, tetra-caine, lidocaine, propranolol, and puromycin and analogs or homologs thereof. Other toxins include, for example, ricin, CC-1065 and analogues, the duocarmycins. Still other tox-ins include diptheria toxin, and snake venom (e.g., cobra venom).

As used herein, "a radioactive agent" includes any radio-isotope that is effective in diagnosing or destroying a tumor. Examples include, but are not limited to, indium-111, cobalt-60, fluorine-18, copper-64, copper-67, lutetium-177, or tech-nicium-99m. Additionally, naturally occurring radioactive elements such as uranium, radium, and thorium, which typically represent mixtures of radioisotopes, are suitable examples of a radioactive agent. The metal ions are typically chelated with an organic chelating moiety. The radioactive agent or radionuclide can be a component of an imaging agent.

Near-infrared dyes can also be conjugated using standard chemistries for optical imaging applications. "Near infrared" refers to radiation in the portion of the electromagnetic spectrum adjacent to that portion associated with visible light, for example, from about 0.7 m to about 1 μm. The near infrared dye may include, for example, a cyanine or indo-cyanine derivative such as Cy5.5. The infrared dye may also include phosphoramidite dyes, for example, IRDye® 800 (LI-COR® Biosciences).

Many useful chelating groups, crown ethers, cryptands and the like are known in the art and can be incorporated into the compounds of the invention (e.g., EDTA, DTPA, DOTA, NTA, HDTA, etc. and their phosphonate analogs such as DTPP, EDTP, HDTP, NTP, etc). See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACRO-CYCLIC LIGAND COMPLEXES; Cambridge University Press, Cam-bridge, 1989; Dugas, BIOORGANIC CHEMISTRY; Springer-Verlag, New York, 1989, and references contained therein. Additionally, a manifold of routes allowing the attachment of chelating agents, crown ethers and cyclodex-trins to other molecules is available to those of skill in the art. See, for example, Meares et al., "Properties of In Vivo Chelate-Tagged Proteins and Polypeptides." In, MODIFICA-TION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., Bio-conjugate Chem., 9: 108-117 (1998); Song et al., Biocon-jugate Chem., 8: 249-255 (1997). These metal binding agents can be used to bind a metal ion detectable in an imaging modality.

As used herein, "pharmaceutically acceptable carrier" includes any material, which when combined with the conjugate retains the conjugates' activity and is non-reactive with the subject's immune systems. "Pharmaceutically acceptable carrier" includes solids and liquids, such as vehicles, diluents and solvents. Examples include, but are not limited to, any of the standard pharmaceutical carriers such as a phosphate buffered saline solution, water, emul-sions such as oil/water emulsion, and various types of wetting agents. Other carriers may also include sterile solu-tions, tablets including coated tablets and capsules. Typi-cally such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

As used herein, "administering" means oral administration, administration as a suppository, topical contact, intravenous, intraperitoneal, intramuscular, intrathecal, intralesional, or subcutaneous administration, administration by inhalation, or the implantation of a slow-release device, e.g., a mini-osmotic pump, to the subject. Administration is by any route including parenteral and transmucosal (e.g., oral, nasal, vaginal, rectal, or transdermal), particularly by inhalation. Parenteral administration includes, e.g., intravenous, intramuscular, intra-arteriole, intradermal, subcutaneous, intraperitoneal, intraventricular, and intracranial. Moreover, where injection is to treat a tumor, e.g., induce apoptosis, administration may be directly to the tumor and/or into tissues surrounding the tumor. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including preventing the disease or condition from occurring in a subject (e.g., human) that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "effective amount" or "an amount effective to" or a "therapeutically effective amount" or any grammatically equivalent term means the amount that, when administered to an animal or human for treating a disease, is sufficient to effect treatment for that disease. An effective amount can also refer to the amount necessary to cause a cellular response, including for example, apoptosis, cell cycle initiation, and/or signal transduction.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science,* 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds. ORGANIC FUNCTIONAL GROUP PREPARATIONS, Academic Press, San Diego, 1989).

III. The Variants

In some embodiments, the variant is a proteolutically stable variant as compared to the wild-type growth factor. In an exemplary embodiment, the variant exhibits increased proteolytic stability as compared to wild-type. In some embodiments, the variant is any variant of a wild-type growth factor. In some embodiments, the variant is an antagonist for the growth factor receptor to which the wild-type growth factor binds.

In some embodiments, the variant is a variant of FGF1. In some embodiments, a variant of human fibroblast growth factor 1 (FGF1) comprising at least one member selected from an amino acid substitution, an amino acid deletion, an amino acid addition and combinations thereof is provided. In some embodiments, a variant of human fibroblast growth factor 1 (FGF1) comprising at least one member selected from an amino acid substitution, an amino acid deletion, an amino acid addition and combinations thereof, wherein the resulting FGF1 variant exhibits increased proteolytic stability as compared to wild-type FGF1 of SEQ ID NO:1 is provided. In some embodiments, the FGF1 variant comprises an amino acid substitution, an amino acid deletion, an amino acid addition and combinations thereof in the β-loop or near the C-terminus. In some embodiments, the FGF1 variant is a fibroblast growth factor receptor (FGFR) antagonist. The present invention provides an FGF1 polypeptide including at least one amino acid in at least one position in which this amino acid is not found in the parent FGF1 polypeptide (wild type, SEQ ID NO:1).

(SEQ ID NO: 1)
FNLPPGNYKKPKLLYCSNGGHFLRILPDGTVDGTRDRSDQHIQLQLSAESV

GEVYIKSTETGQYLAMDTDGLLYGSQTPNEECLFLERLEENHYNTYISKKH

AEKNWFVGLKKNGSCKRGPRTHYGQKAILFLPLPVSSD.

In some embodiments, the FGF1 variant of SEQ ID NO:1 having at least one amino acid substitution. In some embodiments, the FGF1 variant comprises at least one amino acid substitution at position 28, 40, 47, 93 or 131. In some embodiments, the FGF1 variant comprise at least one amino acid substitution selected from the group consisting of D28N, Q40P, S47I, H93G, L131R, and L131K. In some embodiments, the FGF1 variant comprises amino acid substitution L131R. In some embodiments, the FGF1 variant comprises amino acid substitution L131K. In some embodiments, the variant comprises amino acid substitutions D28N and L131R. In some embodiments, the variant comprises amino acid substitutions D28N and L131K. In some embodiments, the variant comprises amino acid substitutions Q40P, S47I, H93G, and L131R. In some embodiments, the variant comprises amino acid substitutions Q40P, S47I, H93G, and L131K. In some embodiments, the variant comprises amino acid substitutions D28N, Q40P, S47I, H93G, and L131R. In some embodiments, the variant comprises amino acid substitutions D28N, Q40P, S47I, H93G, and L131K. In some embodiments, the FGF1 variant does not comprise the amino acid substitution L131A.

In some embodiments, the variant FGF1 is the variant referred to as BS4M1 (D28N and L131R) variant. In some embodiments, BS4M1 comprises the sequence (SEQ ID NO: 3)
FNLPPGNYKKPKLLYCSNGGHFLRILPDGTVDGTRDRSDPHIQLQLIAESV

GEVYIKSTETGQYLAMDTDGLLYGSQTPNEECLFLERLEENGYNTYISKKH

AEKNWFVGLKKNGSCKRGPRTHYGQKAILFLPLPVSSD.

In some embodiments, the variant FGF1 is the variant referred to as PM2 (Q40P, S47I, H93G). In some embodiments, PM2 comprises the sequence (SEQ ID NO: 4)
FNLPPGNYKKPKLLYCSNGGHFLRILPNGTVDGTRDRSDPHIQLQLIAESV

GEVYIKSTETGQYLAMDTDGLLYGSQTPNEECLFLERLEENGYNTYISKKH

AEKNWFVGLKKNGSCKRGPRTHYGQKAIRFLPLPVSSD.

In some embodiments, the variant FGF1 is the variant referred to as PM3 (D28N, Q40P, S47I, H93G, L131R). In some embodiments, PM3 comprises the sequence (SEQ ID NO: 5)
FNLPPGNYKKPKLLYCSNGGHFLRILPDGTVDGTRDRSDQHIQLQLSAESV

GEVYIKSTETGQYLAMDTDGLLYGSQTPNEECLFLERLEENHYNTYISKKH

AEKNWFVGLKKNGSCKRGPRTHYGQKAIRFLPLPVSSD.

In some embodiments, variant FGF1 comprises the sequence (SEQ ID NO: 6)
FNLPPGNYKKPKLLYCSNGGHFLRILPDGTVDGTRDRSDQHIQLQLSAESV

GEVYIKSTETGQYLAMDTDGLLYGSQTPNEECLFLERLEENHYNTYISKKH

AEKNWFVGLKKNGSCKRGPRTHYGQKAIKFLPLPVSSD.

In some embodiments, variant FGF1 comprises the sequence (SEQ ID NO: 7)
FNLPPGNYKKPKLLYCSNGGHFLRILPDGTVDGTRDRSDQHIQLQLSAESV

GEVYIKSTETGQYLAMDTDGLLYGSQTPNEECLFLERLEENHYNTYISKKH

AEKNWFVGLKKNGSCKRGPRTHYGQKAIRFLPLPVSSD.

In some embodiments, the variant is an isolated variant. In some embodiments, the variant exhibits at least one desirable characteristic not present in the present polypeptide. Exemplary characteristics include, but are not limited to, an increase in proteolytic stability, an increase in thermal stability, an increase or decrease in conformational flexibility and increased antagonistic activity. As will be appreciated by those of skill in the art, the variant may exhibit any combination of two or more of these improved characteristics.

In some embodiments, the variant FGF1 is an antagonist for the FGFR receptor. In some embodiments, the FGF1 variant has a sequence selected from the group consisting of SEQ ID NO:3, SEQ ID NO:4. SEQ ID NO:5, SEQ ID NO:6, SEQ ID NO:7, In some embodiments, the growth factor variants have a sequence identity with the parent polypeptide of at least about 80%, at least about 85%, at least about 90%, at least about 95% or at least about 96%, 97%, 98% or 99%. In some embodiments, the growth factor variants of the invention have a sequence identity with the parent poly peptide of at least about 99.2%, at least about 99.4%, at least about 99.6% or at least about 99.8%.

In some embodiments, the FGF1 variants have a sequence identity with the parent polypeptide of at least about 80%, at least about 85%, at least about 90%, at least about 95% or at least about 96%, 97%, 98% or 99%. In some embodiments, the FGF1 variants of the invention have a sequence identity with the parent poly peptide of at least about 99.2%, at least about 99.4%, at least about 99.6% or at least about 99.8%.

In some embodiments, the positions of SEQ ID NO:1, which are mutated include one or more of 28, 40, 47, 93 or 131. As those of skill will realize, any combination of these positions can be mutated.

In some embodiments, an amino acid of the parent polypeptide at position 28 is altered to N, as compared to the wild-type FGF1 (e.g., SEQ ID NO:3; SEQ ID NO:5).

In some embodiments, an amino acid of the parent polypeptide at position 40 is altered to P.

In some embodiments, an amino acid of the parent polypeptide at position 47 is altered to I.

In some embodiments, an amino acid of the parent polypeptide at position 93 is altered to G.

In some embodiments, an amino acid of the parent polypeptide at position 131 is altered to R. In some embodiments, an amino acid of the parent polypeptide at position 131 is altered to K.

a. Conjugates

The present invention provides conjugates of the variants of the invention with one or more conjugation partner. Exemplary conjugation partners include polymers, targeting Fc-moiety is derived from the heavy chain of an immunoglobulin, preferably an IgG. More preferably, the Fc-moiety comprises a portion, such as e.g., a domain, of an immunoglobulin heavy chain constant region (see, for example, Table 1; IgG1 (SEQ ID NO:8), IgG2 (SEQ ID NO:9), IgG3 (SEQ ID NO:10), or IgG4 (SEQ ID NO:11)). Such Ig constant region preferably comprises at least one Ig constant domain selected from any of the hinge, CH2, CH3 domain, or any combination thereof. In some embodiments, the Fc-moiety comprises at least a CH2 and CH3 domain. It is further preferred that the Fc-moiety comprises the IgG hinge region, the CH2 and the CH3 domain.

TABLE 1

Exemplary IgG sequences:

| SEQ ID NO: | Name | Sequence | | | | | | |
|---|---|---|---|---|---|---|---|---|
| 8 | IgG1 | ASTKGPSVFP | LAPSSKSTSG | GTAALGCLVK | DYFPEPVTVS | WNSGALTSGV | HTFPAVLQSS | 60 |
| | | GLYSLSSVVT | VPSSSLGTQT | YICNVNHKPS | NTKVDKKVEP | KSCDKTHTCP | PCPAPELLGG | 120 |
| | | PSVFLFPPKP | KDTLMISRTP | EVTCVVVDVS | HEDPEVKFNW | YVDGVEVHNA | KTKPREEQYN | 180 |
| | | STYRVVSVLT | VLHQDWLNGK | EYKCKVSNKA | LPAPIEKTIS | KAKGQPREPQ | VYTLPPSRDE | 240 |
| | | LTKNQVSLTC | LVKGFYPSDI | AVEWESNGQP | ENNYKTTPPV | LDSDGSFFLY | SKLTVDKSRW | 300 |
| | | QQGNVFSCSV | MHEALHNHYT | QKSLSLSPGK | | | | 330 |
| | | | | | | | | |
| 9 | IgG2 | ASTKGPSVFP | LAPCSRSTSE | STAALGCLVK | DYFPEPVTVS | WNSGALTSGV | HTFPAVLQSS | 60 |
| | | GLYSLSSVVT | VPSSNFGTQT | YTCNVDHKPS | NTKVDKTVER | KCCVECPPCP | APPVAGPSVF | 120 |
| | | LFPPKPKDTL | MISRTPEVTC | VVVDVSHEDP | EVQFNWYVDG | VEVHNAKTKP | REEQFNSTFR | 180 |
| | | VVSVLTVVHQ | DWLNGKEYKC | KVSNKGLPAP | IEKTISKTKG | QPREPQVYTL | PPSREEMTKN | 240 |
| | | QVSLTCLVKG | FYPSDIAVEW | ESNGQPENNY | KTTPPMLDSD | GSFFLYSKLT | VDKSRWQQGN | 300 |
| | | VFSCSVMHEA | LHNHYTQKSL | SLSPGK | | | | 326 |
| | | | | | | | | |
| 10 | IgG3 | ASTKGPSVFP | LAPCSRSTSG | GTAALGCLVK | DYFPEPVTVS | WNSGALTSGV | HTFPAVLQSS | 60 |
| | | GLYSLSSVVT | VPSSSLGTQT | YTCNVNHKPS | NTKVDKRVEL | KTPLGDTTHT | CPRCPEPKSC | 120 |
| | | DTPPPCPRCP | EPKSCDTPPP | CPRCPEPKSC | DTPPPCPRCP | APELLGGPSV | FLFPPKPKDT | 180 |
| | | LMISRTPEVT | CVVVDVSHED | PEVQFKWYVD | GVEVHNAKTK | PREEQYNSTF | RVVSVLTVLH | 240 |
| | | QDWLNGKEYK | CKVSNKALPA | PIEKTISKTK | GQPREPQVYT | LPPSREEMTK | NQVSLTCLVK | 300 |
| | | GFYPSDIAVE | WESSGQPENN | YNTTPPMLDS | DGSFFLYSKL | TVDKSRWQQG | NIFSCSVMHE | 360 |
| | | ALHNRFTQKS | LSLSPGK | | | | | 377 |
| | | | | | | | | |
| 11 | IgG4 | ASTKGPSVFP | LAPCSRSTSE | STAALGCLVK | DYFPEPVTVS | WNSGALTSGV | HTFPAVLQSS | 60 |
| | | GLYSLSSVVT | VPSSSLGTKT | YTCNVDHKPS | NTKVDKRVES | KYGPPCPSCP | APEFLGGPSV | 120 |
| | | FLFPPKPKDT | LMISRTPEVT | CVVVDVSQED | PEVQFNWYVD | GVEVHNAKTK | PREEQFNSTY | 180 |
| | | RVVSVLTVLH | QDWLNGKEYK | CKVSNKGLPS | SIEKTISKAK | GQPREPQVYT | LPPSQEEMTK | 240 |
| | | NQVSLTCLVK | GFYPSDIAVE | WESNGQPENN | YKTTPPVLDS | DGSFFLYSRL | TVDKSRWQEG | 300 |
| | | NVFSCSVMHE | ALHNHYTQKS | LSLSLGK | | | | 327 | agents, therapeutic agents, cytotoxic agents, chelating agents and detectable agents. Those of skill will recognize that there is overlap between these non-limiting agent categories.

The conjugation partner or "modifying group" can be any conjugatable moiety. Exemplary modifying groups are discussed below. The modifying groups can be selected for their ability to alter the properties (e.g., biological or physicochemical properties) of a given polypeptide. Exemplary polypeptide properties that may be altered by the use of modifying groups include, but are not limited to, pharmacokinetics, pharmacodynamics, metabolic stability, biodistribution, water solubility, lipophilicity, tissue targeting capabilities and the therapeutic activity profile. Modifying groups are useful for the modification of polypeptides of use in diagnostic applications or in in vitro biological assay systems.

In some embodiments, a growth factor variant, including for example, an FGF1 variant as described herein is combined with an Fc moiety. The Fc-moiety may be derived from a human or animal immunoglobulin (Ig) that is preferably an IgG. The IgG may be an IgG1, IgG2, IgG3 or IgG4 (see, for example FIG. 34). It is also preferred that the Fc domains of the IgG1 subclass are often used as the Fc moiety, because IgG1 has the longest serum half-life of any of the serum proteins. Lengthy serum half-life can be a desirable protein characteristic for animal studies and potential human therapeutic use. In addition, the IgG1 subclass possesses the strongest ability to carry out antibody mediated effector functions.

The primary effector function that may be most useful in a fusion protein is the ability for an IgG1 antibody to mediate antibody dependent cellular cytotoxicity. On the other hand, this could be an undesirable function for a fusion protein that functions primarily as an antagonist. Several of the specific amino acid residues that are important for antibody constant region-mediated activity in the IgG1 subclass have been identified. Inclusion or exclusion of these specific amino acids therefore allows for inclusion or exclusion of specific immunoglobulin constant region-mediated activity.

In accordance with the present invention, the Fc-moiety may also be modified in order to modulate effector functions. For instance, the following Fc mutations, according to EU index positions (Kabat et al., 1991), can be introduced if the Fc-moiety is derived from IgG1: T250Q/M428L; M252Y/S254T/T256E+H433K/N434F; E233P/L234V/L235A/AA236+A327G/A330S/P331S; E333A; K322A.

Further Fc mutations may e.g. be the substitutions at EU index positions selected from 330, 331 234, or 235, or combinations thereof. An amino acid substitution at EU index position 297 located in the CH2 domain may also be introduced into the Fc-moiety in the context of the present invention, eliminating a potential site of N-linked carbohydrate attachment. The cysteine residue at EU index position 220 may also be replaced.

The Fc-fusion protein of the invention may be a monomer or dimer. The Fc-fusion protein may also be a "pseudo-dimer", containing a dimeric Fc-moiety (e.g. a dimer of two disulfide-bridged hinge-CH2-CH3 constructs), of which only one is fused to a therapeutic moiety.

The Fc-fusion protein may be a heterodimer, containing two different therapeutic moieties, or a homodimer, containing two copies of a single therapeutic moiety.

In some embodiments, the in vivo half-life of the growth factor variant, including for example, an FGF1 variant, as described herein can be enhanced with polyethylene glycol (PEG) moieties. Chemical modification of polypeptides with PEG (PEGylation) increases their molecular size and typically decreases surface- and functional group-accessibility, each of which are dependent on the number and size of the PEG moieties attached to the polypeptide. Frequently, this modification results in an improvement of plasma half-live and in proteolytic-stability, as well as a decrease in immunogenicity and hepatic uptake (Chaffee et al. *J Clin. Invest.* 89: 1643-1651 (1992); Pyatak et al. *Res. Commun. Chem. Pathol Pharmacol.* 29: 113-127 (1980)). For example, PEGylation of interleukin-2 has been reported to increase its antitumor potency in vivo (Katre et al. *Proc. Natl. Acad. Sci. USA.* 84: 1487-1491 (1987)) and PEGylation of a F(ab')2 derived from the monoclonal antibody A7 has improved its tumor localization (Kitamura et al. *Biochem. Biophys. Res. Commun.* 28: 1387-1394 (1990)). Thus, in another embodiment, the in vivo half-life of a polypeptide derivatized with a PEG moiety by a method of the invention is increased relative to the in vivo half-life of the non-derivatized parent polypeptide.

The increase in polypeptide in vivo half-life is best expressed as a range of percent increase relative to the parent polypeptide. The lower end of the range of percent increase is about 40%, about 60%, about 80%, about 100%, about 150% or about 200%. The upper end of the range is about 60%, about 80%, about 100%, about 150%, or more than about 250%.

Many water-soluble polymers are known to those of skill in the art and are useful in practicing the present invention. The term water-soluble polymer encompasses species such as saccharides (e.g., dextran, amylose, hyalouronic acid, poly(sialic acid), heparans, heparins, etc.); poly(amino acids), e.g., poly(aspartic acid) and poly(glutamic acid); nucleic acids; synthetic polymers (e.g., poly(acrylic acid), poly(ethers), e.g., poly(ethylene glycol); peptides, proteins, and the like. The present invention may be practiced with any water-soluble polymer with the sole limitation that the polymer must include a point at which the remainder of the conjugate can be attached. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002).

In another embodiment, analogous to those discussed above, the modified sugars include a water-insoluble polymer, rather than a water-soluble polymer. The conjugates of the invention may also include one or more water-insoluble polymers. This embodiment of the invention is illustrated by the use of the conjugate as a vehicle with which to deliver a therapeutic polypeptide in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly(ethylene terephthalate), poly(vinyl acetate), polyvinyl chloride, polystyrene, polyvinyl pyrrolidone, pluronics and polyvinylphenol and copolymers thereof.

Representative biodegradable polymers of use in the conjugates of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

Exemplary resorbable polymers include, for example, synthetically produced resorbable block copolymers of poly (α-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J Biomed. Mater. Res.* 21: 1301-1316 (1987); and Cohn et al., *J Biomed. Mater. Res.* 22: 993-1009 (1988).

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

In another embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811, which issued on Jun. 11, 1985. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The present invention also provides conjugates analogous to those described above in which the polypeptide is conjugated to a therapeutic moiety, diagnostic moiety, targeting moiety, toxin moiety or the like. Each of the above-recited moieties can be a small molecule, natural polymer (e.g., polypeptide) or a synthetic polymer.

In various embodiments, the variant is conjugated to a component of a matrix for tissue regeneration. Exemplary matrices are known in the art and it is within the ability of a skilled worker to select and modify an appropriate matrix with of the growth factor variant, including for example, an FGF1 variant, of the invention. The growth factor variant, including for example, an FGF1 variant, of the invention are generally of use in regenerative medicine applications, including the regeneration of, e.g., eye, liver, muscle, nerve and cardiac tissue.

In some embodiments, the invention provides conjugates that localize selectively in a particular tissue due to the presence of a targeting agent as a component of the conjugate. In an exemplary embodiment, the targeting agent is a protein. Exemplary proteins include transferrin (brain, blood pool), HS-glycoprotein (bone, brain, blood pool), antibodies (brain, tissue with antibody-specific antigen, blood pool), coagulation factors V-XII (damaged tissue, clots, cancer, blood pool), serum proteins, e.g., $\alpha$-acid glycoprotein, fetuin, $\alpha$-fetal protein (brain, blood pool), $\beta$2-glycoprotein (liver, atherosclerosis plaques, brain, blood pool), G-CSF, GM-CSF, M-CSF, and EPO (immune stimulation, cancers, blood pool, red blood cell overproduction, neuroprotection), albumin (increase in half-life), IL-2 and IFN-$\alpha$.

In another embodiment, the invention provides a conjugate between the growth factor variant, including for example, an FGF1 variant, of the invention and a therapeutic moiety. Therapeutic moieties, which are useful in practicing the instant invention include drugs from a broad range of drug classes having a variety of pharmacological activities. Methods of conjugating therapeutic and diagnostic agents to various other species are well known to those of skill in the art. See, for example Hermanson, Bioconjugate Techniques, Academic Press, San Diego, 1996; and Dunn et al., Eds. POLYMERIC DRUGS AND DRUG Delivery Systems, ACS Symposium Series Vol. 469, American Chemical Society, Washington, D.C. 1991.

Classes of useful therapeutic moieties include, for example, antineoplastic drugs (e.g., antiandrogens (e.g., leuprolide or flutamide), cytocidal agents (e.g., adriamycin, doxorubicin, taxol, cyclophosphamide, busulfan, cisplatin, $\beta$-2-interferon) anti-estrogens (e.g., tamoxifen), antimetabolites (e.g., fluorouracil, methotrexate, mercaptopurine, thioguanine). Also included within this class are radioisotope-based agents for both diagnosis and therapy, and conjugated toxins, such as ricin, geldanamycin, mytansin, CC-1065, the duocarmycins, Chlicheamycin and related structures and analogues thereof.

The therapeutic moiety can also be a hormone (e.g., medroxyprogesterone, estradiol, leuprolide, megestrol, octreotide or somatostatin); endocrine modulating drugs (e.g., contraceptives (e.g., ethinodiol, ethinyl estradiol, norethindrone, mestranol, desogestrel, medroxyprogesterone). Of use in various embodiments of the invention are conjugates with estrogens (e.g., diethylstilbesterol), glucocorticoids (e.g., triamcinolone, betamethasone, etc.) and progestogens, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful modifying groups include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine H2 antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

In some embodiments, the conjugate is formed by reaction between a reactive amino acid and a reactive conjugation partner for the reactive amino acid. Both the reactive amino acid and the reactive conjugation partner include within their framework one or more reactive functional group. One of the two binding species may include a "leaving group" (or activating group) refers to those moieties, which are easily displaced in enzyme-regulated nucleophilic substitution reactions or alternatively, are replaced in a chemical reaction utilizing a nucleophilic reaction partner (e.g., an amino acid moiety carrying a sufhydryl group). It is within the abilities of a skilled person to select a suitable leaving group for each type of reaction. Many activated sugars are known in the art. See, for example, Vocadlo et al., In Carbohydrate Chemistry and Biology, Vol. 2, Ernst et al. Ed., Wiley-VCH Verlag: Weinheim, Germany, 2000; Kodama et al., *Tetrahedron Lett.* 34: 6419 (1993); Lougheed, et al., *J Biol. Chem.* 274: 37717 (1999)).

In various embodiments, the amino acid substitution, which is the variant (or a variant) of naturally occurring FGF1, is the locus for attachment of the conjugation partner, e.g., a side-chain amino acid, e.g., cysteine, lysine, serine, etc.

Reactive groups and classes of reactions useful in practicing the present invention are generally those that are well known in the art of bioconjugate chemistry. Currently favored classes of reactions available with reactive sugar moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985; Hermanson, Bioconjugate Techniques, Academic Press, San Diego, 1996; and Feeney et al., Modification of Proteins; Advances in Chemistry Series, Vol. 198, American Chemical Society, Washington, D.C., 1982.

US 12,691,160 B2

29 b. Reactive Functional Groups

Useful reactive functional groups on a reactive amino acid or reactive conjugation partner include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be chosen such that they do not participate in, or interfere with, the reactions necessary to assemble the reactive sugar nucleus or modifying group. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

The group linking the polypeptide and conjugation partner can also be a cross-linking group, e.g., a zero- or higher-order cross-linking group (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and heterobifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

Exemplary conjugation partners attached to the polypeptides of the invention include, but are not limited to, PEG derivatives (e.g., alkyl-PEG, acyl-PEG, acyl-alkyl-PEG, alkyl-acyl-PEG carbamoyl-PEG, aryl-PEG), PPG derivatives (e.g., alkyl-PPG, acyl-PPG, acyl-alkyl-PPG, alkyl-acyl-PPG carbamoyl-PPG, aryl-PPG), therapeutic moieties, diagnostic moieties, mannose-6-phosphate, heparin, heparan, $Sle_x$, mannose, mannose-6-phosphate, Sialyl Lewis X, FGF, VFGF, proteins, chondroitin, keratan, dermatan, albumin, integrins, antennary oligosaccharides, peptides and the like.

In addition to covalent attachments, the growth factor variant, including for example, an FGF1 variant, of the instant invention can be attached onto the surface of a biomaterial through non-covalent interactions. Non covalent protein incorporation can be done, for example, through encapsulation or absorption. Attachment of the polypeptides of the instant invention to a biomaterial may be mediated through heparin. In some embodiments, the polypeptides of the instant invention are attached to a heparin-alginate polymer and alginate as described in Harada et al., J. Clin. Invest. (1994) 94:623-630; Laham et al., Circulation (1999) 1865-1871 and references cited therein. In other embodiments, the polypeptides of the instant invention are attached to a collagen based biomaterial.

c. Imaging Agents

An exemplary conjugate of the invention is an imaging agent comprising a variant of the invention and a detectable moiety, which is detectable in an imaging modality. There is a critical need for molecular imaging probes that will specifically target Met receptors in living subjects and allow noninvasive characterization of tumors for patient-specific cancer treatment and disease management. The ability to detect Met-expressing tumors through non-invasive imaging could also serve as an indicator of metastatic risk.

Exemplary imaging modalities in which the conjugates of the invention find use include, without limitation, positron emission tomography (PET) in which a variant of the invention is tagged with a positron emitting isotope. Typical isotopes include $^{11}C$, $^{13}N$, $^{15}O$, $^{18}F$, $^{64}Cu$, $^{62}Cu$, $^{124}I$, $^{76}Br$, $^{82}Rb$ and $^{68}Ga$, with $^{18}F$ being the most clinically utilized. The variants can also be incorporated into ultrasound agents, magnetic resonance imaging agents, X-ray agents, CT agents, gamma camera scintigraphy agents and fluorescent imaging agents. Additional detectable moieties and methods of imaging are set forth in the Methods section herein below.

In an exemplary embodiment, the conjugation partner is attached to a polypeptide variant of the invention via a linkage that is cleaved under selected conditions. Exemplary conditions include, but are not limited to, a selected pH (e.g., stomach, intestine, endocytotic vacuole), the presence of an active enzyme (e.g., esterase, reductase, oxidase), light, heat and the like. Many cleavable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J Biol. Chem.,* 261: 205-210 (1986); Browning et al., *J Immunol.,* 143: 1859-1867 (1989).

31
IV. Pharmaceutical Compositions

The growth factor variants, including for example, the FGF1 variants, and their conjugates of the invention have a broad range of pharmaceutical applications.

Thus, in another aspect, the invention provides a pharmaceutical composition including at least one polypeptide or polypeptide conjugate of the invention and a pharmaceutically acceptable diluent, carrier, vehicle, additive or combinations thereof. Pharmaceutical compositions of the invention are suitable for use in a variety of drug delivery systems. Suitable formulations for use in the present invention are found in *Remington's Pharmaceutical Sciences*, Mace Publishing Company, Philadelphia, PA, 17th ed. (1985). For a brief review of methods for drug delivery, see, Langer, *Science* 249:1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable matrices, such as microspheres (e.g., polylactate polyglycolate), may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered subcutaneously or parenterally, e.g., intravenously. Thus, the invention provides compositions for parenteral administration, which include the compound dissolved or suspended in an acceptable carrier, preferably an aqueous carrier, e.g., water, buffered water, saline, PBS and the like. The compositions may also contain detergents such as Tween 20 and Tween 80; stabilizers such as mannitol, sorbitol, sucrose, and trehalose; and preservatives such as EDTA and meta-cresol. The compositions may contain pharmaceutically acceptable auxiliary substances as required to approximate physiological conditions, such as pH adjusting and buffering agents, tonicity adjusting agents, wetting agents, detergents and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

In some embodiments the glycopeptides of the invention can be incorporated into liposomes formed from standard vesicle-forming lipids. A variety of methods are available for preparing liposomes, as described in, e.g., Szoka et al., *Ann. Rev. Biophys. Bioeng.* 9: 467 (1980), U.S. Pat. Nos. 4,235,871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively).

Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some embodiments, it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The growth factor variants, including for example, the FGF1 variants, prepared by the methods of the invention may also find use as diagnostic reagents. For example, labeled compounds can be used to locate areas of inflammation or tumor metastasis in a patient suspected of having an inflammation. For this use, the compounds can be labeled with $^{125}$I, $^{14}$C, or tritium.

V. Nucleic Acids

In some embodiments, the invention provides an isolated nucleic acid encoding the growth factor variant, including for example, the FGF1 variant, according to any of the embodiments set forth hereinabove. In some embodiments, the invention provides a nucleic acid complementary to this nucleic acid.

In some embodiments, the invention provides an expression vector including a nucleic acid encoding a polypeptide variant according to any of the embodiments set forth hereinabove operatively linked to a promoter.

VI. Libraries and Methods of Screening

Also provided in various embodiments is a library of the growth factor variant polypeptides, including for example, an FGF1 variant polypeptides, comprising a plurality of different members, wherein each member of the library corresponds to a common parent growth factor polypeptide or FGF1 parent polypeptide, and wherein each member of the library comprises an amino acid at a position at which the amino acid is not found in the parent polypeptide.

a. Library Creation

In order to generate a randomized library of FGF1 or other growth factors, oligonucleotides were prepared which coded for various FGF1 or other growth factor sequences. The DNA used to express growth factor variant polypeptide, including for example, an FGF1 variant polypeptides in yeast was prepared synthetically or by standard recombinant techniques. Where an amino acid was to be varied, twenty different codons, each coding for a different amino acid, were synthesized for a given position. Randomized oligonucleotide synthesis has been used to create a coding cassette in which about 5 to about 15 amino acids are randomized (see, e.g., Burritt et al., (1996) Anal. Biochem. 238:1 13; Lowman (1997) Annu. Rev. Biophys. Biomol. Struct. 26:410 24; Wilson (1998) Can. J. Microbiol. 44:313 329).

The yeast display vector typically used for evolution of improved mutants is called "pCT". The vector is further described in US 2004/0146976 to Wittrup, et al., published Jul. 29, 2004, entitled "Yeast cell surface display of proteins and uses thereof." As described there, the vector provides a genetic fusion of the N terminus of a polypeptide of interest to the C-terminus of the yeast Aga2p cell wall protein. The outer wall of each yeast cell can display approximately $10^4$-$10^5$ protein agglutinins. The vector contains the specific restriction sites and illustrates the transcriptional regulation by galactose, the N-terminal HA and C-terminal c-myc epitope tags and the Factor Xa protease cleavage site.

Figure 1:
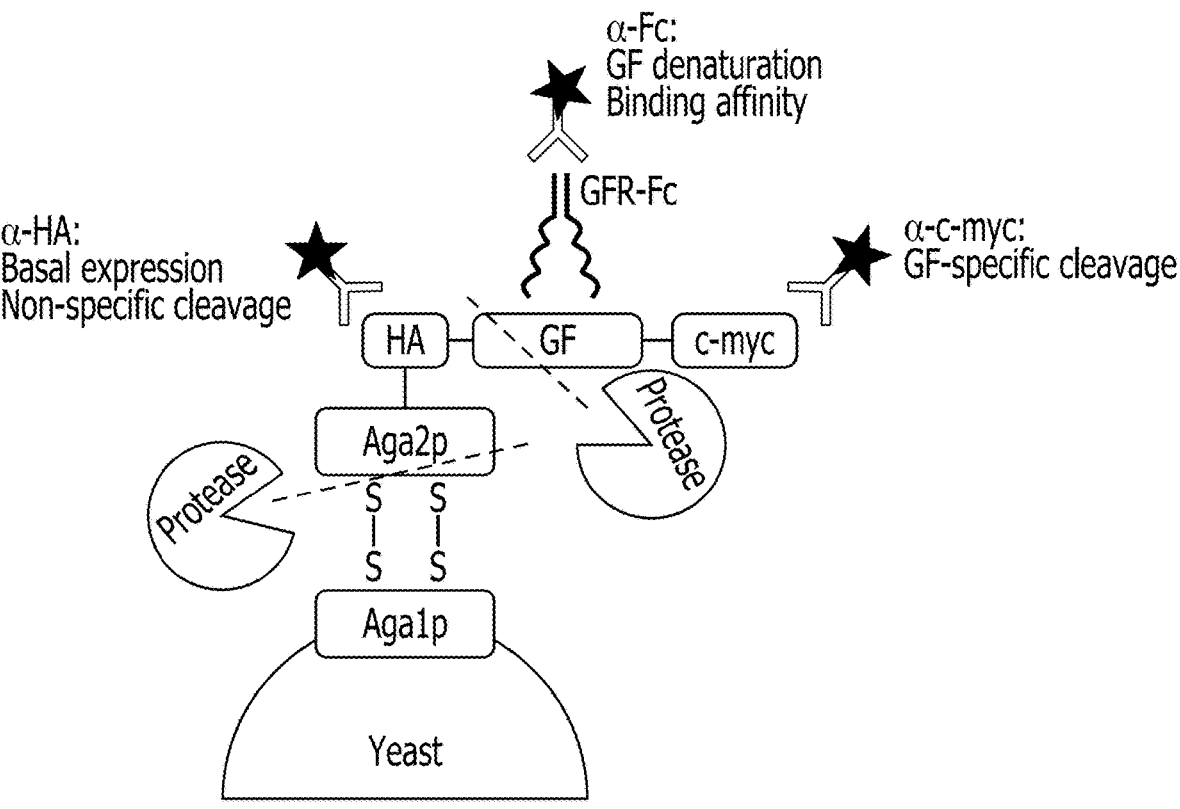
FIG. 1 Yeast display of growth factor for engineering proteolytic stability. The growth factor (GF) of interest is expressed as a fusion to adhesion protein agglutinin Aga2p, which is attached by two disulfide bonds to the cell wall protein Aga1p. Upon incubation with protease, cleavage can either occur within the growth factor (growth-factor-specific cleavage) or within the yeast display proteins Aga1p or Aga2p (non-specific cleavage). After incubation with the soluble Fc fusion of the growth factor receptor (GFR-Fc), fluorescent antibodies can be used to stain for the HA tag, the c-myc tag, and the Fc domain. The HA signal is used to measure basal expression level of the growth factor and non-specific cleavage by the protease. The c-myc signal is in conjunction with the HA signal to measure GF-specific cleavage. The Fc signal is used to measure the level of GF denaturation and the binding affinity of the GF for its receptor.

In some embodiments of the present invention, the yeast display platform, which is commonly used to engineer high affinity binders, is also utilized to engineer proteins with greater proteolytic stability (see, for example, FIG. 1). In some embodiments, several thousand copies of a single growth factor variant are displayed on the surface of yeast as tethered fusions. In some embodiments, the hemagglutinin (HA) tag is expressed upstream of the growth factor while the c-myc tag is expressed downstream of the growth factor. In some embodiments, cells can be incubated with soluble Fc fusions of the corresponding receptor, which can bind to the yeast displayed growth factor.

Figure 2:
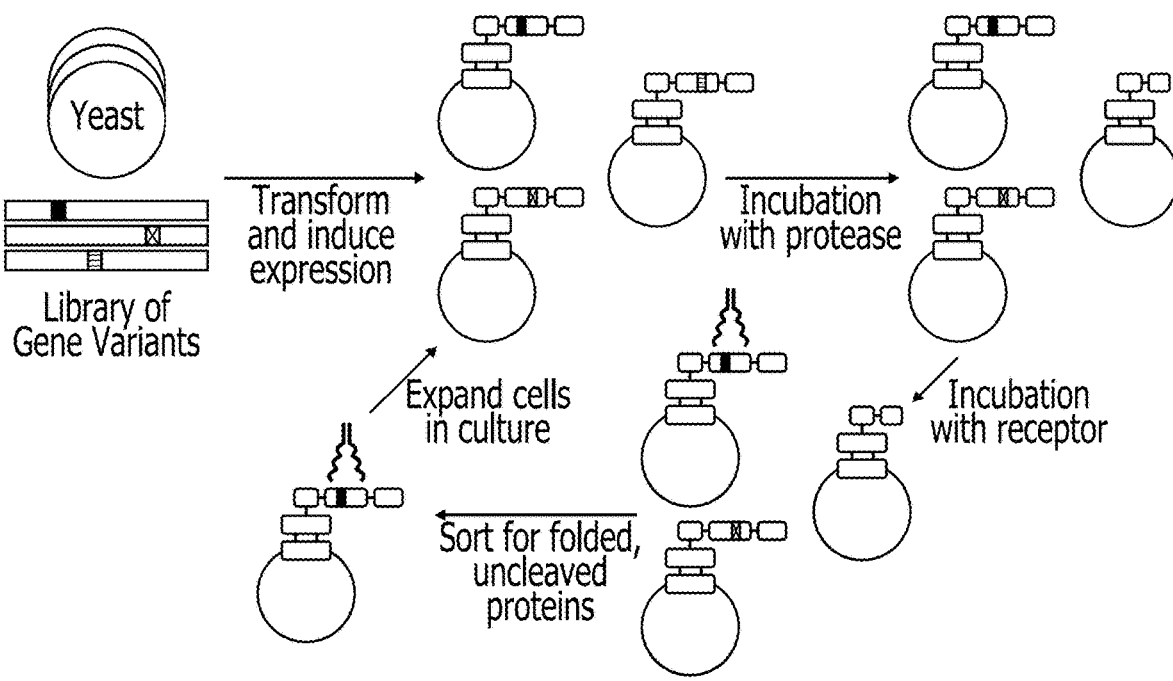
FIG. 2 FACS-based screening method for proteolytically stable growth factor mutants. A library of growth factor mutants is transformed into EBY100 yeast cells and induced to display growth factors by yeast display. Cells are incubated with protease, washed, then incubated with soluble Fc-fusion of the receptor. After labeling with appropriate fluorescent antibodies, flow activated cell sorting (FACS) is used to gate and collect cells that express mutants with low level of proteolytic cleavage and high levels of binding to the soluble receptor. This process of incubation and cell sorting is cycled multiple times to identify the mutants with greatest level of proteolytic stability.

In some embodiments, the yeast display platform is combined with flow-activated cell sorting (FACS) to engineer growth factors with higher proteolytic stability (see, for example, FIG. 2). In some embodiments, a library of growth factor mutants can be generated by random mutagenesis, directed mutagenesis, or DNA shuffling, or other recombinant techniques as discussed above or known in the art. In some embodiments, the library of yeast cells is incubated with a protease of interest, during which cleavage of the yeast surface displayed proteins occurs. In some embodiments, the growth factor mutants with greater proteolytic stability are more resistant to cleavage on the yeast cell surface. In some embodiments, after protease incubation, the cells are washed and incubated with soluble Fc fusions of the functional receptor that bind to properly folded growth factor mutants with retained receptor binding affinity. In some embodiments, FACS is used to sort for properly folded, uncleaved growth factor mutants, which are expanded and induced for the next round of sorting.

In some embodiments, fluorescent antibody markers against the Fc domain, the c-myc domain, and the HA tag are used to measure receptor binding, growth factor-specific cleavage, and non-specific cleavage (see, for example, Table 2 below). In some embodiments, detection of the bound Fc-fusion receptor allows for confirming that mutations in the growth factor do not severely reduce the binding affinity for the receptor or lead to improper protein folding. In some embodiments, growth factor-specific cleavage is a direct measure of a growth factor's proteolytic stability. In some embodiments, growth factor-specific cleavage is detected by the c-myc signal, as a cleaved growth factor will have the C-terminal c-myc tag removed. In some embodiments, non-specific cleavage occurs when the protease cleaves within the yeast surface display proteins, for example, the yeast display proteins Aga1p and Aga2p. In some embodiments, during non-specific cleavage, the fluorescent signals for all three markers are decreased. In some embodiments, this is undesirable, as the dynamic range for detecting growth factor cleavage and binding activity are decreased. In some embodiments, the HA signal is used to ensure that non-specific cleavage by the protease of interest is minimal.

TABLE 2

| Effect of different events on the observed signal from fluorescent antibody markers. | | | |
|---|---|---|---|
| | HA | c-myc | Fc |
| Denaturation/loss of binding affinity | | | ↓ |
| Growth factor-specific cleavage | | ↓ | ↓ |
| Non-specific cleavage | ↓ | ↓ | ↓ |

In some embodiments, a wild-type growth factor and variants thereof can be cloned into the pCT vector. In some embodiments, the wild-type growth factor and variants thereof can be expressed on the surface of S. cerevisiae yeast cells as a fusion to the Aga2p mating protein. In some embodiments, successful expression of the wild-type growth factor and variants thereof on the yeast cell surface can be confirmed by detection of the c-myc tag on the C-terminus of the protein. In some embodiments, proper folding of yeast-displayed wild-type growth factor and variants thereof can be confirmed by measuring specific binding activity to wild-type growth factor-Fc.

In some embodiments, the FGF1 polypeptide of SEQ ID NO:1 was employed as a model for demonstrating the setup of the proteolytic stability screen. In some embodiments, the wild type FGF1 was cloned into the pCT vector. In some embodiments, this FGF1 polypeptide and FGF1 variants thereof can be expressed on the surface of S. cerevisiae yeast cells as a fusion to the Aga2p mating protein (see, for example, FIG. 3A). In some embodiments, successful expression of FGF1 on the yeast cell surface can be confirmed by detection of the c-myc tag on the C-terminus of the protein (see, for example, FIG. 3B). In some embodiments, proper folding of yeast-displayed FGF can be confirmed by measuring specific binding activity to FGFR1-Fc (see, for example, FIG. 3C).

In some embodiments, serum, trypsin, chymotrypsin, and plasmin can be used for developing a proteolytic stability screen for growth factor variant polypeptides, including for example, an FGF1 variant polypeptides. In some embodiments, these proteases were selected, based on their scientific and biological relevance to for growth factor variant polypeptides, including for example, an FGF1 variant polypeptides. In some embodiments, the suitability of the protease for the screen was determined by its ability to cleave the growth factor at a reasonable rate with minimal non-specific cleavage of the yeast display proteins. In some embodiments, serum can be used for developing a proteolytic stability screen for growth factor variant polypeptides, including for example, an FGF1 variant polypeptides. In some embodiments, trypsin can be used for developing a proteolytic stability screen for growth factor variant polypeptides, including for example, an FGF1 variant polypeptides. In some embodiments, chymotrypsin can be used for developing a proteolytic stability screen for growth factor variant polypeptides, including for example, ad FGF1 variant polypeptides. In some embodiments, plasmin can be used for developing a proteolytic stability screen for growth factor variant polypeptides, including for example, an FGF1 variant polypeptides.

In some embodiments, the stability is determined by comparing proteolytic cleavage of the wild-type growth factor to proteolytic cleavage of the variant growth factor. In some embodiments, the stability is determined by comparing proteolytic cleavage of the wild-type FGF1 to proteolytic cleavage of the FGF1 variant.

In some embodiments, stability of the growth factor variant is increased by at least 5% to at least 95%, as compared to wild-type growth factor. In some embodiments, stability of the growth factor variant is increased by at least 10% to at least 90%, as compared to wild-type growth factor. In some embodiments, stability of the growth factor variant is increased by at least 5% to at least 90%, as compared to wild-type growth factor. In some embodiments, stability of the growth factor variant is increased by at least 5% to at least 85%, as compared to wild-type growth factor. In some embodiments, stability of the growth factor variant is increased by at least 5% to at least 80%, as compared to wild-type growth factor. In some embodiments, stability of the growth factor variant is increased by at least 5% to at least 75%, as compared to wild-type growth factor. In some embodiments, stability of the growth factor variant is increased by at least 5% to at least 70%, as compared to wild-type growth factor. In some embodiments, stability of the growth factor variant is increased by at least 10% to at least 70%, as compared to wild-type growth factor. In some embodiments, stability of the growth factor variant is increased by at least 5%, as compared to wild-type growth factor. In some embodiments, stability of the growth factor variant is increased by at least 10%, as compared to wild-type growth factor. In some embodiments, stability of the growth factor variant is increased by at least 15%, as compared to wild-type growth factor. In some embodiments, stability of the growth factor variant is increased by at least 20%, as compared to wild-type growth factor. In some embodiments, stability of the growth factor variant is increased by at least 25%, as compared to wild-type growth factor. In some embodiments, stability of the growth factor variant is increased by at least 30%, as compared to wild-type growth factor. In some embodiments, stability of the growth factor variant is increased by at least 35%, as compared to wild-type growth factor. In some embodiments, stability of the growth factor variant is increased by at least 40%, as compared to wild-type growth factor. In some embodiments, stability of the growth factor variant is increased by at least 45%, as compared to wild-type growth factor. In some embodiments, stability of the growth factor variant is increased by at least 50%, as compared to wild-type growth factor. In some embodiments, stability of the growth factor variant is increased by at least 5%, as compared to wild-type growth factor. In some embodiments, stability of the growth factor variant is increased by at least 60%, as compared to wild-type growth factor. In some embodiments, stability of the growth factor variant is increased by at least 65%, as compared to wild-type growth factor. In some embodiments, stability of the growth factor variant is increased by at least 70%, as compared to wild-type growth factor. In some embodiments, stability of the growth factor variant is increased by at least 75%, as compared to wild-type growth factor. In some embodiments, stability of the growth factor variant is increased by at least 80%, as compared to wild-type growth factor. In some embodiments, stability of the growth factor variant is increased by at least 85%, as compared to wild-type growth factor. In some embodiments, stability of the growth factor variant is increased by at least 90%, as compared to wild-type growth factor. In some embodiments, stability of the growth factor variant is increased by at least 95%, as compared to wild-type growth factor.

In some embodiments, stability of the FGF1 variant is increased by at least 5% to at least 95%, as compared to wild-type FGF1. In some embodiments, stability of the FGF1 variant is increased by at least 10% to at least 90%, as compared to wild-type FGF1. In some embodiments, stability of the FGF1 variant is increased by at least 5% to at least 90%, as compared to wild-type FGF1. In some embodiments, stability of the FGF1 variant is increased by at least 5% to at least 85%, as compared to wild-type FGF1. In some embodiments, stability of the FGF1 variant is increased by at least 5% to at least 80%, as compared to wild-type FGF1. In some embodiments, stability of the FGF1 variant is increased by at least 5% to at least 75%, as compared to wild-type FGF1. In some embodiments, stability of the FGF1 variant is increased by at least 5% to at least 70%, as compared to wild-type FGF1. In some embodiments, stability of the FGF1 variant is increased by at least 10% to at least 70%, as compared to wild-type FGF1. In some embodiments, stability of the FGF1 variant is increased by at least 5%, as compared to wild-type FGF1. In some embodiments, stability of the FGF1 variant is increased by at least 10%, as compared to wild-type FGF1. In some embodiments, stability of the FGF1 variant is increased by at least 15%, as compared to wild-type FGF1. In some embodiments, stability of the FGF1 variant is increased by at least 20%, as compared to wild-type FGF1. In some embodiments, stability of the FGF1 variant is increased by at least 25%, as compared to wild-type FGF1. In some embodiments, stability of the FGF1 variant is increased by at least 30%, as compared to wild-type FGF1. In some embodiments, stability of the FGF1 variant is increased by at least 35%, as compared to wild-type FGF1. In some embodiments, stability of the FGF1 variant is increased by at least 40%, as compared to wild-type FGF1. In some embodiments, stability of the FGF1 variant is increased by at least 45%, as compared to wild-type FGF1. In some embodiments, stability of the FGF1 variant is increased by at least 50%, as compared to wild-type FGF1. In some embodiments, stability of the FGF1 variant is increased by at least 5%, as compared to wild-type FGF1. In some embodiments, stability of the FGF1 variant is increased by at least 60%, as compared to wild-type FGF1. In some embodiments, stability of the FGF1 variant is increased by at least 65%, as compared to wild-type FGF1. In some embodiments, stability of the FGF1 variant is increased by at least 70%, as compared to wild-type FGF1. In some embodiments, stability of the FGF1 variant is increased by at least 75%, as compared to wild-type FGF1. In some embodiments, stability of the FGF1 variant is increased by at least 80%, as compared to wild-type FGF1. In some embodiments, stability of the FGF1 variant is increased by at least 85%, as compared to wild-type FGF1. In some embodiments, stability of the FGF1 variant is increased by at least 90%, as compared to wild-type FGF1. In some embodiments, stability of the FGF1 variant is increased by at least 95%, as compared to wild-type FGF1.

In some embodiments, stability of the growth factor variant is increased by at least 1-fold to at least 10-fold, as compared to wild-type growth factor. In some embodiments, stability of the growth factor variant is increased by at least 1-fold, as compared to wild-type growth factor. In some embodiments, stability of the growth factor variant is increased by at least 2-fold, as compared to wild-type growth factor. In some embodiments, stability of the growth factor variant is increased by at least 3-fold, as compared to wild-type growth factor. In some embodiments, stability of
the growth factor variant is increased by at least 4-fold, as
compared to wild-type growth factor. In some embodiments,
stability of the growth factor variant is increased by at least
5-fold, as compared to wild-type growth factor. In some
embodiments, stability of the growth factor variant is
increased by at least 6-fold, as compared to wild-type
growth factor. In some embodiments, stability of the growth
factor variant is increased by at least 7-fold, as compared to
wild-type growth factor. In some embodiments, stability of
the growth factor variant is increased by at least 8-fold, as
compared to wild-type growth factor. In some embodiments,
stability of the growth factor variant is increased by at least
9-fold, as compared to wild-type growth factor. In some
embodiments, stability of the growth factor variant is
increased by at least 10-fold, as compared to wild-type
growth factor.

In some embodiments, stability of the FGF1 variant is
increased by at least 1-fold to at least 10-fold, as compared
to wild-type FGF1. In some embodiments, stability of the
FGF1 variant is increased by at least 1-fold, as compared to
wild-type FGF1. In some embodiments, stability of the
FGF1 variant is increased by at least 2-fold, as compared to
wild-type FGF1. In some embodiments, stability of the
FGF1 variant is increased by at least 3-fold, as compared to
wild-type FGF1. In some embodiments, stability of the
FGF1 variant is increased by at least 4-fold, as compared to
wild-type FGF1. In some embodiments, stability of the
FGF1 variant is increased by at least 5-fold, as compared to
wild-type FGF1. In some embodiments, stability of the
FGF1 variant is increased by at least 6-fold, as compared to
wild-type FGF1. In some embodiments, stability of the
FGF1 variant is increased by at least 7-fold, as compared to
wild-type FGF1. In some embodiments, stability of the
FGF1 variant is increased by at least 8-fold, as compared to
wild-type FGF1. In some embodiments, stability of the
FGF1 variant is increased by at least 9-fold, as compared to
wild-type FGF1. In some embodiments, stability of the
FGF1 variant is increased by at least 10-fold, as compared
to wild-type FGF1.

b. Fluorescent Cell Sorting

In some embodiments, screening can include the use of a
cell sorter. Commercially available flow cytometers can
measure fluorescence emissions at the single-cell level at
four or more wavelengths, at a rate of approximately 50,000
cells per second (Ashcroft and Lopez, 2000). Typical flow
cytometry data can be shown in which yeast have been
labeled with two different color fluorescent probes to mea-
sure protein expression levels and bound soluble ligand (for
example, a growth factor receptor). A "diagonal" population
of cells results due to variation in protein expression levels
on a per cell basis: cells that express more protein will bind
more ligand. The equilibrium binding constant ($K_D$) can be
determined by titration of soluble ligand, and the dissocia-
tion rate constant ($k_{off}$) can be measured through competition
binding of unlabeled ligand. With yeast, a monodispersity of
tethered proteins exists over the cell surface, and soluble
ligand are used for binding and testing, such that avidity
effects are not observed, unlike other display methods using
immobilized ligands. To date, the properties of most proteins
expressed on the yeast cell surface mimic what is seen in
solution in terms of stability and binding affinity (Bader et
al., 2000; Feldhaus et al., 2003; Holler et al., 2000; VanAn-
twerp and Wittrup, 2000). See, also, Weaver-Feldhaus et al.,
"Directed evolution for the development of conformation-
specific affinity reagents using yeast display," Protein Engi-
neering Design and Selection Sep. 26, 2005 18(11):527-536.

Cell sorting can be carried out on a FACS Vantage (BD
Biosciences) multiparameter laser flow cytometer and cell
sorter. Before sorting, fluorescent staining was carried out as
described above, so that analysis of various polypeptide
levels were detected, as described above.

VII. Methods a. Chemical Synthesis

Polypeptide variants of the invention may be prepared
using conventional step-wise solution or solid phase syn-
thesis (see, e.g., Chemical Approaches to the Synthesis of
Peptides and Proteins, Williams et al., Eds., 1997, CRC
Press, Boca Raton Florida, and references cited therein;
Solid Phase Peptide Synthesis: A Practical Approach, Ather-
ton & Sheppard, Eds., 1989, IRL Press, Oxford, England,
and references cited therein).

Alternatively, the peptides of the invention may be pre-
pared by way of segment condensation, as described, for
example, in Liu et al., 1996, Tetrahedron Lett. 37(7)933 936;
Baca, et al., 1995, J. Am. Chem. Soc. 117:1881-1887; Tam
et al., 1995, Int. J. Peptide Protein Res. 45:209-216;
Schnölzer and Kent, 1992, Science 256:221-225; Liu and
Tam, 1994, J. Am. Chem. Soc. 116(10):4149-4153; Liu and
Tam, 1994, Proc. Natl. Acad. Sci. USA 91:6584-6588;
Yamashiro and Li, 1988, Int. J. Peptide Protein Res. 31:322-
334). Segment condensation is a particularly useful method
for synthesizing embodiments containing internal glycine
residues. Other methods useful for synthesizing the peptides
of the invention are described in Nakagawa et al., 1985, J.
Am. Chem. Soc. 107:7087-7092.

Polypeptide variants containing N- and/or C-terminal
blocking groups can be prepared using standard techniques
of organic chemistry. For example, methods for acylating
the N-terminus of a peptide or amidating or esterifying the
C-terminus of a peptide are well-known in the art. Modes of
carrying other modifications at the N- and/or C-terminus
will be apparent to those of skill in the art, as will modes of
protecting any side-chain functionalities as may be neces-
sary to attach terminal blocking groups. Pharmaceutically
acceptable salts (counter ions) can be conveniently prepared
by ion-exchange chromatography or other methods as are
well known in the art.

Compounds of the invention which are in the form of
tandem multimers can be conveniently synthesized by add-
ing the linker(s) to the peptide chain at the appropriate step
in the synthesis. Alternatively, the helical segments can be
synthesized and each segment reacted with the linker. Of
course, the actual method of synthesis will depend on the
composition of the linker. Suitable protecting schemes and
chemistries are well known, and will be apparent to those of
skill in the art.

Compounds of the invention which are in the form of
branched networks can be conveniently synthesized using
the trimeric and tetrameric resins and chemistries described
in Tam, 1988, Proc. Natl. Acad. Sci. USA 85:5409-5413 and
Demoor et al., 1996, Eur. J. Biochem. 239:74-84. Modifying
the synthetic resins and strategies to synthesize branched
networks of higher or lower order, or which contain com-
binations of different core peptide helical segments, is well
within the capabilities of those of skill in the art of peptide
chemistry and/or organic chemistry. Formation of disulfide
linkages, if desired, is generally conducted in the presence of
mild oxidizing agents.

Chemical oxidizing agents may be used, or the com-
pounds may simply be exposed to atmospheric oxygen to
effect these linkages. Various methods are known in the art, including those described, for example, by Tam et al., 1979, Synthesis 955-957; Stewart et al., 1984, Solid Phase Peptide Synthesis, 2d Ed., Pierce Chemical Company Rockford, IL; Ahmed et al., 1975, J. Biol. Chem. 250:8477-8482; and Pennington et al., 1991 Peptides 1990 164-166, Giralt and Andreu, Eds., ESCOM Leiden, The Netherlands. An additional alternative is described by Kamber et al., 1980, Helv. Chim. Acta 63:899-915. A method conducted on solid supports is described by Albericio, 1985, Int. J. Peptide Protein Res. 26:92-97. Any of these methods may be used to form disulfide linkages in the peptides of the invention.

VIII. Acquisition of Polypeptide Coding Sequences a. General Recombinant Technology The creation of variant and/or mutant polypeptides, which incorporate an 0-linked glycosylation sequence of the invention can be accomplished by altering the amino acid sequence of a corresponding parent polypeptide, by either mutation or by full chemical synthesis of the polypeptide. The polypeptide amino acid sequence is preferably altered through changes at the DNA level, particularly by mutating the DNA sequence encoding the polypeptide at preselected bases to generate codons that will translate into the desired amino acids. The DNA mutation(s) are preferably made using methods known in the art.

This invention relies on routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

Nucleic acid sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Entire genes can also be chemically synthesized. Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of the cloned wild-type polypeptide genes, polynucleotide encoding mutant polypeptides, and synthetic oligonucleotides can be verified after cloning using, e.g., the chain termination method for sequencing double-stranded templates of Wallace et al., *Gene* 16: 21-26 (1981).

In an exemplary embodiment, the glycosylation sequence is added by shuffling polynucleotides. Polynucleotides encoding a candidate polypeptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA*

91:10747-10751 (1994); Stemmer, *Nature* 370:389-391 (1994); and U.S. Pat. Nos. 5,605,793, 5,837,458, 5,830,721 and 5,811,238.

b. Cloning and Subcloning of a Wild-Type Peptide Coding Sequence

Numerous polynucleotide sequences encoding wild-type polypeptides have been determined and are available from a commercial supplier, e.g., human growth hormone, e.g., GenBank Accession Nos. NM 000515, NM 002059, NM 022556, NM 022557, NM 022558, NM 022559, NM 022560, NM 022561, and NM 022562.

The rapid progress in the studies of human genome has made possible a cloning approach where a human DNA sequence database can be searched for any gene segment that has a certain percentage of sequence homology to a known nucleotide sequence, such as one encoding a previously identified polypeptide. Any DNA sequence so identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a nucleic acid sequence encoding a polypeptide can be isolated from a human cDNA or genomic DNA library using standard cloning techniques such as polymerase chain reaction (PCR), where homology-based primers can often be derived from a known nucleic acid sequence encoding a polypeptide. Most commonly used techniques for this purpose are described in standard texts, e.g., Sambrook and Russell, supra.

cDNA libraries suitable for obtaining a coding sequence for a wild-type polypeptide may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene,* 25: 263-269 (1983); Ausubel et al., *supra*). Upon obtaining an amplified segment of nucleotide sequence by PCR, the segment can be further used as a probe to isolate the full-length polynucleotide sequence encoding the wild-type polypeptide from the cDNA library. A general description of appropriate procedures can be found in Sambrook and Russell, *supra*.

A similar procedure can be followed to obtain a full length sequence encoding a wild-type polypeptide, e.g., any one of the GenBank Accession Nos mentioned above, from a human genomic library. Human genomic libraries are commercially available or can be constructed according to various art-recognized methods. In general, to construct a genomic library, the DNA is first extracted from an tissue where a polypeptide is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization as described in Benton and Davis, *Science,* 196: 180-182 (1977). Colony hybridization is carried out as described by Grunstein et al., *Proc. Natl. Acad. Sci. USA,* 72: 3961-3965 (1975).

Based on sequence homology, degenerate oligonucleotides can be designed as primer sets and PCR can be performed under suitable conditions (see, e.g., White et al., *PCR Protocols: Current Methods and Applications,* 1993;

Griffin and Griffin, *PCR Technology, CRC Press Inc.* 1994) to amplify a segment of nucleotide sequence from a cDNA or genomic library. Using the amplified segment as a probe, the full-length nucleic acid encoding a wild-type polypeptide is obtained.

Upon acquiring a nucleic acid sequence encoding a wild-type polypeptide, the coding sequence can be subcloned into a vector, for instance, an expression vector, so that a recombinant wild-type polypeptide can be produced from the resulting construct. Further modifications to the wild-type polypeptide coding sequence, e.g., nucleotide substitutions, may be subsequently made to alter the characteristics of the molecule.

c. Introducing Mutations into a Polypeptide Sequence

From an encoding polynucleotide sequence, the amino acid sequence of a wild-type polypeptide can be determined. Subsequently, this amino acid sequence may be modified to alter the protein's glycosylation pattern, by introducing additional glycosylation sequence(s) at various locations in the amino acid sequence.

A variety of mutation-generating protocols are established and described in the art. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science,* 229: 1193-1201 (1985)), mutagenesis using uracil-containing templates (Kunkel, *Proc. Natl. Acad. Sci. USA,* 82: 488-492 (1985)), oligonucleotide-directed mutagenesis (Zoller and Smith, *Nucl. Acids Res.,* 10: 6487-6500 (1982)), phosphorothioate-modified DNA mutagenesis (Taylor et al., *Nucl. Acids Res.,* 13: 8749-8764 and 8765-8787 (1985)), and mutagenesis using gapped duplex DNA (Kramer et al., *Nucl. Acids Res.,* 12: 9441-9456 (1984)).

Other methods for generating mutations include point mismatch repair (Kramer et al., *Cell,* 38: 879-887 (1984)), mutagenesis using repair-deficient host strains (Carter et al., *Nucl. Acids Res.,* 13: 4431-4443 (1985)), deletion mutagenesis (Eghtedarzadeh and Henikoff, *Nucl. Acids Res.,* 14: 5115 (1986)), restriction-selection and restriction-purification (Wells et al., *Phil. Trans. R. Soc. Lond. A,* 317: 415-423 (1986)), mutagenesis by total gene synthesis (Nambiar et al., *Science,* 223: 1299-1301 (1984)), double-strand break repair (Mandecki, *Proc. Natl. Acad. Sci. USA,* 83: 7177-7181 (1986)), mutagenesis by polynucleotide chain termination methods (U.S. Pat. No. 5,965,408), and error-prone PCR (Leung et al., *Biotechniques,* 1: 11-15 (1989)).

d. Modification of Nucleic Acids for Preferred Codon Usage in a Host Organism

The polynucleotide sequence encoding a polypeptide variant can be further altered to coincide with the preferred codon usage of a particular host. For example, the preferred codon usage of one strain of bacterial cells can be used to derive a polynucleotide that encodes a polypeptide variant of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell. U.S. Pat. No. 5,824,864, for example, provides the frequency of codon usage by highly expressed genes exhibited by dicotyledonous plants and monocotyledonous plants.

At the completion of modification, the polypeptide variant coding sequences are verified by sequencing and are then subcloned into an appropriate expression vector for recombinant production in the same manner as the wild-type polypeptides.

IX. Expression of Mutant Polypeptides

Following sequence verification, the polypeptide variant of the present invention can be produced using routine techniques in the field of recombinant genetics, relying on the polynucleotide sequences encoding the polypeptide disclosed herein.

a. Expression Systems

To obtain high-level expression of a nucleic acid encoding a mutant polypeptide of the present invention, one typically subclones a polynucleotide encoding the mutant polypeptide into an expression vector that contains a strong promoter to direct transcription, a transcription/translation terminator and a ribosome binding site for translational initiation. Suitable bacterial promoters are well known in the art and described, e.g., in Sambrook and Russell, *supra,* and Ausubel et al., *supra.* Bacterial expression systems for expressing the wild-type or mutant polypeptide are available in, e.g., *E. coli, Bacillus* sp., *Salmonella,* and *Caulobacter.* Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the mutant polypeptide in host cells. A typical expression cassette thus contains a promoter operably linked to the nucleic acid sequence encoding the mutant polypeptide and signals required for efficient polyadenylation of the transcript, ribosome binding sites, and translation termination. The nucleic acid sequence encoding the polypeptide is typically linked to a cleavable signal peptide sequence to promote secretion of the polypeptide by the transformed cell. Such signal peptides include, among others, the signal peptides from tissue plasminogen activator, insulin, and neuron growth factor, and juvenile hormone esterase of *Heliothis virescens.* Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical.

Any of the conventional vectors used for expression in eukaryotic or prokaryotic cells may be used. Standard bacterial expression vectors include plasmids such as pBR322-based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A⁺, pMTO10/A⁺, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

In some exemplary embodiments the expression vector is chosen from pCWin1, pCWin2, pCWin2/MBP, pCWin2-MBP-SBD (pMS$_{39}$), and pCWin2-MBP-MCS-SBD (pMXS$_{39}$) as disclosed in co-owned U.S. Patent application filed Apr. 9, 2004 which is incorporated herein by reference.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the mutant polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

The prokaryotic sequences are optionally chosen such that they do not interfere with the replication of the DNA in eukaryotic cells, if necessary.

When periplasmic expression of a recombinant protein (e.g., a hgh mutant of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

As discussed above, a person skilled in the art will recognize that various conservative substitutions can be made to any wild-type or mutant polypeptide or its coding sequence while still retaining the biological activity of the polypeptide. Moreover, modifications of a polynucleotide coding sequence may also be made to accommodate preferred codon usage in a particular expression host without altering the resulting amino acid sequence.

b. Transfection Methods

Standard transfection methods are used to produce bacterial, mammalian, yeast or insect cell lines that express large quantities of the mutant polypeptide, which are then purified using standard techniques (see, e.g., Colley et al., *J Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, *supra*). It is only necessary that the particular genetic engineering procedure used be capable of successfully introducing at least one gene into the host cell capable of expressing the mutant polypeptide.

c. Detection of Expression of Mutant Polypeptides in Host Cells

After the expression vector is introduced into appropriate host cells, the transfected cells are cultured under conditions favoring expression of the mutant polypeptide. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., *supra*; and Sambrook and Russell, *supra*).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, *supra*). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a mutant polypeptide in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a mutant polypeptide of the present invention (e.g., Harlow and Lane, *Antibodies, A Laboratory Manual*, Chapter 14, Cold Spring Harbor, 1988; Kohler and Milstein, *Nature,* 256: 495-497 (1975)). Such techniques require antibody preparation by selecting antibodies with high specificity against the mutant polypeptide or an antigenic portion thereof. The methods of raising polyclonal and monoclonal antibodies are well established and their descriptions can be found in the literature, see, e.g., Harlow and Lane, *supra*; Kohler and Milstein, *Eur. J Immunol.,* 6: 511-519 (1976). More detailed descriptions of preparing antibody against the mutant polypeptide of the present invention and conducting immunological assays detecting the mutant polypeptide are provided in a later section.

X. Purification of Recombinantly Produced Mutant
Polypeptides

Once the expression of a recombinant mutant polypeptide in transfected host cells is confirmed, the host cells are then cultured in an appropriate scale for the purpose of purifying the recombinant polypeptide.

a. Purification from Bacteria

When the mutant polypeptides of the present invention are produced recombinantly by transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.10% Nonidet P40, a non-ionic detergent. The cell suspension can be ground using a Polytron grinder (Brinkman Instruments, Westbury, NY). Alternatively, the cells can be sonicated on ice. Alternate methods of lysing bacteria are described in Ausubel et al. and Sambrook and Russell, both *supra*, and will be apparent to those of skill in the art. For further description of purifying recombinant polypeptides from bacterial inclusion body, see, e.g., Patra et al., *Protein Expression and Purification* 18: 182-190 (2000).

The recombinant proteins present in the supernatant can be separated from the host proteins by standard separation techniques well known to those of skill in the art.

b. Immunoassays for Detection of Mutant Polypeptide Expression

To confirm the production of a recombinant mutant polypeptide, immunological assays may be useful to detect in a sample the expression of the polypeptide. Immunological assays are also useful for quantifying the expression level of the recombinant hormone. Antibodies against a mutant polypeptide are necessary for carrying out these immunological assays.

c. Production of Antibodies against Mutant Polypeptides

Methods for producing polyclonal and monoclonal antibodies that react specifically with an immunogen of interest are known to those of skill in the art (see, e.g., Coligan, *Current Protocols in Immunology* Wiley/Greene, NY, 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, CA, and references cited therein; Goding, *Monoclonal Antibodies: Principles and Practice* (2d ed.) Academic Press, New York, NY, 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

In order to produce antisera containing antibodies with desired specificity, the polypeptide of interest (e.g., a mutant polypeptide of the present invention) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, *supra*, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., *supra*. The general principles and methods of recombinant polypeptide production discussed above are applicable for antibody production by recombinant methods.

When desired, antibodies capable of specifically recognizing a mutant polypeptide of the present invention can be tested for their cross-reactivity against the wild-type polypeptide and thus distinguished from the antibodies against the wild-type protein. For instance, antisera obtained from an animal immunized with a mutant polypeptide can be run through a column on which a wild-type polypeptide is immobilized. The portion of the antisera that passes through the column recognizes only the mutant polypeptide and not the wild-type polypeptide. Similarly, monoclonal antibodies against a mutant polypeptide can also be screened for their exclusivity in recognizing only the mutant but not the wild-type polypeptide.

Polyclonal or monoclonal antibodies that specifically recognize only the mutant polypeptide of the present invention but not the wild-type polypeptide are useful for isolating the mutant protein from the wild-type protein, for example, by incubating a sample with a mutant peptide-specific polyclonal or monoclonal antibody immobilized on a solid support.

XI. Methods of Treatment and Diagnosis

In various embodiments, the invention provides a method of preventing, ameliorating or treating a disease state. In these embodiments, the invention provides a method that comprises administering to a subject in need thereof an amount of a polypeptide variant of the invention sufficient to prevent, ameliorate or treat the disease state. An exemplary disease state is cancer. The disclosed agonist variants can be useful for the promotion of cell growth, particularly for angiogenesis, and the treatment of cardiovascular, hepatic, musculoskeletal and neuronal diseases. For example, certain polypeptide variants of the invention are useful in the prevention or treatment of hyperproliferative diseases or disorders, e.g., various forms of cancer.

In an exemplary embodiment, the invention provides a method of treating cancer in a subject in need of such treatment. The method includes administering to the subject a therapeutically effective amount of a polypeptide variant of the invention.

It is contemplated that the polypeptide variants of the invention can be used in the treatment of a variety of FGF responsive disorders, including, for example, various eye disorders, FGF responsive tumor cells in lung cancer, breast cancer, colon cancer, prostate cancer, ovarian cancer, head and neck cancer, ovarian cancer, multiple myeloma, liver cancer, gastric cancer, esophageal cancer, kidney cancer, nasopharangeal cancer, pancreatic cancer, mesothelioma, melanoma and glioblastoma.

In exemplary embodiments, the cancer is a carcinoma, e.g., colorectal, squamous cell, hepatocellular, renal, breast or lung.

The polypeptide variants can be used to inhibit or reduce the proliferation of tumor cells. In such an approach, the tumor cells are exposed to a therapeutically effective amount of the polypeptide variant so as to inhibit or reduce proliferation of the tumor cell. In certain embodiments, the polypeptide variants inhibit tumor cell proliferation by at least 50%, 60%, 70%, 80%, 90%, 95% or 100%.

In certain embodiments, the polypeptide variant is used to inhibit or reduce proliferation of a tumor cell wherein the variant reduces the ability of FGF1 to bind to FGFR. In certain embodiments, the FGF1 polypeptide variant is used to inhibit or promote wound healing.

In addition, the polypeptide variant can be used to inhibit, or slow down tumor growth or development in a mammal. In such a method, an effective amount of the polypeptide variant is administered to the mammal so as to inhibit or slow down tumor growth in the mammal. Accordingly, the polypeptide variants can be used to treat tumors, for example, in a mammal. The method comprises administering to the mammal a therapeutically effective amount of the polypeptide variant. The polypeptide variant can be administered alone or in combination with another pharmaceutically active molecule, so as to treat the tumor.

Generally, a therapeutically effective amount of polypeptide variant will be in the range of from about 0.1 mg/kg to about 100 mg/kg, optionally from about 1 mg/kg to about 100 mg/kg, optionally from about 1 mg/kg to 10 mg/kg. The amount administered will depend on variables such as the type and extent of disease or indication to be treated, the overall health status of the particular patient, the relative biological efficacy of the polypeptide variant delivered, the formulation of the polypeptide variant, the presence and types of excipients in the formulation, and the route of administration. The initial dosage administered may be increased beyond the upper level in order to rapidly achieve the desired blood-level or tissue level, or the initial dosage may be smaller than the optimum and the daily dosage may be progressively increased during the course of treatment depending on the particular situation. Human dosage can be optimized, e.g., in a conventional Phase I dose escalation study designed to run from 0.5 mg/kg to 20 mg/kg. Dosing frequency can vary, depending on factors such as route of administration, dosage amount and the disease condition being treated. Exemplary dosing frequencies are once per day, once per week and once every two weeks. A preferred route of administration is parenteral, e.g., intravenous infusion. Formulation of protein-based drugs is within ordinary skill in the art. In some embodiments of the invention, the polypeptide variant, e.g., protein-based, is lyophilized and reconstituted in buffered saline at the time of administration.

The polypeptide variants may be administered either alone or in combination with other pharmaceutically active ingredients. The other active ingredients, e.g., immunomodulators, can be administered together with the polypeptide variant, or can be administered before or after the polypeptide variant.

Formulations containing the polypeptide variants for therapeutic use, typically include the polypeptide variants combined with a pharmaceutically acceptable carrier. As used herein, "pharmaceutically acceptable carrier" means buffers, carriers, and excipients, that are, within the scope of sound medical judgment, suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers, in this regard, are intended to include any and all buffers, solvents, dispersion media, coatings, isotonic and absorption delaying agents, and the like, compatible with pharmaceutical administration. The use of such media and agents for pharmaceutically active substances is known in the art.

The formulations can be conveniently presented in a dosage unit form and can be prepared by any suitable method, including any of the methods well known in the pharmacy art. Remington's Pharmaceutical Sciences, 18th ed. (Mack Publishing Company, 1990).

In exemplary embodiments, the polypeptide variants are used for diagnostic purposes, either in vitro or in vivo, the polypeptide variants typically are labeled either directly or indirectly with a detectable moiety. The detectable moiety can be any moiety which is capable of producing, either directly or indirectly, a detectable signal. For example, the detectable moiety may be a radioisotope, such as $^{3}$H, $^{14}$C, $^{32}$P $^{35}$S, or $^{125}$I; a fluorescent or chemiluminescent compound, such as fluorescein isothiocyanate, Cy5.5 (GE Healthcare), Alexa Fluro® dyes (Invitrogen), IRDye® infrared dyes (LI-COR® Biosciences), rhodamine, or luciferin; an enzyme, such as alkaline phosphatase, beta-galactosidase, or horseradish peroxidase; a spin probe, such as a spin label; or a colored particle, for example, a latex or gold particle. It is understood that the polypeptide variant can be conjugated to the detectable moiety using a number of approaches known in the art, for example, as described in Hunter et al. (1962) Nature 144: 945; David et al. (1974) Biochemistry 13: 1014; Pain et al. (1981) J. Immunol Meth 40: 219; and Nygren (1982) J. Histochem and Cytochem. 30: 407. The labels may be detected, e.g., visually or with the aid of a spectrophotometer or other detector or other appropriate imaging system.

The polypeptide variants can be employed in a wide range of immunoassay techniques available in the art. Exemplary immunoassays include, for example, sandwich immunoassays, competitive immunoassays, immunohistochemical procedures.

In a sandwich immunoassay, two antibodies that bind an analyte or antigen of interest are used, e.g., one immobilized onto a solid support, and one free in solution and labeled with a detectable moiety. When a sample containing the antigen is introduced into this system, the antigen binds to both the immobilized antibody and the labeled antibody, to form a "sandwich" immune complex on the surface of the support. The complexed protein is detected by washing away non-bound sample components and excess labeled antibody, and measuring the amount of labeled antibody complexed to protein on the support's surface. Alternatively, the antibody free in solution can be detected by a third antibody labeled with a detectable moiety which binds the free antibody. A detailed review of immunological assay design, theory and protocols can be found in numerous texts, including Butt, ed., (1984) Practical Immunology, Marcel Dekker, New York; Harlow et al. eds. (1988) *Antibodies, A Laboratory Approach*, Cold Spring Harbor Laboratory; and Diamandis et al., eds. (1996) Immunoassay, Academic Press, Boston.

It is contemplated that the labeled polypeptide variants are useful as in vivo imaging agents, whereby the polypeptide variants can target the imaging agents to particular tissues of interest in the recipient. A remotely detectable moiety for in vivo imaging includes the radioactive atom $^{99}$mTc, a gamma emitter with a half-life of about six hours. Non-limiting examples of radionuclide diagnostic agents include, for example $^{110}$In, $_{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb, $^{83}$Sr, or other γ-, β-, or positron-emitters.

Non-radioactive moieties also useful in in vivo imaging include nitroxide spin labels as well as lanthanide and transition metal ions all of which induce proton relaxation in situ. In addition to imaging the complexed radioactive moieties may be used in standard radioimmunotherapy protocols to destroy the targeted cell.

A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

The disclosed polypeptide variants may also be labeled with a fluorescent marker so as to allow detection in vivo. In some embodiments, the fluorescent label is Cy5.5 (GE Healthcare). In other embodiments, the fluorescent label is an Alexa Fluro® dye (Invitrogen). In some embodiments, the fluorescent label is an IRDye® infrared dye (LI-COR® Biosciences).

Exemplary nucleotides for high dose radiotherapy include the radioactive atoms $^{90}$Yt, $^{131}$I and $^{111}$In. The polypeptide variant can be labeled with $^{131}$I, $^{111}$In and $^{99}$mTC using coupling techniques known in the imaging arts. Similarly, procedures for preparing and administering the imaging agent as well as capturing and processing images are well known in the imaging art and so are not discussed in detail herein. Similarly, methods for performing antibody-based immunotherapies are well known in the art. See, for example, U.S. Pat. No. 5,534,254.

EXAMPLES

Example 1: A High-Throughput Screening Method for Engineering Proteolytically Stable Growth Factors Abstract Growth factors are an important class of regulatory proteins which have great potential to be developed as therapeutic molecules for regenerative medicine and cancer treatment. However, the activity and efficacy of growth factors as therapeutic molecules are greatly limited by their poor thermal and proteolytic stability. While numerous methods have been developed to engineer growth factors with increased thermal stability, there has been a lack of focus and methods development for engineering growth factors with increased proteolytic stability. Proteases such as plasmin, elastase, uPA, cathepsins, and MMPs play critical roles in extracellular matrix degradation and signal transduction, particularly in wound healing and tumor formation. These proteases have been reported to commonly degrade growth factors as well. In this work, we describe a generalizable method for engineering growth factors for increased proteolytic stability. We utilize the yeast display platform and FACS screening as a combinatorial approach to selecting for mutants with increased proteolytic stability. This method was validated by demonstrating the ability of the screen to differentiate between wild type FGF1 and a proteolytically stable FGF1 mutant reported in literature.

Introduction

This example describes a combinatorial approach to engineering proteolytically stable growth factors using the yeast display platform and flow-activated cell sorting (FACS) for screening. The process of setting up the screening method using FGF1 as a model example is demonstrated. The screen was set up for FGF1 because of its extremely poor thermal and proteolytic stability[14,21]. Wild type growth factors with the poorest stability have the greatest need for engineering stable versions for use in therapeutics. Thus, it was important for us to demonstrate the utility of the method for engineering growth factors.by selecting a model growth factor that was poorly stable. In this example, the use of serum or several different proteases as the selective pressure for screening was explored. Finally, the ability of the screen to differentiate between FGF variants of different proteolytic stabilities was validated. In Example 2, the capability of the combinatorial screen through the engineering and characterization of a proteolytically stable FGF1 mutant is exhibited.

Results

Workflow of the combinatorial screening method for engineering proteolytically stable proteins The yeast display platform, which is commonly used to engineer high affinity binders, is also utilized to engineer proteins with greater proteolytic stability (FIG. 1). Several thousand copies of a single growth factor variant are displayed on the surface of yeast as tethered fusions. The hemagglutinin (HA) tag is expressed upstream of the growth factor while the c-myc tag is expressed downstream of the growth factor. Cells can be incubated with soluble Fc fusions of the corresponding receptor, which can bind to the yeast displayed growth factor.

The yeast display platform is combined with flow-activated cell sorting (FACS) to engineer growth factors with higher proteolytic stability (FIG. 2). A library of growth factor mutants is generated by random mutagenesis, directed mutagenesis, or DNA shuffling. The library of yeast cells is incubated with a protease of interest, during which cleavage of the yeast surface displayed proteins occurs. Growth factor mutants with greater proteolytic stability are more resistant to cleavage on the yeast cell surface. After protease incubation, the cells are washed and incubated with soluble Fc fusions of the functional receptor that bind to properly folded growth factor mutants with retained receptor binding affinity. FACS is used to sort for properly folded, uncleaved growth factor mutants, which are expanded and induced for the next round of sorting.

Fluorescent antibody markers against the Fc domain, the c-myc domain, and the HA tag are used to measure receptor binding, growth factor-specific cleavage, and non-specific cleavage (Table 2.1). Detection of the bound Fc-fusion receptor is important to ensure that mutations in the growth factor do not severely reduce the binding affinity for the receptor or lead to improper protein folding. Growth factor-specific cleavage is a direct measure of a growth factor's proteolytic stability. It is detected by the c-myc signal, as a cleaved growth factor will have the C-terminal c-myc tag removed. Non-specific cleavage occurs when the protease cleaves within the yeast surface display proteins Aga1p and Aga2p. During non-specific cleavage, the fluorescent signals for all three markers are decreased. This is undesirable, as the dynamic range for detecting growth factor cleavage and binding activity are decreased. Thus, the HA signal is used to ensure that non-specific cleavage by the protease of interest is minimal.

Yeast Display of FGF1

Figures 3A, 3B, 3C:
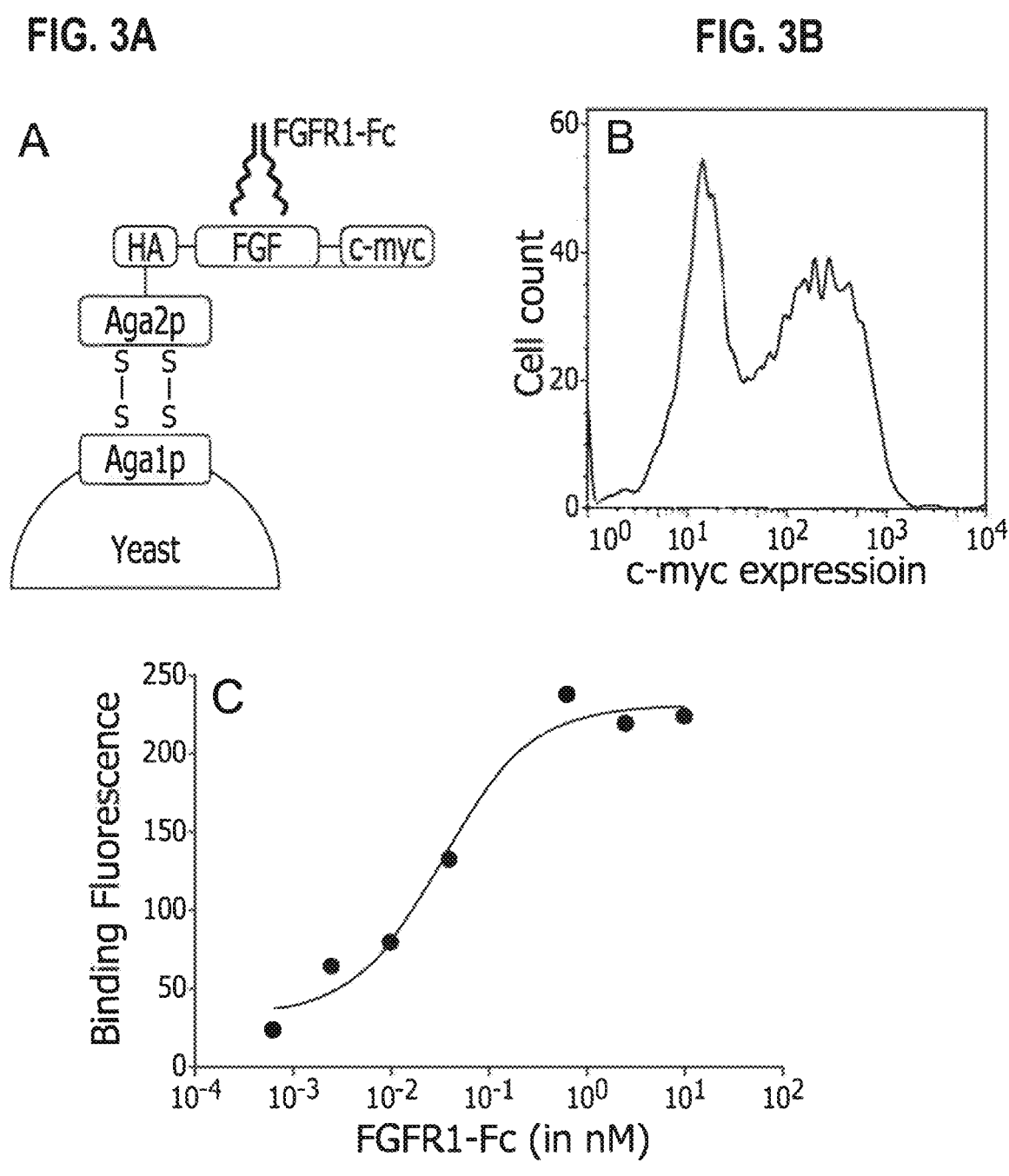
FIG. 3A-FIG. 3C Yeast display of FGF1. (A) FGF1 is expressed as a fusion to adhesion protein agglutinin Aga2p, which is attached by two disulfide bonds to the cell wall protein Aga1p. FGFR1-Fc is the corresponding soluble receptor that binds to FGF1. (B) Fluorescent labeling of the c-myc tag shows that FGF1 is successfully expressed on the surface of yeast. (C) Fc fusion of FGFR1 shows specific binding to yeast-displayed FGF1. Yeast expressing surface-displayed FGF1 were incubated with soluble FGFR1-Fc for 3 hours at various concentrations. Cells were washed and stained with anti-Fc AlexaFluor488 for soluble FGFR1-Fc. Fluorescence associated with binding to yeast cells were measured by flow cytometry and plotted.

FGF1 was chosen as a model for demonstrating the setup of the proteolytic stability screen. Wild-type FGF1 was cloned into the pCT vector, to be expressed on the surface of *S. cerevisiae* yeast cells as a fusion to the Aga2p mating protein (FIG. 3A). Successful expression of FGF1 on the yeast cell surface was confirmed by detection of the c-myc tag on the C-terminus of the protein (FIG. 3B). Finally, we confirmed proper folding of yeast-displayed FGF by measuring specific binding activity to FGFR1-Fc (FIG. 3C).

Selection of protease for engineering proteolytically stable FGF1

We tested the use of serum, trypsin, chymotrypsin, and plasmin for developing a proteolytic stability screen for FGF1. These proteases were selected, based on their scientific and biological relevance to FGF1. The suitability of the protease for the screen was determined by its ability to cleave the growth factor at a reasonable rate with minimal non-specific cleavage of the yeast display proteins.

Figure 4:
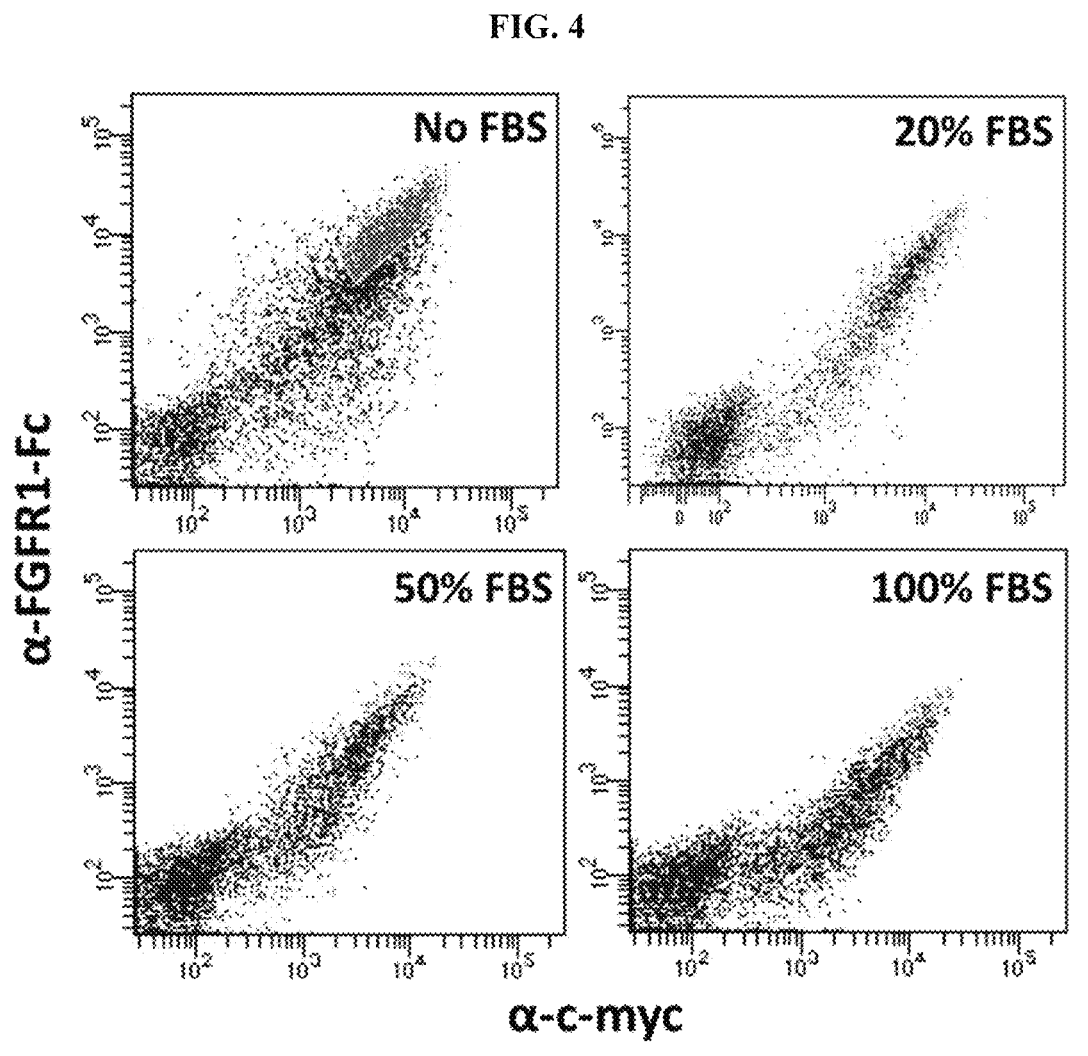

We first attempted to develop the screen using serum, a natural blood product consisting of numerous proteases that might be encountered by growth factors in the body[22-24]. We incubated a library of FGF1 mutants with various concentrations of fetal bovine serum (FBS) to see if we could observe FGF1 cleavage and a decrease in FGFR1-Fc binding signal (FIG. 4). We found that even when the concentration of FBS was increased to 100%, we only observed a minimal decrease in the FGF1 cleavage signal ($\alpha$-c-myc) and the FGFR1-Fc binding signal. Thus, we concluded that serum did not provide sufficiently stringent selective pressure to cleave yeast-displayed FGF1 mutants with low proteolytic stability.

Figure 5:
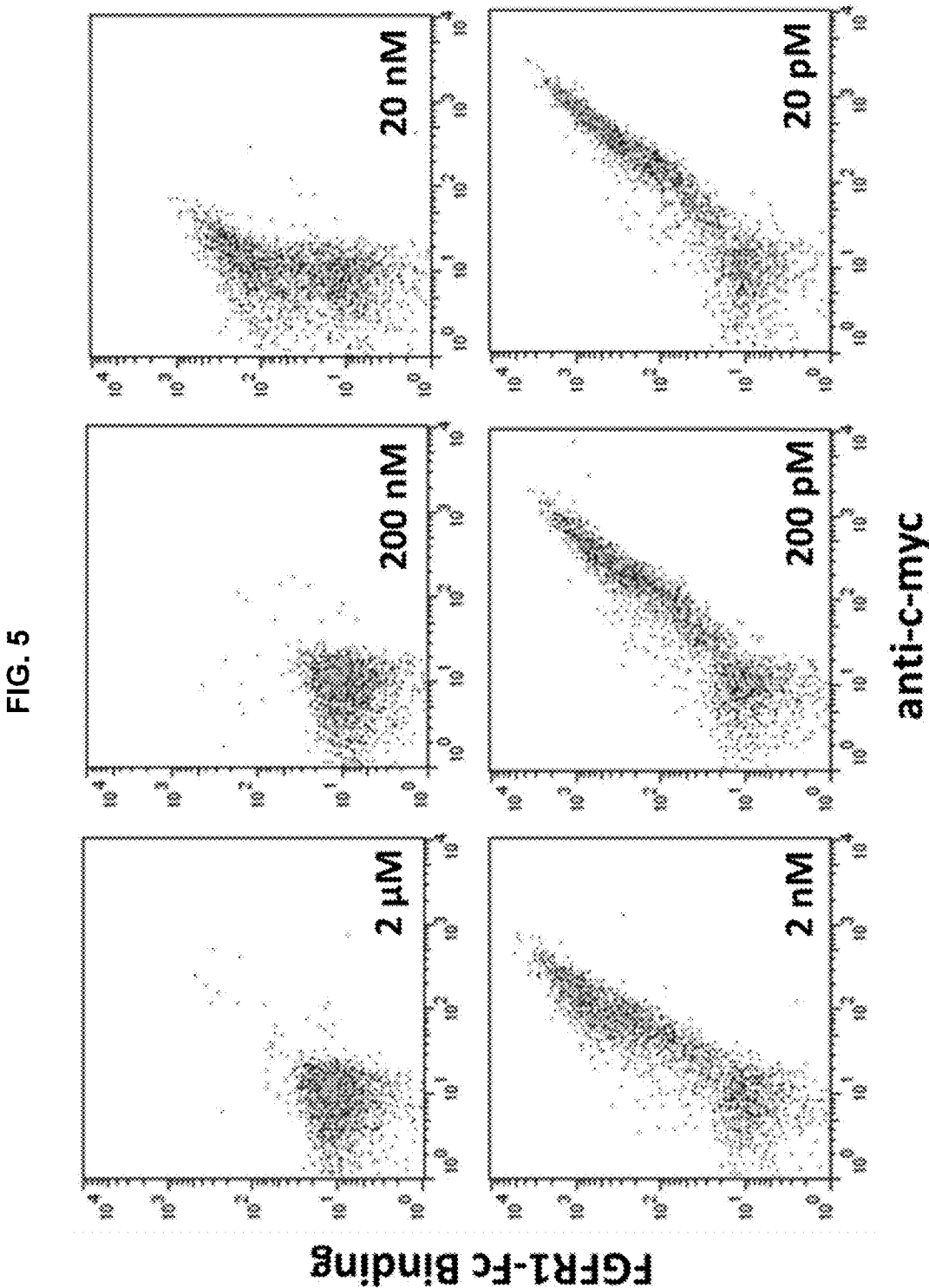
FIG. 5 Proteolytic stability assay with trypsin. Yeast cells displaying FGF1 were incubated with different concentrations of trypsin. After washing cells and incubation with 10 nM FGFR1-Fc, cells were stained with fluorescent antibodies for c-myc and the Fc domain of the soluble receptor. Analysis by flow cytometry shows that increasing the concentration of trypsin leads to cleavage of the yeast displayed proteins (decreased c-myc) and loss of binding to FGFR1-Fc.
Figure 6:
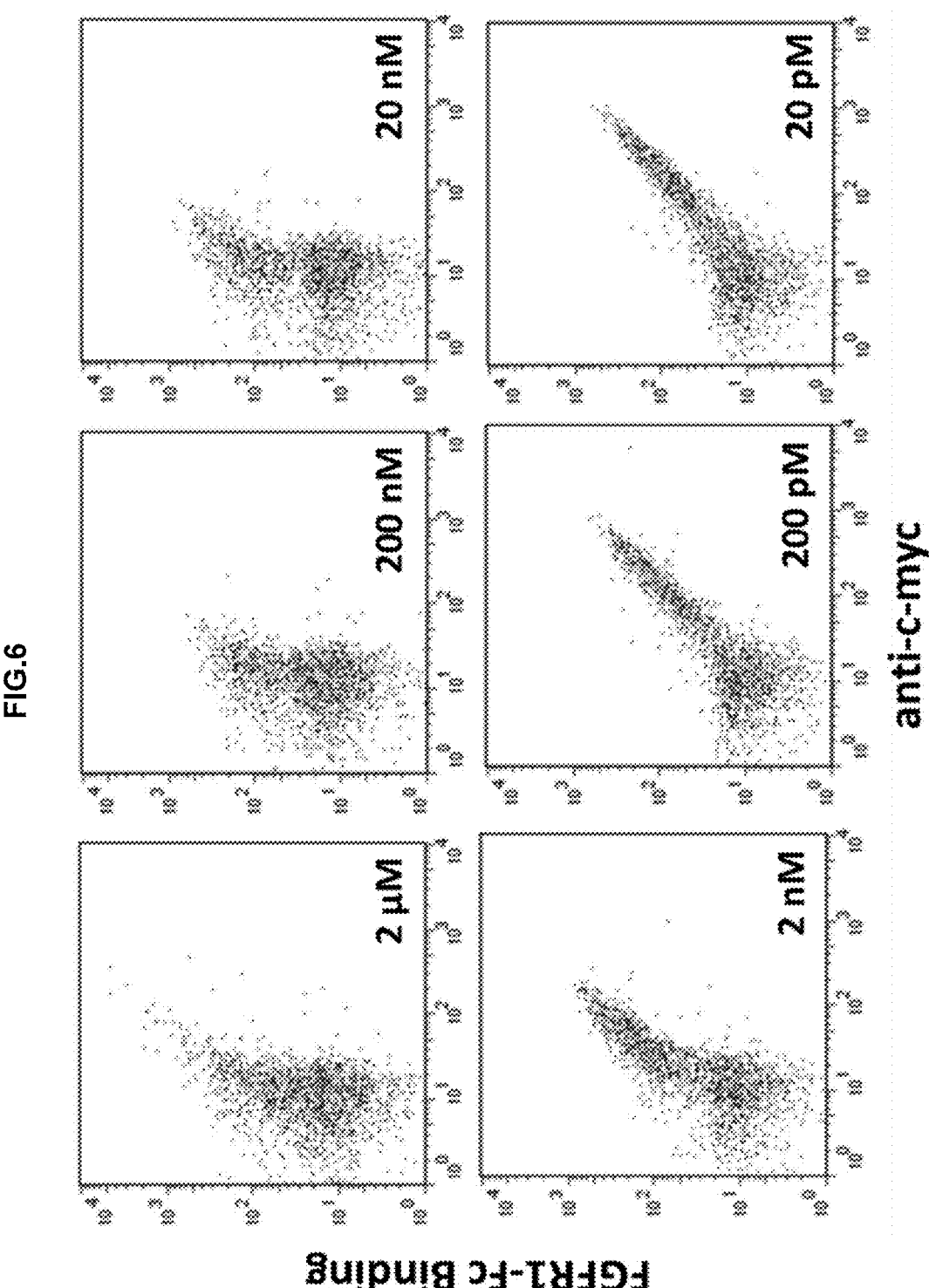
FIG. 6 Proteolytic stability assay with chymotrypsin. Yeast cells displaying FGF1 were incubated with different concentrations of chymotrypsin. After washing cells and incubation with 10 nM FGFR1-Fc, cells were stained with fluorescent antibodies for c-myc and the Fc domain of the soluble receptor. Analysis by flow cytometry shows that increasing the concentration of chymotrypsin leads to cleavage of the yeast displayed proteins (decreased c-myc) and loss of binding to FGFR1-Fc.
Figure 7A:
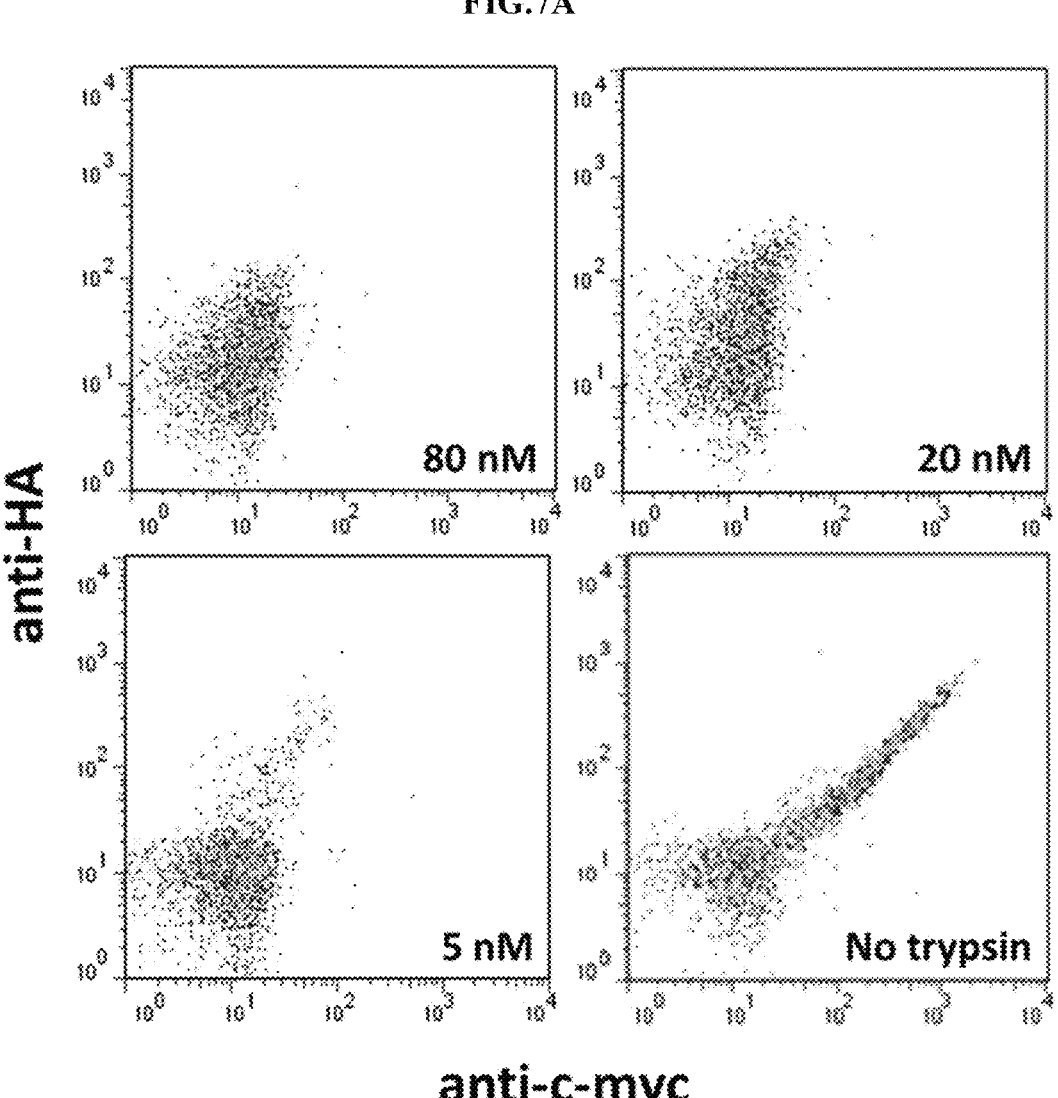
FIG. 7A-FIG. 7B Non-specific cleavage of yeast display proteins Aga1 and Aga2 by trypsin. Yeast cells displaying FGF1 were incubated with different concentrations of trypsin. After washing, cells were stained with fluorescent antibodies for HA and c-myc. Analysis by flow cytometry shows that increasing the concentration of trypsin leads to loss of HA signal, indicating non-specific cleavage of yeast display proteins Aga1 and Aga2.
Figure 7B:
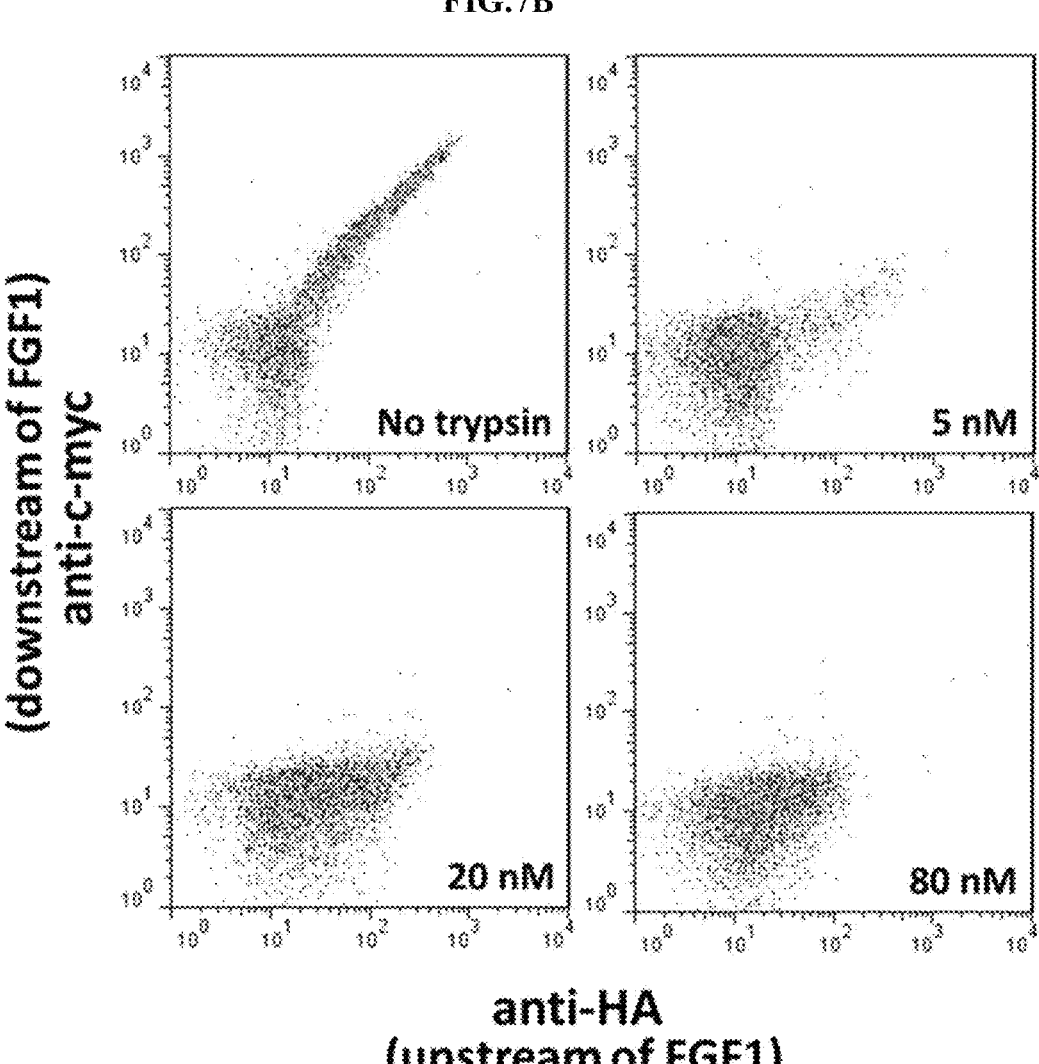
Figure 8A:
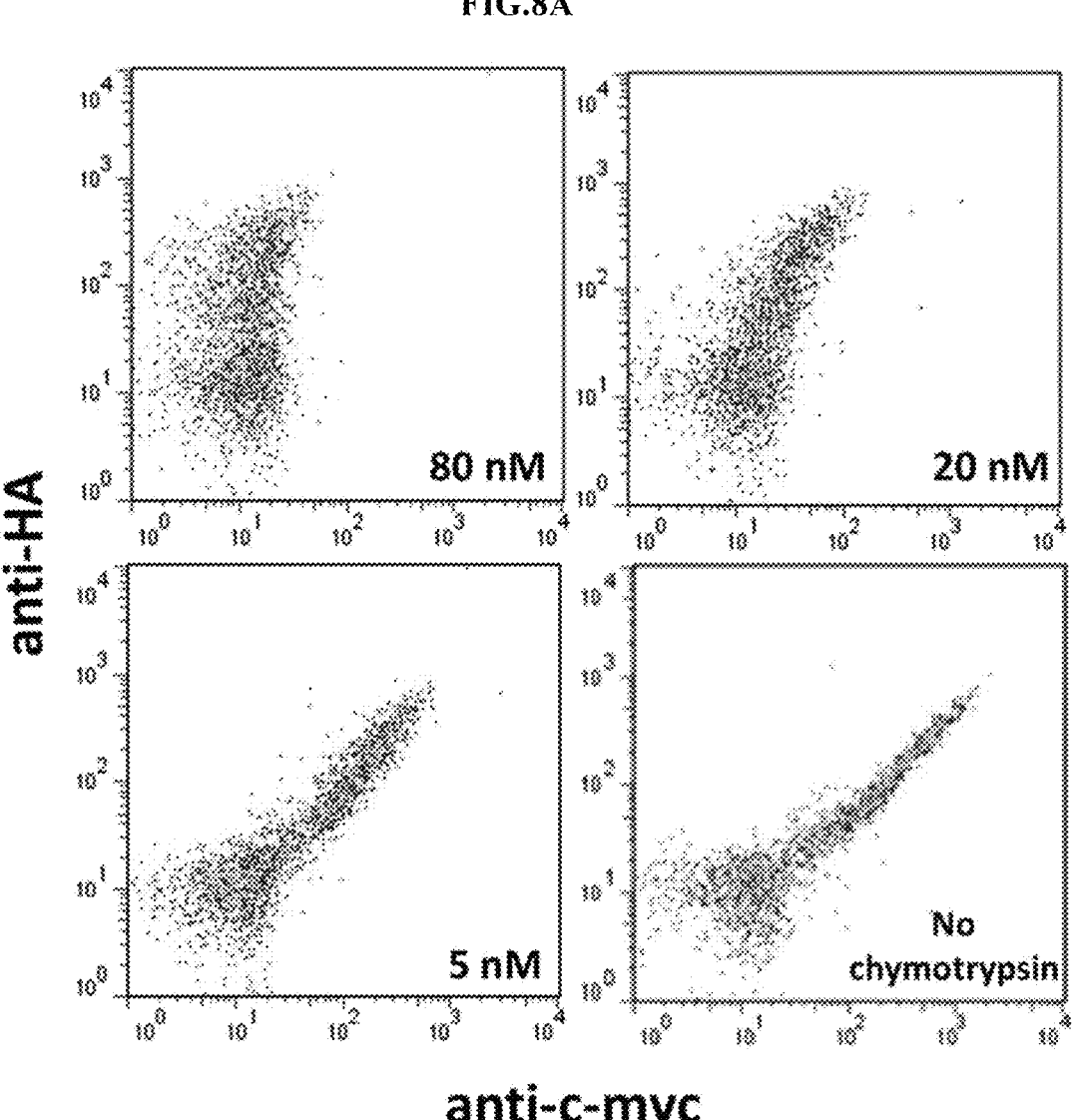
Figure 8B:
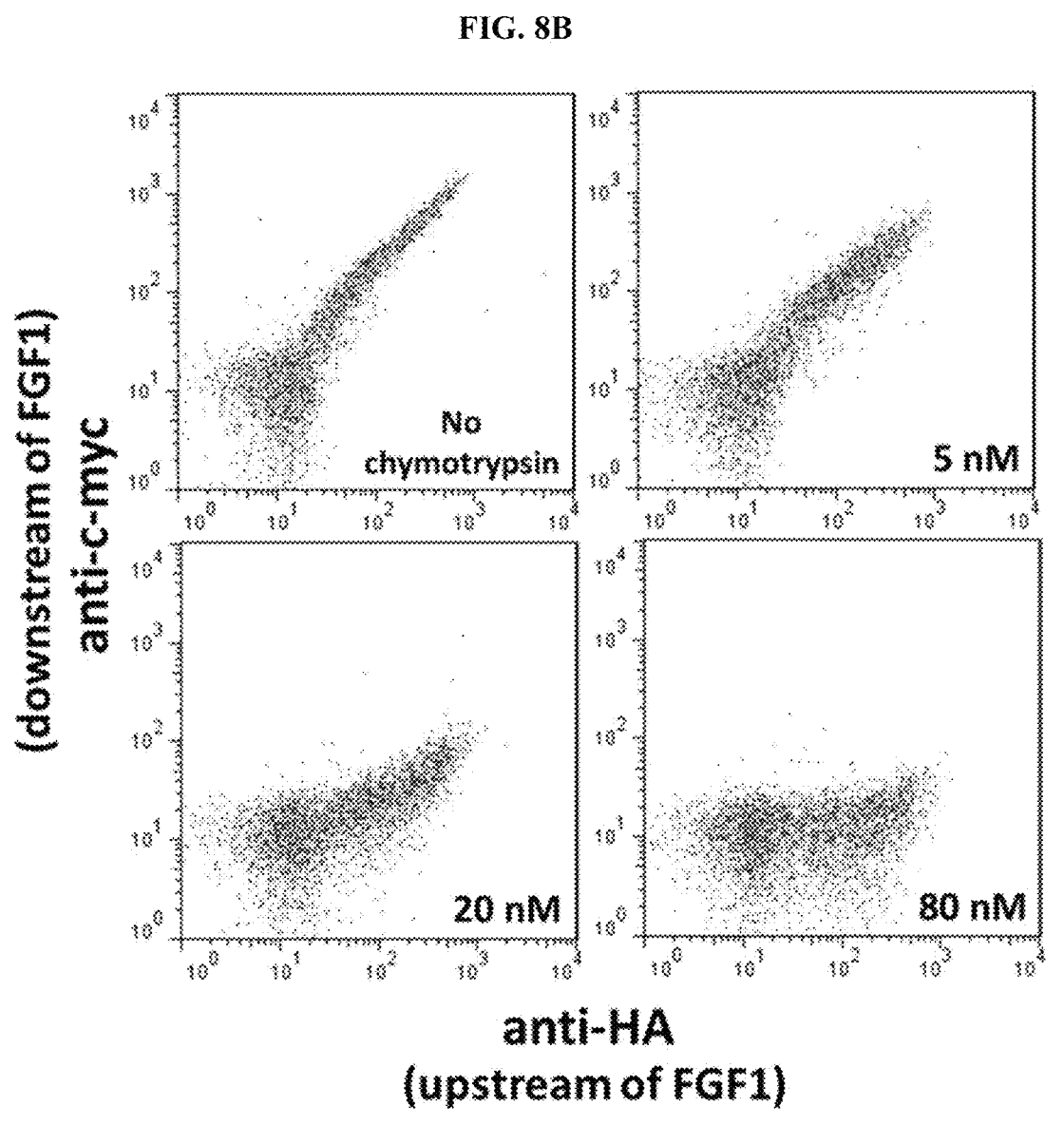

Next, we tested the development of the screen using trypsin and chymotrypsin, two proteases that are commonly used to measure and report the proteolytic stability of proteins. We incubated yeast-displayed wild-type FGF1 with various concentrations of trypsin (FIG. 5) and chymotrypsin (FIG. 6), then measured the extent of protein cleavage ($\alpha$-c-myc) and binding to FGFR1-Fc. We found that both trypsin and chymotrypsin had a concentration-dependent effect on the extent of observed protein cleavage and binding to FGFR1-Fc. We then determined whether the observed protein cleavage was due to non-specific cleavage ($\alpha$-HA) or FGF1-specific cleavage ($\alpha$-c-myc). We found that the HA signal was significantly decreased upon incubation with higher trypsin concentrations, indicating that much of the observed protein cleavage by trypsin was due to non-specific cleavage (FIG. 7). Thus, we concluded that trypsin could not be used for a proteolytic stability screen. Meanwhile, we found that only the c-myc signal decreased while HA signal was relatively unaffected by incubation with higher chymotrypsin concentrations, indicating that the protein cleavage by chymotrypsin was primarily attributable to cleavage within FGF1 (FIG. 8). Thus, we concluded that chymotrypsin was a reasonable candidate for use in the proteolytic stability screen.

Figure 9:
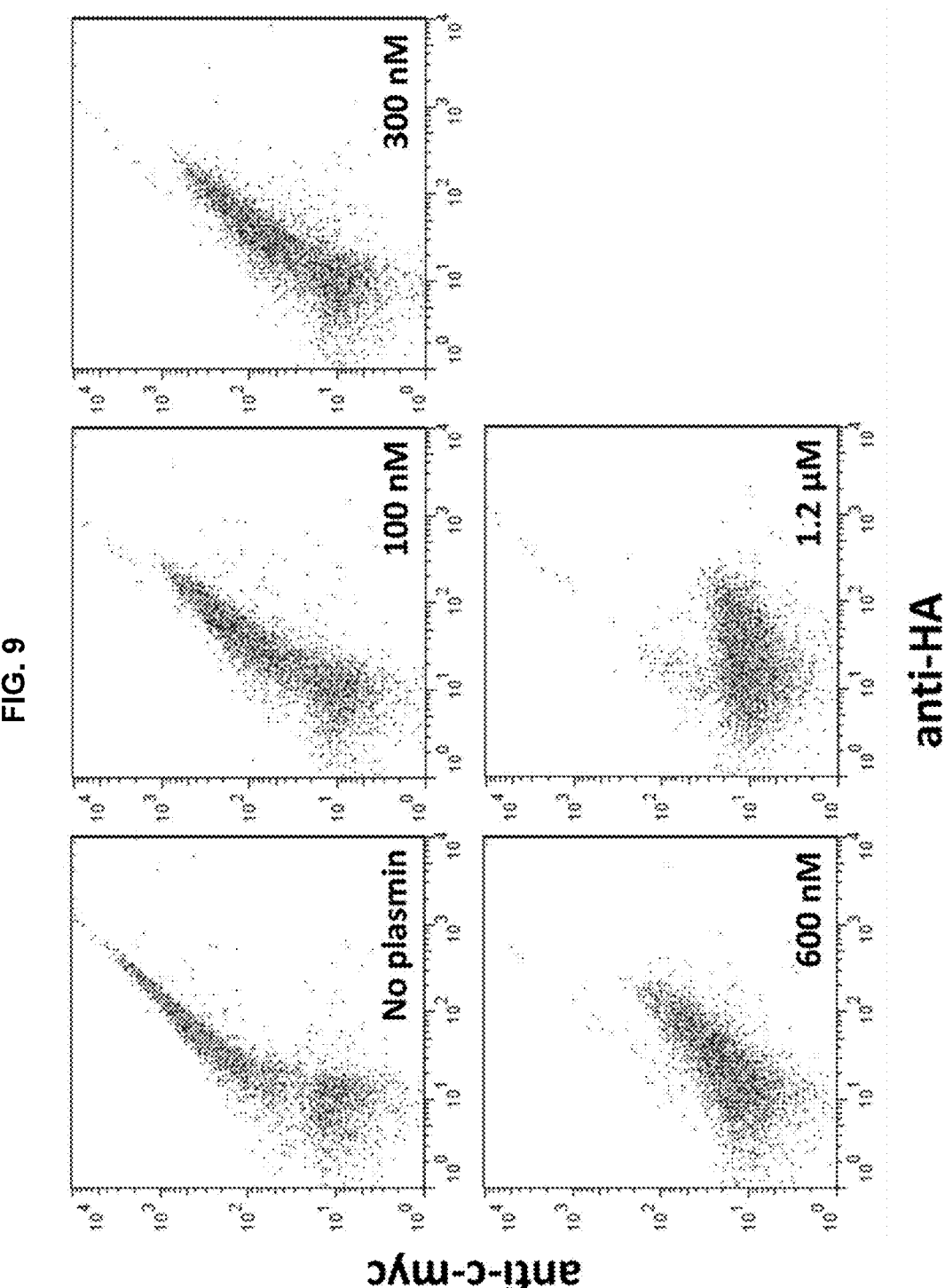
FIG. 9 Proteolytic stability assay with plasmin. Yeast cells displaying FGF1 were incubated with different concentrations of plasmin. After washing, cells were stained with fluorescent antibodies for HA and c-myc. Analysis by flow cytometry shows that there is a concentration-dependent cleavage of FGF1.
Figure 10:
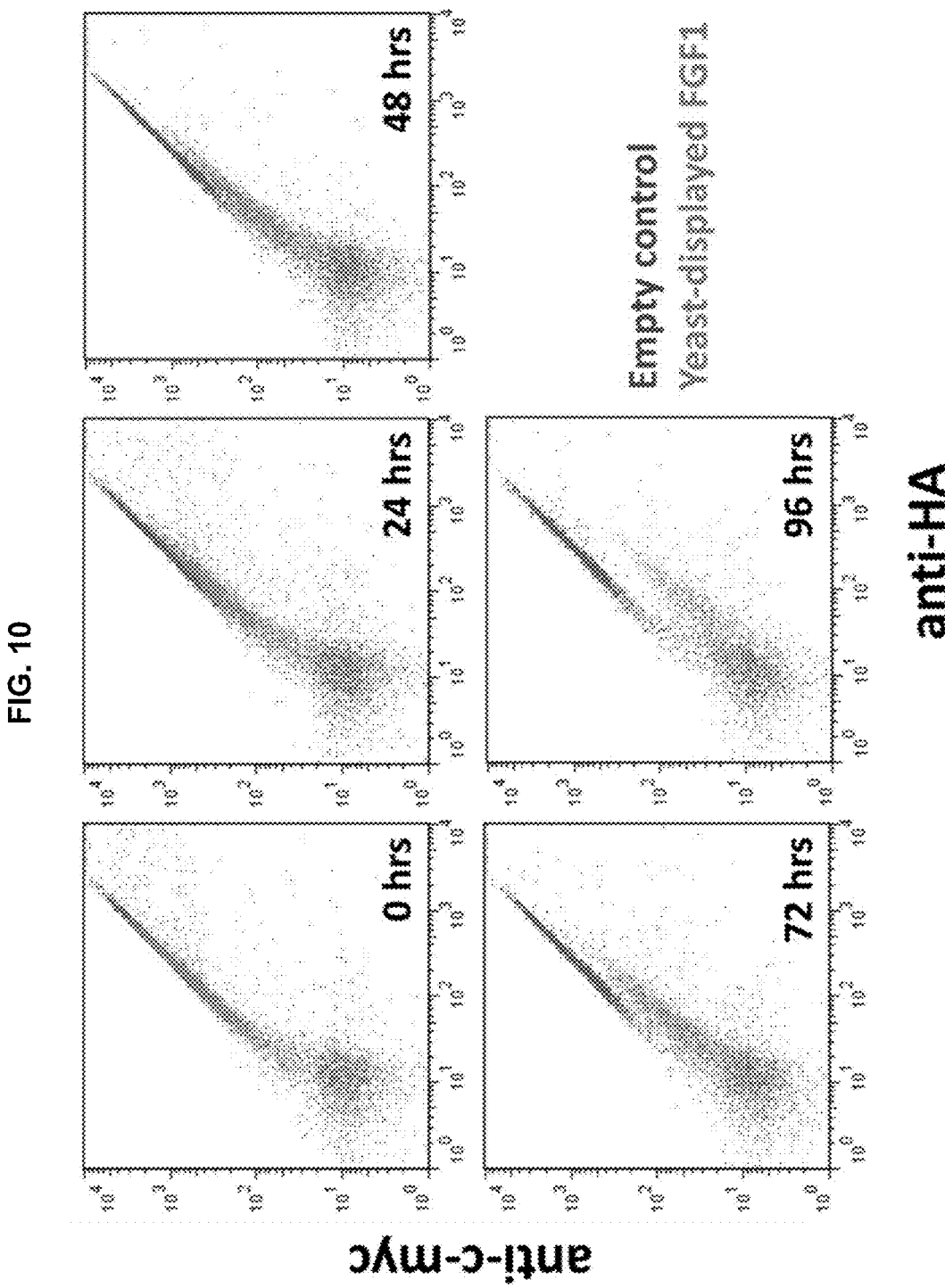
FIG. 10 FGF1-specific cleavage by plasmin. Yeast cells displaying FGF1 and an empty control expressing only the yeast display proteins Aga1 and Aga2 were incubated with 125 nM plasmin. After washing, cells were stained with fluorescent antibodies for HA and c-myc. Analysis by flow cytometry shows that increasing the concentration of plasmin leads to loss of c-myc signal for yeast cells displaying FGF1 but not for yeast cells displaying the empty control. This confirms that cleavage of yeast displayed proteins by plasmin is FGF1-specific.

Finally, we evaluated the development of the proteolytic stability screen using plasmin, a protease that degrades extracellular matrix proteins and that has been reported to degrade FGF1[25]. We incubated yeast-displayed wild-type FGF1 with various concentrations of plasmin and found that yeast-displayed protein was cleaved in a concentration-dependent manner (FIG. 9). To confirmed that the observed cleavage was FGF1-specific, rather than non-specific, we compared the cleavage of yeast-displayed FGF1 to an empty control expressing only the yeast display proteins, Aga1 and Aga2, as well as the HA and c-myc tags (FIG. 10). During incubation with plasmin over the course of 96 hours, we found that yeast-displayed FGF1 was being cleaved while the empty control was not. Thus, we concluded that the observed cleavage was FGF1-specific.

Validation of screening method by differentiating between wild type FGF1 and a proteolytically stable FGF1 mutant To test the ability of a plasmin-based screen to differentiate between FGFs of different proteolytic stabilities, we compared wild type (WT) FGF1 to a thermally stabilized FGF1 mutant (PM2) developed in literature by rational design[14]. PM2 was characterized by Zakrzewska et al. to be more stable in the presence of trypsin. We hypothesized that because plasmin shares primary sequence specificity with trypsin, PM2 would be more resistant to cleavage by plasmin. Thus, we expected that a functional proteolytic stability screening method using plasmin would enable us to observe less FGF1-specific cleavage in PM2 as compared to WT FGF1.

Figure 11:
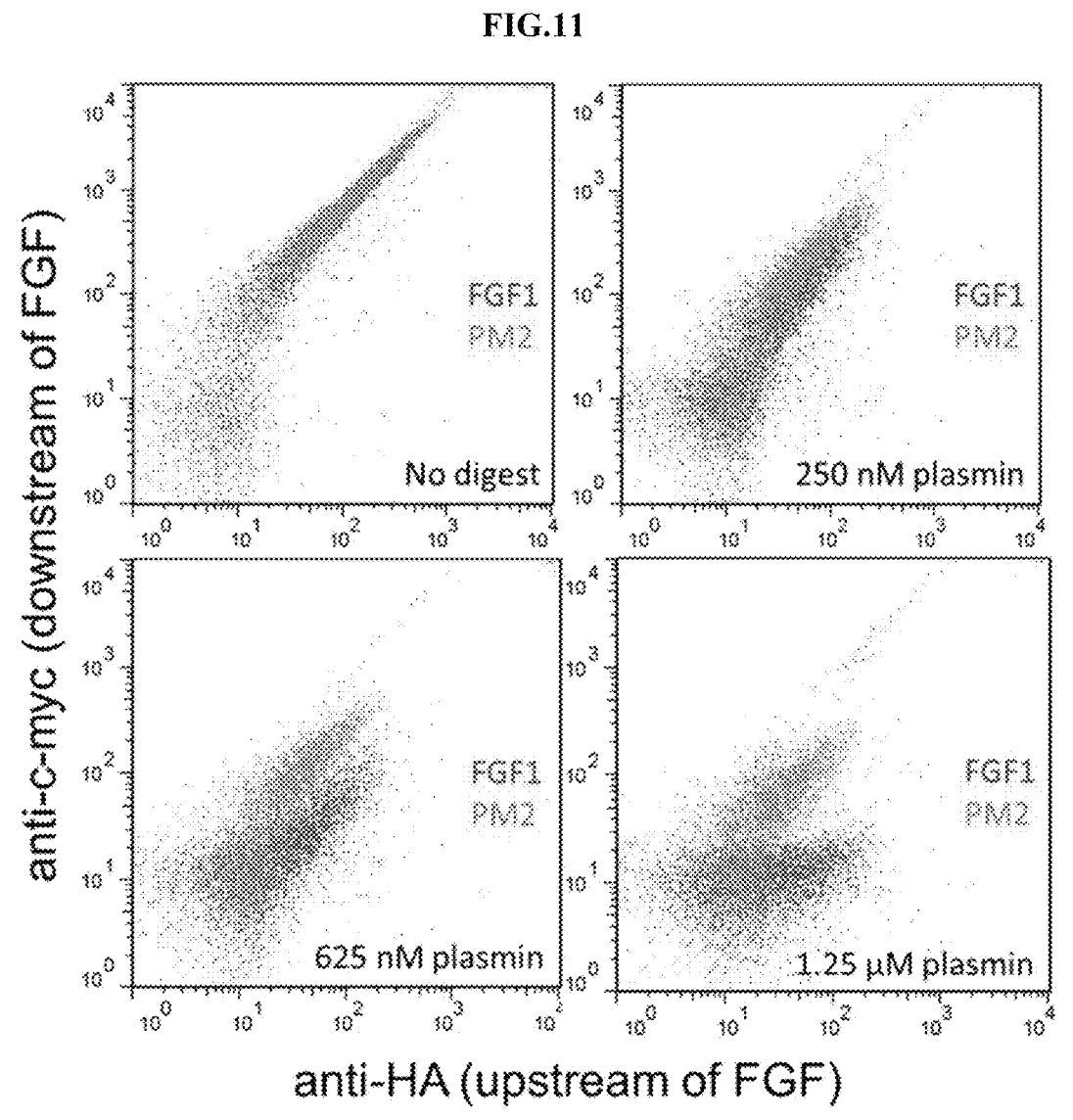

Yeast cells displaying PM2 or WT FGF1 were incubated with varying concentrations of plasmin for 48 hours and stained for non-specific cleavage (anti-HA) and FGF1-specific cleavage (anti-c-myc) (FIG. 11). It was found that clean separation of the populations was obtainable by the difference in c-myc signal, with relatively little effect on the HA signal. This difference in cleavage signal confirmed that using plasmin would enable the screen to properly identify new FGF mutants with greater proteolytic stability, and to sort for these populations by FACS.

Discussion

In this example, describe the development of a high-throughput, generalizable screening method for engineering proteolytically stable growth factors using the yeast display platform and flow-activated cell sorting is described. As an example, the setup of the screen for FGF1, a highly unstable growth factor is provided.

In establishing the screen for a growth factor of interest, the first step is to ensure that the growth factor can be expressed on the surface of yeast and that it is able to bind to a soluble version of its receptor. It was confirmed that FGF1 can be expressed in the pCT vector as a C-terminal fusion to the Aga2 yeast display protein, and that it binds specifically to FGFR1-Fc. In the past, VEGF, EGF, and HGF have successfully been expressed by yeast display[6,26,27]. This suggests that the yeast-display-based proteolytic screening method can be applied more generally to other growth factors as well. If the growth factor cannot be expressed in the pCT vector, the pTMY vector could be used to successfully express the growth factor as a N-terminal fusion to Aga2 instead. In the case of HGF, it could not be expressed in pCT vector, but was successfully expressed in pTMY.

The second step was to determine the protease to be used for the proteolytic screen. We tested the use of serum, trypsin, chymotrypsin, and plasmin for engineering yeast-displayed FGF1. We found that fetal bovine serum (FBS) provided too weak of a selective pressure even at high concentrations. Although proteases are found in FBS, protease inhibitors found in FBS such as α-1-antiproteinase and α-1-antichymotrypsin may cause their activity to be low[28]. Given that FGF1 is a particularly unstable growth factor, it is likely that FBS would not be an appropriate selective proteolytic pressure for engineering other growth factors as well. However, other types of serum with different compositions such as newborn calf serum, adult bovine serum, or human serum could be considered. We tested the use of trypsin and chymotrypsin, which are proteases commonly used to measure proteolytic stability of proteins in literature. This is likely because trypsin and chymotrypsin have high activity and low specificity, which allow them to cleave almost any protein at a certain degradation rate[29]. However, these properties may make them unattractive for use in a proteolytic stability screen. We found that for trypsin, much of the loss in expression (c-myc) signal was due to non-specific cleavage of the yeast display proteins, making trypsin a poor candidate for the proteolytic stability screening of any growth factor. While chymotrypsin did not seem to demonstrate a significant level of non-specific cleavage, it is important to note that the protease is primarily found in the digestive tract and unlikely to be biologically relevant to growth factors in the bloodstream. Finally, we tested the use of plasmin, a protease that is found in virtually all tissues and that has been shown to degrade FGF1[13,25] Plasmin has also been implicated in the degradation of other growth factors, such as VEGF[30] . We found that plasmin was able to cleave yeast displayed FGF1 specifically, with relatively little non-specific cleavage of yeast display proteins. Based on the proteases that we were able to test, we concluded that plasmin would be the most appropriate protease to use as the selective pressure for the screen. Other proteases that are biologically relevant to growth factors, such as elastase, uPA, cathepsins, and MMPs may also be validated by testing for their high growth-factor-specific cleavage and low non-specific cleavage of yeast displayed proteins as described.

The final step in the setup of the screen is to determine whether growth factor mutants with different proteolytic stabilities can be differentiated. This optional step provides an important benchmark that provides confidence in the ability of the screen to select for proteolytically stable mutants. For FGF1, we confirmed that PM2, a FGF1 mutant with increased thermal and proteolytic stability, could be differentiated from wild-type FGF1 when displayed on the surface of yeast. In the absence of available proteolytically stabilized growth factor mutants, the screen could still be performed as long as the protease demonstrates high growth-factor-specific cleavage and low non-specific cleavage of yeast displayed proteins. In Example 2, we report the engineering of FGF1 for proteolytic stability using the method we have developed.

Materials and Methods

Cloning of Yeast Display Constructs

FGF1 was cloned from human FGF1 cDNA (MGC Clone: 9218, IMAGE: 3896359, Residues: Phe16 to Asp155) into pCT vector (restriction sites: NheI, BamHI) for yeast display. For the proteolytically stable FGF1 mutant, PM2, the mutations Q40P (CAA to CCA), S471 (TCC to ATC), and H93G (CAT to GGT) were made to FGF1 using site-directed mutagenesis.

Binding Assay for Yeast-Displayed FGF1

50,000 induced yeast cells were incubated with varying concentrations of human FGFR1 beta (IIIc)-Fc (R&D Systems) in phosphate-buffered saline with 1 g/L BSA (PBSA) at room temperature. Cells were incubated in sufficiently large volumes to avoid ligand depletion and long enough times (typically 3 to 24 hours) to reach equilibrium. During the last 30 minutes of incubation, yeast cells were incubated with 1:2500 dilution of chicken anti-c-Myc (Invitrogen) in PBSA. Yeast were pelleted, washed, then incubated with 1:200 dilution of secondary antibodies on ice for 10 min: anti-Human IgG-FITC (Sigma Aldrich) and anti-chicken-IgY-PE (Santa Cruz Biotechnology) against anti-c-myc. Yeast were washed, pelleted, and resuspended in PBSA immediately before analysis by flow cytometry using EMD Millipore Guava EasyCyte. Flow cytometry data were analyzed using FlowJo (v7.6.1). Binding curves were plotted and $K_d$ values were obtained using GraphPad Prism 6.

Proteolytic Stability Assays for Screening

Fetal bovine serum (Gibco), trypsin from bovine pancreas (Sigma Aldrich), chymotrypsin type VII from bovine pancreas (Sigma Aldrich), or plasmin from human plasma (Sigma Aldrich) was used as the protease or protease mix for incubation. Fetal bovine serum was diluted in Dulbecco's Modified Eagle Medium (Gibco). Trypsin and chymotrypsin were diluted in trypsin buffer (100 mM Tris-HCl (pH 8), 1 mM $CaCl_2$), 1% BSA). Plasmin was diluted in plasmin buffer (100 mM Tris-HCl, 0.01% BSA, pH 8.5).

1 million induced yeast cells were incubated with various concentrations of protease in the appropriate buffers. At the end of incubation, cells were washed once with PBSA (PBS+0.1% BSA) and resuspended in buffer protease inhibitor cocktail (Sigma Aldrich) to quench residual protease activity. After 5 minutes, cells were washed once more with PBSA. For only experiments that measured FGFR binding activity, cells were incubated in 10 nM human FGFR1 beta (IIIc)-Fc (R&D Systems) in pBSA for 1 hour. After the final wash, cells were incubated with appropriate fluorescent antibodies.

For experiments measuring FGFR1 binding activity and c-myc signal, cells were incubated with 1:2000 dilution of chicken anti-c-Myc (Invitrogen) in PBSA for 30 minutes. After washing, cells were then incubated in secondary antibodies for 10 minutes on ice: anti-Human IgG-FITC (Sigma Aldrich) and anti-chicken-IgY-PE (Santa Cruz Biotechnology) against anti-c-myc.

For experiments measuring HA and c-myc signal, cells were incubated with 1:1000 dilution of anti-HA-Tag (6E2) Mouse mAb (Cell Signaling) and 1:2000 dilution of chicken anti-c-Myc (Invitrogen) for 30 minutes. After washing, cells were then incubated in secondary antibodies for 10 minutes on ice: goat anti-mouse-PE (Invitrogen) and goat anti-chicken-IgY-AlexaFluor488 (Santa Cruz Biotechnology).

Yeast were washed, pelleted, and resuspended in PBSA immediately before analysis by flow cytometry using EMD Millipore Guava EasyCyte. Flow cytometry data were analyzed using FlowJo (v7.6.1). Binding curves were plotted and $K_d$ values were obtained using GraphPad Prism 6.

TABLE 3

Effect of different events on the observed
signal from fluorescent antibody markers.

| | HA | c-myc | Fc |
|---|---|---|---|
| Denaturation/loss of binding affinity | | | ↓ |
| Growth factor-specific cleavage | | ↓ | ↓ |
| Non-specific cleavage | ↓ | ↓ | ↓ |

Example 2: Engineering Proteolytically Stabilized Fibroblast Growth Factor

Abstract

FGF1 plays a significant role in cell differentiation and the induction of angiogenesis during wound healing, tissue regeneration, tumor formation, and other angiogenesis-dependent diseases. Thus, agonists and antagonists based on FGF1 can have important applications for cell culture and protein therapeutics. However, FGF1 have been reported to exhibit susceptibility to degradation when exposed to proteases in culture. Its poor proteolytic stability can hinder their activity and efficacy in cell culture or when developed as therapeutic molecules. In this example, FGF1 peptides were engineered for proteolytic stability using the yeast display-based screening method described in Example 1. Gating strategies for selection of proteolytically stable FGFs and successfully identify candidates for characterization were explored.

Introduction

Fibroblast growth factors (FGFs) are part of an important family of growth factors that regulate biological activities including embryonic development, cell differentiation, cell proliferation, cell migration, angiogenesis, metabolism, and wound healing[1,31-35]. Thus, FGF-based therapeutics have been of interest for applications in cancer therapy, wound healing, tissue regeneration, and treatment of metabolic disorders[32,36,37] Of the many FGF family members, FGF1 is of particular interest as one of the most significant FGF ligands known to induce a pro-angiogenic phenotype in endothelial cells by signaling through FGFR1 and FGFR2[38].

FGF1 has been reported to protect functional vessels from regression, to induce arterial growth, and to promote capillary proliferation[39,40]. It was found to induce tube formation in human umbilical vascular endothelial cells (HUVECs) and the formation of blood vessels in Matrigel plug assays[41].

Despite the potency of FGF1 in the induction of angiogenesis for wound healing and tissue regeneration, efforts to utilize FGF1 as a therapeutic agent have been largely unsuccessful. Gene therapy in the form of an injectable intramuscular plasmid encoding FGF1 was shown in Phase I and II clinical studies to improve perfusion and reduce the need for amputation in patients with end-stage lower-extremity ischemia[42,43]. However, it failed to show clinical efficacy in Phase III clinical studies for the reduction of amputation or mortality in patients with critical limb ischemia[44]. CardioVascular BioTherapeutics has also developed a recombinant wild-type FGF1 (CVBT-141) for the treatment of ulcers, coronary heart disease, and peripheral arterial disease, but clinical trials have remained unsuccessful for almost two decades[45].

The failure of recombinant FGF1 to be effective in many clinical applications likely stems, in part, from its poor stability. Wild type FGF1 is rapidly degraded upon incubation at 37° C. in conditioned media or in culture, with a degradation half-life of approximately 25 minutes[14,21]. It has specifically been shown that plasmin, a key protease found in areas of wound healing, can degrade both FGF1 and FGF2[25,46,47]

This example describes the engineering of FGF1 for improved proteolytic stability against plasmin using the developed screening method described in Example 1. FGF1 was engineered using the yeast surface display platform to establish a gene-to-protein linkage. Random mutagenesis libraries for each growth factor were screened for FGFR1 binders, then mutants that remained uncleaved after incubation with protease, and finally, mutants that remained uncleaved and retained FGFR1 binding after incubation with protease. Several promising mutations were identified that appeared to increase proteolytic stability for each growth factor, and generated candidates for characterization as described in Example 3.

Results

Yeast Display of Wild Type FGF and Generation of Random Mutagenesis Library

Successful yeast display of properly folded wild-type FGF1 is described in below. Error prone PCR was used with nucleotide analogues to randomly generate mutations within wild-type FGF1. We generated a library with $3.3 \times 10^7$ mutants. By varying the concentration of nucleotide analogues, it was possible to generate an average of 3.1 mutations per mutant (2.1% mutation rate), which was hypothesized to be a diversity that is high enough to generate mutants with improved proteolytic and low enough to avoid accumulating mutations that would impair proper protein folding or binding affinity for the FGFR1 receptor.

Sort 1: Selection for Binders to FGFR1-Fc

Figure 12A:
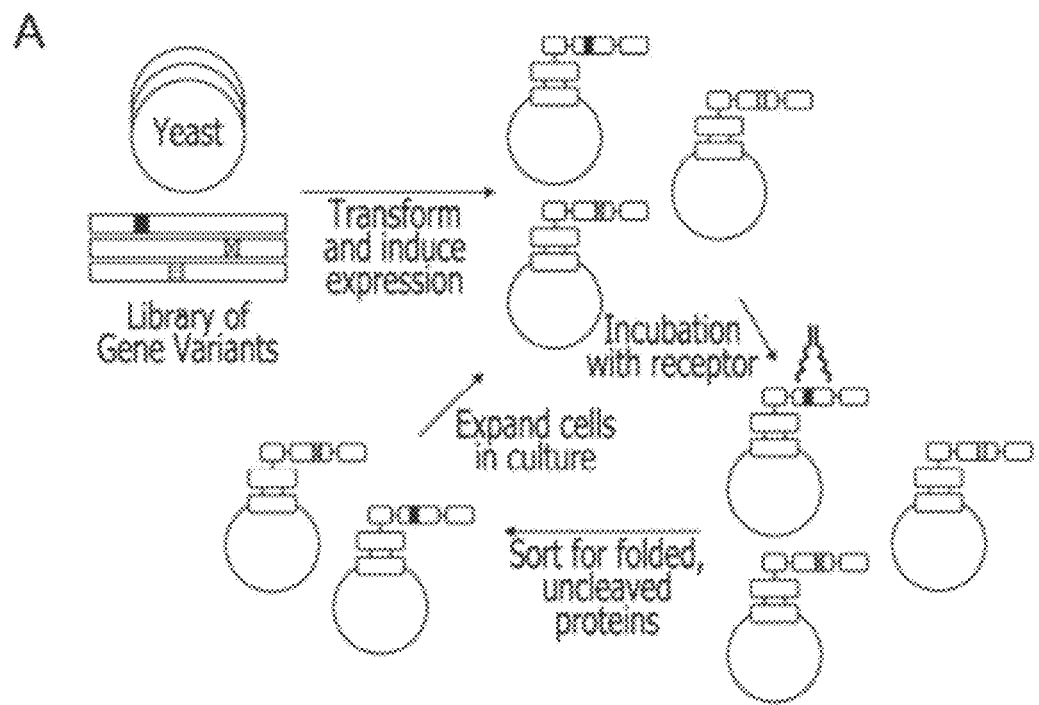
FIG. 12A-FIG. 12B Sort 1: Selection for FGFR1-Fc binders. (A) Schematic of screening method for binders to FGFR1-Fc. Random mutagenesis libraries were induced for expression of FGF mutants on the surface of yeast. Cells were incubated with 10 nM FGFR1-Fc, washed, then stained with fluorescent antibodies for expression (α-c-myc) and FGFR1 binding (α-FGFR1-Fc). Fluorescence activated cell sorting (FACS) was used to analyze and gate for cells that exhibited high c-myc signal and high FGFR1-Fc signal. (B) The FACS dot plots are shown for FGF1. The percentage of cells that were collected from the total population is shown next to the drawn gates on the dot plots.
Figure 12B:
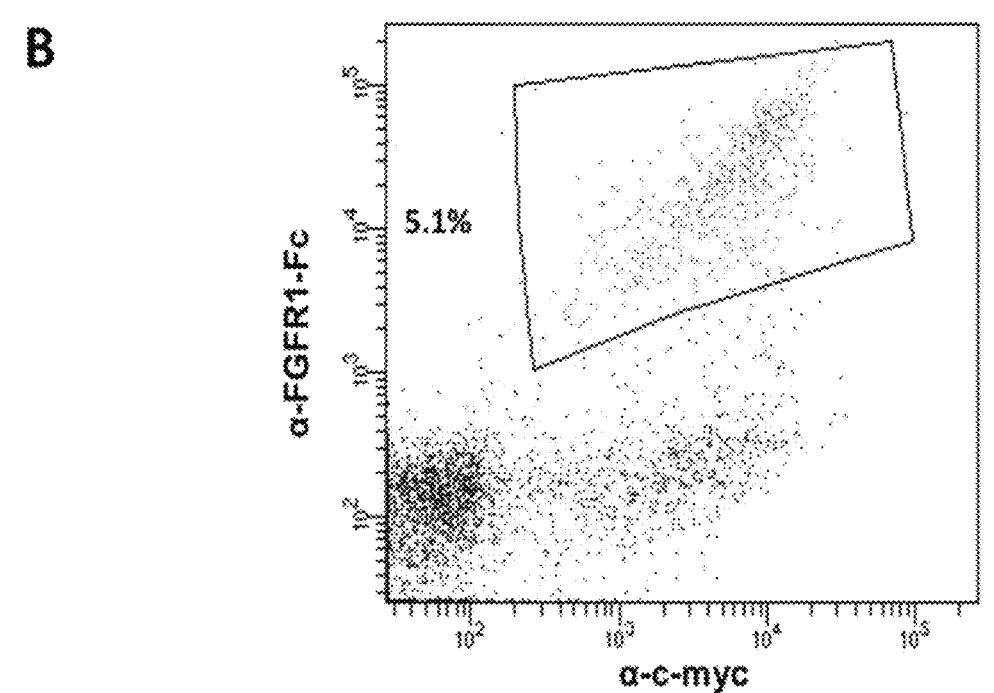

For the first sort, FGF1 mutants were sorted for that retained binding affinity for FGFR1-Fc (FIG. 12A). It was hypothesized that most random mutations would lead to a loss of binding affinity. After incubation with FGFR1-Fc, we gated for and collected cells that showed high expression (α-c-myc) and high binding signal (α-FGFR1-Fc). For the FGF1 library, a clear separation between mutants that were non-binders and those that retained FGFR binding affinity was observed (FIG. 12B).

Sort 2: Selection for Resistance to FGF1—Specific Cleavage

Figure 13A:
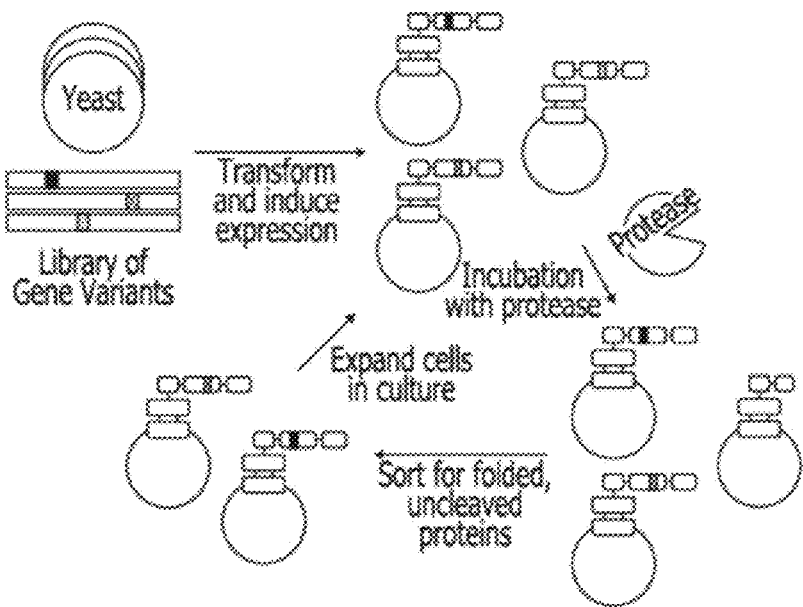
FIG. 13A-FIG. 13B Sort 2: Selection for resistance to FGF1-specific cleavage. (A) Schematic of screening method for Sort 2. Cells from Sort 1 were induced for expression and incubated with plasmin. Cells were washed, then stained with fluorescent antibodies for expression (α-HA) and resistance to FGF1-specific cleavage (α-c-myc). Fluorescence activated cell sorting (FACS) was used to analyze and gate for cells that exhibited high c-myc signal normalized by the HA expression signal. (B) The FACS dot plots is shown for FGF1. Cells from Sort 1 of each library were incubated in various concentrations of plasmin for varying incubation times as detailed. The final conditions used for gating and collection of cells for enrichment are noted. The same gate is drawn for all tested conditions.
Figure 13B:
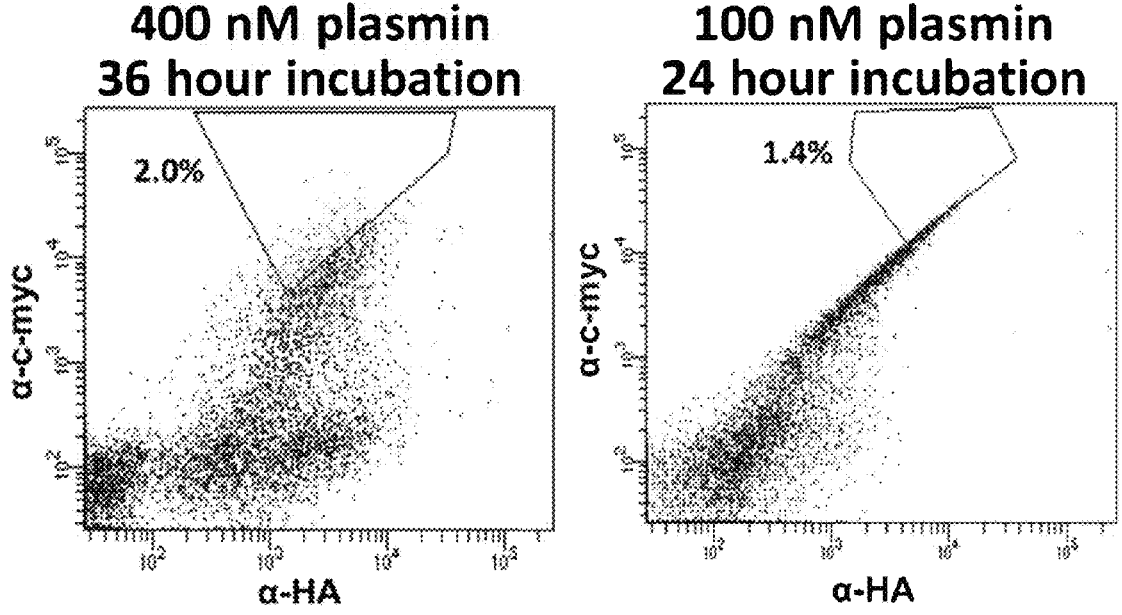

For the second sort, the cells from Sort 1 were expanded and sorted for FGF1 mutants that remained resistant to cleavage when incubated with plasmin (FIG. 13A). To obtain an effective dynamic range and differentiate between mutants with different proteolytic stabilities, the incubation of the cells was tested with varying concentrations and durations of incubation. It was found that for the FGF1 library, incubation with 400 nM plasmin for 36 hours was necessary to achieve a clear separation between the populations of cleaved and uncleaved mutants (FIG. 13B). The top 1-2% of cells exhibiting the highest level of protease resistance were collected (high α-c-myc) normalized by the expression level (α-HA).

Isolation of Peptide Artifacts During Screening.

Figures 14A, 14B:
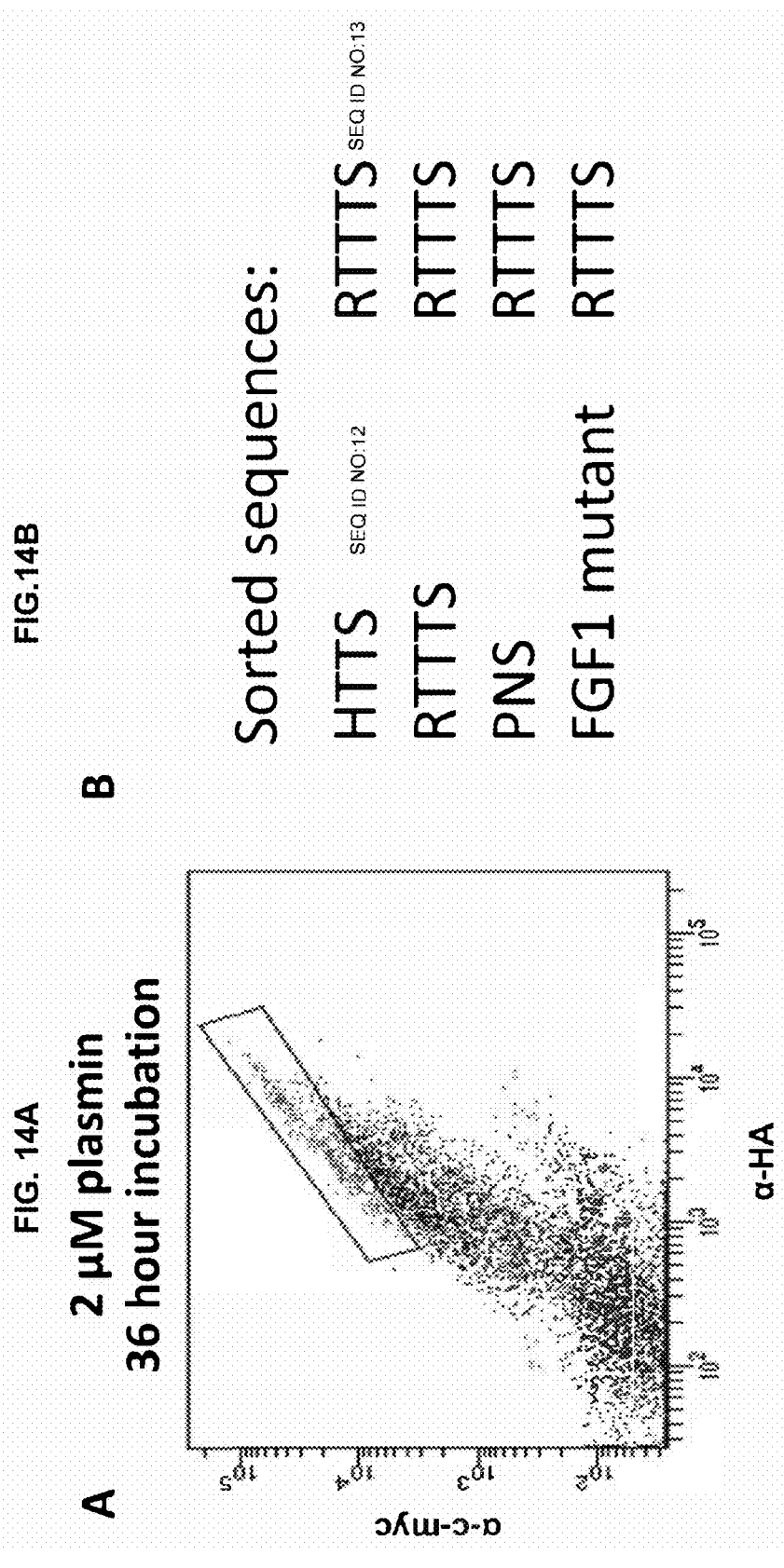
FIG. 14A-FIG. 14B Isolation of peptide artifacts. (A) The FACS dot plot is shown for the sorting of the FGF1 Sort 2 library. A selection for resistance to FGF1-specific cleavage was applied in the same manner as Sort 2. A collection gate was drawn around a subpopulation of cells that exhibited significantly higher resistance to proteolytic cleavage (c-myc). (B) The protein sequence of mutants collected from the gate are shown. Most consist of short peptides that are artifacts of random mutagenesis, including HTTS (SEQ ID NO:12), RTTTS (SEQ ID NO:13), PNS, and not derived from FGF1.

The second sort of the FGF1 library was expanded and subjected to another round of selection for resistance to FGF1-specific cleavage using HA and c-myc signals. Upon incubation with 200 nM plasmin for 36-hour incubation, it was clearly observed that a population of cells that showed much higher c-myc signal as compared to the rest of the library, indicating significantly greater resistance of yeast displayed protein to cleavage by plasmin (FIG. 14A). This population was collected and sequenced individual clones for analysis (FIG. 14B). It was found that the majority of cells did not express FGF2 mutants on their cell surface, but short peptide artifacts, including HTTS (SEQ ID NO:12), RTTTS (SEQ ID NO:13), PNS, that may have been generated during random mutagenesis instead.

Figures 15A, 15B:
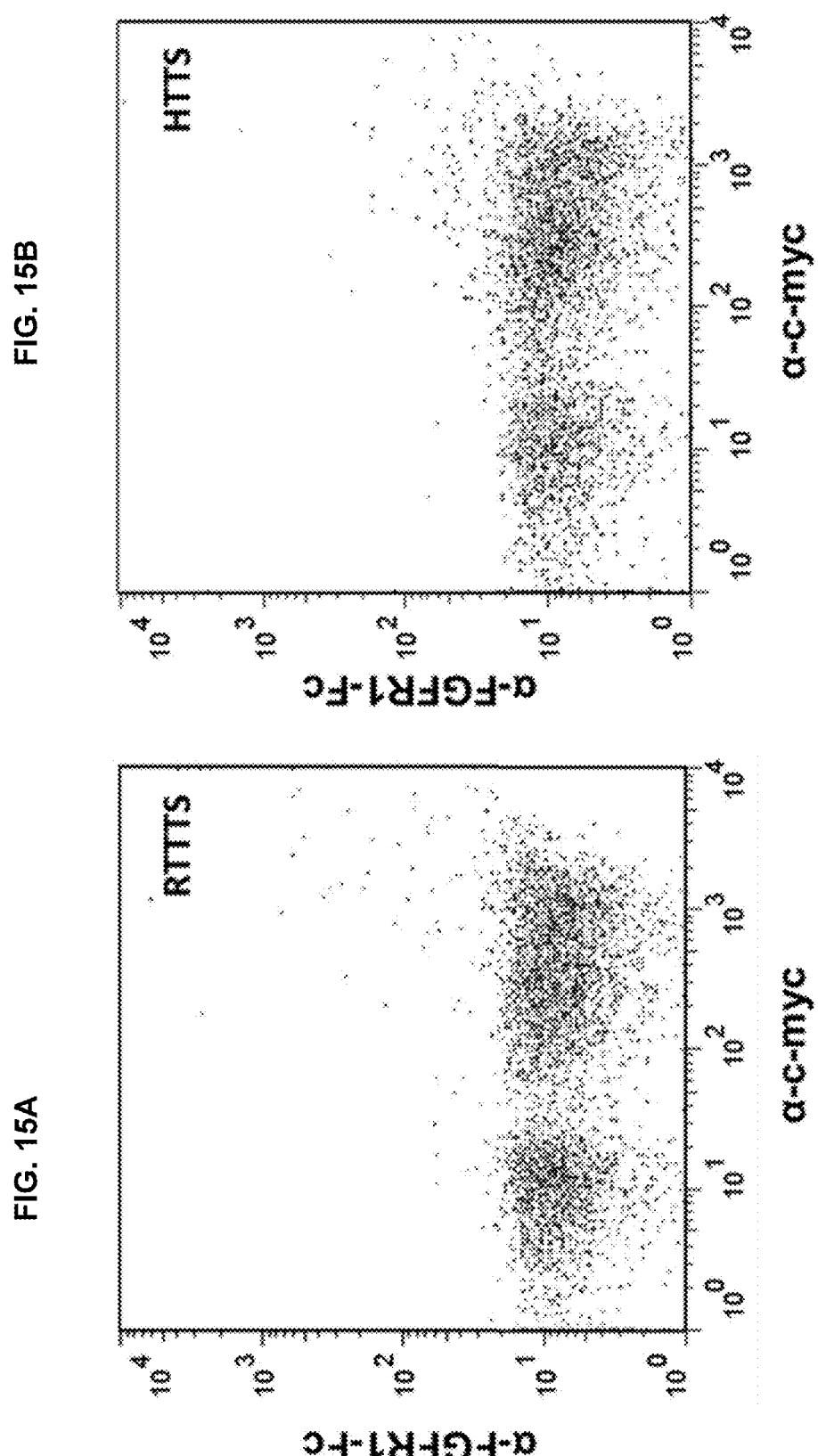
FIG. 15A-FIG. 15B Non-binding of peptide artifacts to FGFR1-Fc. Yeast cells expressing RTTTS (SEQ ID NO:13) or HTTS (SEQ ID NO:12) peptides on their cell surface were incubated with 10 nM FGFR1-Fc. Cells were stained with fluorescent antibodies for expression (α-c-myc) and binding (α-FGFR1-Fc). No significant binding signal was detected, indicating that the peptides do not bind to FGFR1-Fc.

It was confirmed that these peptides did not exhibit any specific binding to FGFR1-Fc, indicating that sorting for resistance to FGF1-specific cleavage led to a rapid enrichment of a very small population of cells expressing these peptide artifacts (FIG. 15). Thus, for all subsequent sorts, we proceeded to include a selective pressure for retaining FGFR1 binding affinity.

Sorts 3-4: Selection for protease-resistant, FGFR1-Fc binders

Figure 16:
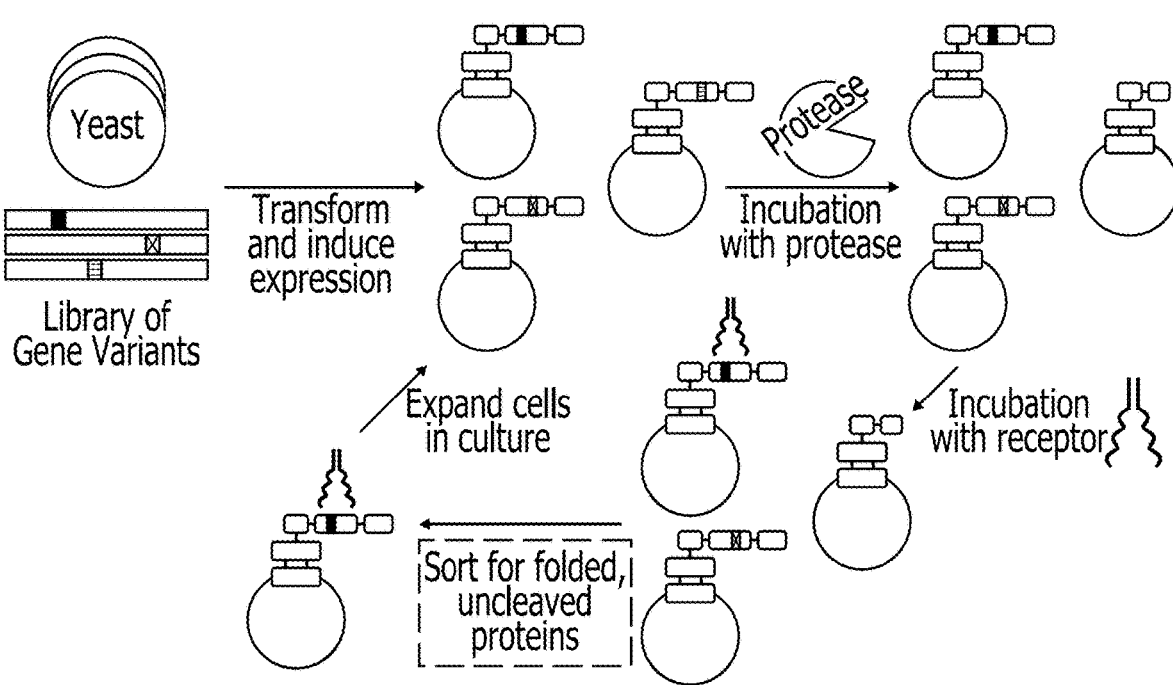
FIG. 16 Schematic for Sorts 3 and 4. Cells from the previous were induced for expression and incubated with varying concentrations of plasmin, washed, and incubated with FGFR1-Fc. After final wash, cells were then stained with fluorescent antibodies for expression (α-HA), resistance to FGF1-specific cleavage (α-c-myc), and FGFR1 binding (α-FGFR1-Fc). Fluorescence activated cell sorting (FACS) was used to analyze and gate for cells that exhibited high c-myc signal normalized by the HA expression signal and/or high FGFR1-Fc binding signal.

For the remaining sorts 3 and 4, the libraries were incubated with plasmin and, subsequently, FGFR1-Fc before selection (FIG. 16). Different combinations of α-HA, α-c-myc, and α-FGFR1-Fc were used to select for FGF1 mutants that remained uncleaved and retained binding affinity for FGFR1

Figure 17A:
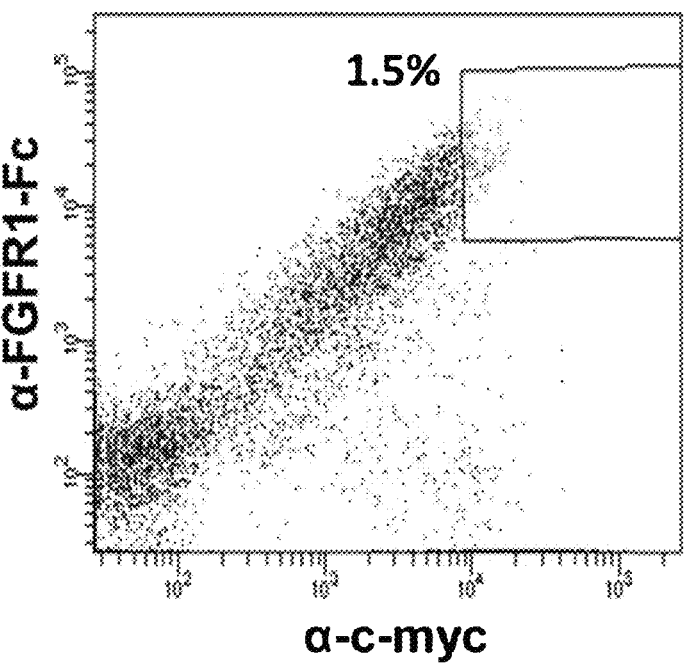
FIG. 17A-FIG. 17B Sort 3: Selection for protease-resistant, FGFR1-Fc binders. Induced cells from Sort 2 were incubated in the indicated concentrations of plasmin for 12 hours. After washing, cells were incubated with 10 nM FGFR1-Fc. After a final wash, cells were stained with fluorescent antibodies for expression (α-HA) and FGFR1 binding (α-FGFR1-Fc). Fluorescence activated cell sorting (FACS) was used to analyze and gate for cells that exhibited high HA signal and high FGFR1-Fc signal. The FACS dot plots are shown for FGF1. The percentage of cells that were collected from the total population is shown next to the drawn gates on the dot plots. Bottom panel: Retain binding to FGFR1-Fc after incubation with 1.25 μM plasmin for 24 hours.
Figure 17B:
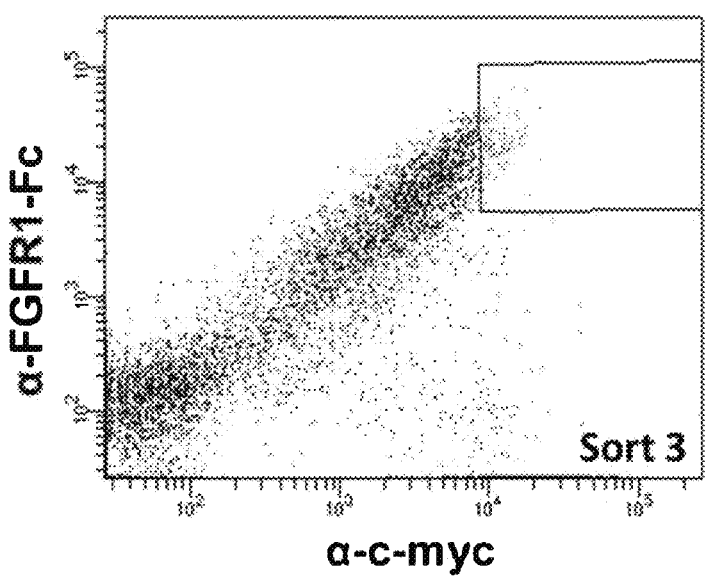

For the third sort of FGF1, we expanded the cells from Sort 2 and sorted for FGF mutants that retained FGFR1 binding after incubation with plasmin (FIG. 17). 12-hour incubations with higher concentrations of plasmin were performed. 1.5 μM plasmin was ultimately used for sorting the FGF1 library. We gated for and collected cells that showed high binding signal (α-FGFR1-Fc) and high expression (α-HA).

Figure 18A:
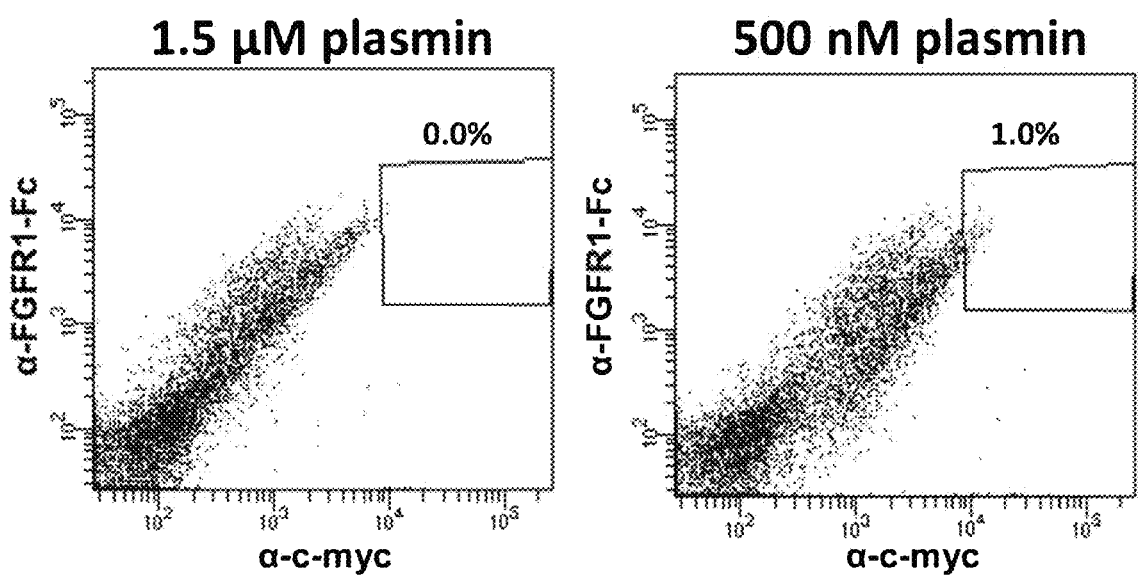
FIG. 18A-FIG. 18B Sort 4: Selection for protease-resistant, FGFR1-Fc binders. Induced cells from Sort 3 were incubated in various concentrations of plasmin for 36 hours. After washing, cells were incubated with 10 nM FGFR1-Fc.
Figure 18B:
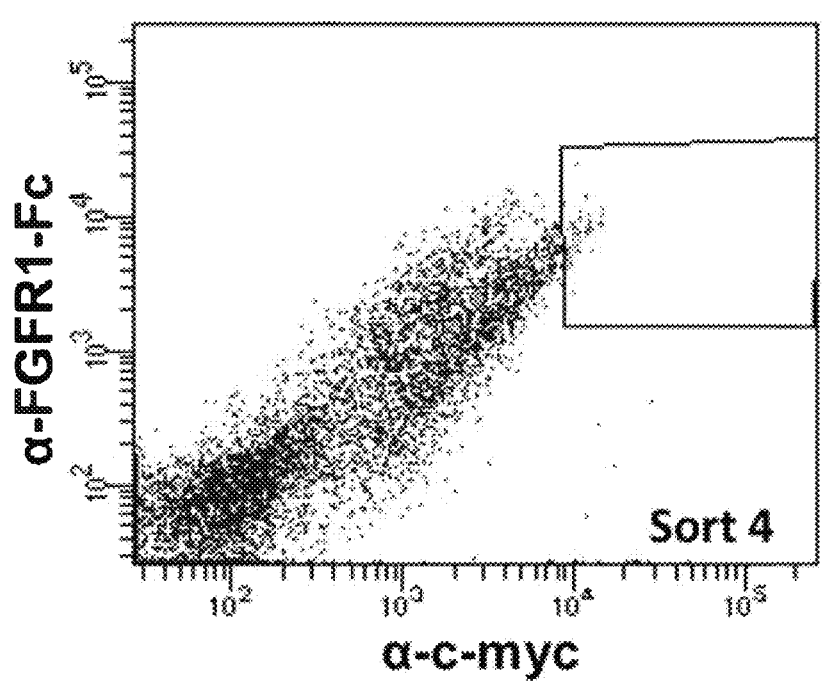

For the fourth sort of FGF1, we expanded the cells from Sort 3 and increased the time of plasmin incubation from 12 hours to 36 hours. The cells from Sort 3 were incubated in either 1.5 μM plasmin or 500 nM plasmin. We ultimately sorted for cells incubated with 500 nM plasmin (FIG. 18). We gated for and collected cells that showed high resistance to cleavage (α-c-myc) and high binding signal (α-FGFR1-Fc). By Sort 4, a completed consensus was reached for the FGF1 library and seized to perform additional rounds of sorting.

Sequence Analysis of Sorted FGF1 Mutants

For the final sort 4, individual clones were randomly selected and sequence for analysis. We were able to reach complete consensus within four rounds of sorting. The mutant (BS4M1) contains two mutations: D28N and L131R (FIG. 19). Aspartic acid 28 is part of the first (LPDG (SEQ ID NO:15)) of three key β-hairpins that close off the six-stranded β-barrel structure of FGF1. Leucine 131 is found within a β-strand pair between the N-terminus and C-terminus of FGF1.

DISCUSSION

In this example, the engineering of FGF1 for proteolytic stability against plasmin was described. As the first step, we were able to successfully express the wild-type FGF1 and wild-type FGF2. The proteins were shown to be successfully expressed and properly folded by detection of the c-myc tag testing for specific binding against FGFR1-Fc or sFGFR3-D2D3-Fc. It was observed that FGF1 exhibits a relatively high expression signal, which is interesting given that FGF1 is considered to be unstable with short half-life and a low melting temperature[21]. It is reported that yeast display expression and secretion efficiency is loosely correlated with protein stability for poorly stable proteins, but this is not always the case[48,49]. Thus, this example demonstrated that yeast display was able to accommodate the expression of unstable wild-type growth factors for engineering.

The high expression of FGF1 by yeast display led to a good dynamic range of signals during the sorting of the FGF1 random mutagenesis library and subsequent sorts. The FGF1 sorts could be subjected to high concentrations of plasmin and long incubation times for increasing stringency. This was particularly valuable in Sort 2, in which a clear separation between cleaved FGF1 mutants and non-cleaved FGF1 mutants was achieved.

Although an initial round of sorting was done to select for FGFR binders in Sort 1, we found that only using the HA and c-myc signals for measuring cleavage led to a rapid enrichment of non-FGFR-binding peptides in the sorts. In just two such sorts, a clear separation of the peptide-expressing population from the rest of the library was identified. Although the libraries were constructed by random mutagenesis with a wild type FGF as the scaffold, rare errors in the random mutagenesis process probably led to an extremely small population of cells expressing peptide artifacts. While these artifacts would be of little consequence for more traditional yeast display screens for affinity maturation, they became rapidly significant without a selective pressure for receptor binding. Thus, it was concluded that selective pressure for measuring binding affinity is essential, and that no more than one sort should be done by selecting mutants based on cleavage activity alone.

Through the screening process, we identified several enriched mutations that could be significant for improving proteolytic stability. Interestingly, the mutations are found in the β-loop region or near the C-terminus of the protein, which are implicated to be key regions for determining protein stability. For the FGF1 library, complete consensus within four rounds of sorting was reached. The FGF1 BS4M1 mutant contains two mutations: D28N and L131R. Aspartic acid 28 is part of the first (LPDG (SEQ ID NO:15)) of three key β-hairpins that close off the six-stranded β-barrel structure of FGF1. The importance of the Asx-Pro-Asx-Gly (BPBG (SEQ ID NO:16))motifs in its contribution to the stability of FGF1 has previously been studied, and substituting Asx residues with alanines has been shown to greatly de-stabilized FGF1[50]. However, it was shown that a substitution of D28N actually increases its Gibbs free energy by ~2.5 kJ/mol, suggesting that proteolytic stability may not always correlate with thermostability. Leucine 131 is found within a β-strand pair between the N-terminus and C-terminus of FGF1. Because there is no 1-hairpin to stabilize the β-barrel structure adjacent to this 1-strand pair, it has been hypothesized that the amino acids in this pair are important for stabilizing the barrel either by bonding strength between the two strands or by making it sterically favorable for the main chain to be positioned in a manner that closes the β-barrel structure. Indeed, the mutation of proline 134 to cysteine, threonine, or valine has been shown to increase stability of FGF1 by −6 to −8 kJ/mol[51].

In conclusion, it was shown that the screen for proteolytic stability was able to successfully enrich for mutations in positions that are reported to be important for FGF1 protein stability in the literature. In Example 3, we characterize the mutations identified in the final FGF1 BS4M1 mutant for their effects on the stability of solubly expressed FGF1 and the ligand's ability to modulate the FGF pathway.

Materials & Methods

Yeast Surface Display of Proteins

YPD medium consists of 20 g/L dextrose, 20 g/L peptone and 10 g/L yeast extract. Selective SD-CAA medium consists of 20 g/L dextrose, 6.7 g/L yeast nitrogenous base without amino acids (Difco), 5 g/L casamino acids (Bacto), 5.4 g/L Na$_2$HPO$_4$, and 8.56 g/L NaH$_2$PO$_4$·H$_2$O. SD-CAA plates contain the same components as the media, with the addition of 182 g/L sorbitol and 15 g/L of agar. SG-CAA induction medium is identical to SD-CAA but contains 20 g/L galactose instead of dextrose. Yeast were grown and induced at 30° C. with shaking at 235 rpm.

The pCT yeast display plasmids were transformed into *Saccharomyces cerevisiae* strain EBY100 by electroporation and recovered in YPD at 30° C. for 1 hr before plating on SD-CAA plates. After 3 days, yeast colonies were inoculated overnight in SD-CAA. Expression and yeast display of proteins were induced in SG-CAA at 30° C. for 24 hours according to established protocols[52].

Library Creation

FGF1 was cloned from human FGF1 cDNA (MGC Clone: 9218, IMAGE: 3896359, Residues: Phe16 to Asp155) into pCT vector (restriction sites: NheI, BamHI) for yeast display. The FGF1 random mutagenesis library was generated using error-prone PCR as described previously[52,53]. FGF1 was used as the template, and mutations were introduced using Taq polymerase (New England Biolabs) and nucleotide analogs 8-oxo-dGTP and dPTP (TriLink Biotech). Primers that contained 50 bp overlaps with the pCT plasmid in the forward and reverse direction were used to enable the insertion of the mutant genes into the pCT vector through yeast homologous recombination. To obtain clones with a range of mutation frequencies, six PCRs were performed with varying concentrations of nucleotide analogs (40 μM, 20 μM, 10 μM, 5 μM, 2.5 μM, 1.25 μM) over 20 PCR cycles. PCR products were amplified in the absence of nucleotide analogs and purified using gel electrophoresis. The pCT plasmid was digested as the vector with NheI and BamHI. Eight transformations of 5 μg purified DNA insert and 1 μg restriction enzyme digested pCT were electroporated into electrocompetent EBY100 yeast cells. The transformed yeast cells were recovered in YPD at 30° C. for 1 hr, then grown in selective SD-CAA medium. Clones from each PCR were sampled to determine the mutagenic frequency. Clones from the 5 μM and 2.5 μM PCRs were combined to create the final library with an average of 3 mutations per clone. After two passages, the cells were transferred to SG-CAA to induce protein expression. A library size of $2 \times 10^7$ transformants was obtained as estimated by dilution plating.

Library Screening

Induced EBY100 yeast cells displaying FGF1 mutants were incubated with plasmin in plasmin digest buffer (100 mM Tris-HCl, 0.01% BSA, pH 8.5) at 37° C. and/or FGFR1-Fc in PBS+0.1% BSA (PBSA) at room temperature as described for each sort. After protease digestion steps, cells were washed with PBSA, incubated with 1:100 dilution of protease inhibitor cocktail (Sigma) in PBSA for 5 minutes, then washed again with PBSA. After FGFR incubation steps, cells were washed with PBSA. The number of yeast cells incubated for each sort was ~10× the number of cells collected in the previous sort. Cells were incubated in volumes at a density of 2 million cells per mL. After all incubation steps, cells were stained with primary and secondary antibodies. For primary staining, cells were appropriately incubated with 1:1000 dilution of anti-HA-Tag (6E2) Mouse mAb (Cell Signaling) and/or 1:2000 dilution of chicken anti-c-Myc (Invitrogen) for 30 minutes. Cells were washed with PBSA after primary staining. Secondary staining was done on ice for 10 minutes. For secondary staining, the following antibodies were used for each sort: Sort 1, 3, 4-anti-chicken-IgY-PE (Santa Cruz Biotechnology) against anti-c-myc and anti-Human IgG-FITC (Sigma Aldrich) against FGFR1-Fc; Sort 2-goat anti-mouse-PE (Invitrogen) and goat anti-chicken-IgY-AlexaFluor488 (Santa Cruz Biotechnology).

Labeled yeast cells were sorted by fluorescence activated cell sorting (FACS) using the BD FACS Aria II (Stanford Shared FACS Facility). In each sort, 0.5 to 10% of yeast cells were collected based on the criteria set for each sort. The cells collected in each sort were grown in SD-CAA (pH 5 to limit bacterial contamination) for several days until an OD of 5 to 8 was reach. Clones were induced for yeast display expression in SG-CAA for 24 hours at 30° C. prior to the next round of sorting.

For sequencing and cloning, plasmid DNA was extracted from yeast cells using a Zymoprep Yeast Plasmid Miniprep I Kit (Zymo Research). The extracted DNA was transformed into DH10B electrocompetent cells and plated. Single colonies were selected and grown in LB media (Fisher Scientific). Plasmid DNA was isolated from the single colony cultures using a plasmid miniprep kit (GeneJet). DNA sequencing was performed by MCLAB.

Binding affinity assays for yeast-displayed peptides RTTTS (SEQ ID NO:13) or HTTS (SEQ ID NO: 12)

50,000 induced yeast cells were incubated with various concentrations of FGFR1-Fc in phosphate-buffered saline with 1 g/L BSA (PBSA) at room temperature. Cells were incubated in sufficiently large volumes to avoid ligand depletion and long enough times (typically 3 to 24 hours) to reach equilibrium. During the last 30 minutes of incubation, yeast cells were incubated with 1:2500 dilution of chicken anti-c-Myc (Invitrogen) in PBSA. Yeast were pelleted, washed, then incubated with 1:200 dilution of secondary antibodies on ice for 10 min: anti-Human IgG-FITC (Sigma Aldrich) against FGFRT-Fc and anti-chicken-IgY-PE (Santa Cruz Biotechnology) against anti-c-myc. Yeast were washed, pelleted, and resuspended in PBSA immediately before analysis by flow cytometry using EMD Millipore Guava EasyCyte. Flow cytometry data were analyzed using FlowJo (v7.6.1). Binding curves were plotted and $K_d$ values were obtained using GraphPad Prism 6.

Example 3: Characterization of Proteolytically Stabilized Fibroblast Growth Factors Abstract Proteolytic stability can play an important role in improving the efficacy of unstable growth factors, such as FGF1. Studies have shown that FGF1 is rapidly degraded in culture, partially due to proteases that are found in serum or that are expressed by cells. In Example 2, the engineering of FGF1 for increased proteolytic stability is described. We screened FGF1 random mutagenesis libraries for FGF1 mutants that exhibited enhanced proteolytic stability on the surface yeast. In this example, the recombinant expression of soluble FGF1 and the characterization of the mutations identified by the high-throughput screen to improve proteolytic stability in FGF1 are described. FGF1 and FGF2 were recombinantly express and purified in *E. coli* expression systems. It was confirmed that the FGF1 BS4M1 (D28N, L131R) and L131R mutants are more proteolytically stable as compared to wild-type FGF1, and that the FGF1 L131R mutant acts as a potent FGF pathway antagonist.

Introduction

FGF1 is a potent regulatory molecule for the induction of angiogenesis, but its poor stability limits its ability to sustain protein activity and achieve prolonged efficacy. In Example 2, the use of a high-throughput screen to select for FGF1 mutants that demonstrate increased proteolytic stability upon incubation with plasmin, an important protease found in areas of disease for ECM degradation is described. Complete consensus was achieved after four sorts of the FGF1 library and identified the FGF1 BS4M1 (D28N, L131R) mutant. The mutations were found in areas of the protein that have been reported to be important for the stability of FGFs.

In this example, it is described that the soluble expression and characterization of the mutant FGFs derived from the FGF1 BS4M1 mutant identified in the screen. The wild type and FGF1 BS4M1 mutant were cloned from the yeast display vector and inserted into *E. coli* expression vectors. After purification, the proper folding of recombinant FGF1 was tested for by detection of specific binding to a yeast-displayed FGFR3 construct.

For the FGF1 BS4M1 mutant and the wild type FGF1, their soluble stability and their ability to modulate the FGF pathway were characterized further. The proteolytic stability of the proteins in plasmin or trypsin was tested, and their extent of degradation at different time points was measured using Western blot and band intensity quantification. We probed into the significance of the mutations D28N and L131R and their contributions to protein stability. The thermal stability of FGF1's were measured to analyze their relationship to proteolytic stability. To test the stability of FGF1's in more biologically relevant conditions, their extent of degradation in MDA-MB-231 breast cancer cell culture was characterized. In addition, ERK phosphorylation assays in NIH3T3 cells to characterize the ability to modulate the activation of signaling molecules that are downstream of FGFR activation such as ERK were performed. The results from these characterization studies demonstrated the improved proteolytic stability and antagonistic activity of engineered FGF1 mutants, and their potential to be used for anti-angiogenesis therapy.

Results

Recombinant Expression of FGFs

In order to express the engineered FGF1 mutants in their soluble and compare them to the wild type protein, the proteins were recombinantly expressed in *E. coli* expression systems. FGF1 and FGF1 mutants were cloned into the pBAD vector for intracellular expression of recombinant proteins. The pBAD FGF1 expression vectors were transformed into the *E. coli* strain Rosetta that enhances the expression of eukaryotic proteins with codons rarely used in *E. coli*. Cells were lysed using a detergent-based solution. Proteins were then purified using Ni-NTA column chromatography and size exclusion chromatography. The identity and purity of wild-type FGF1 was confirmed by Coomassie-stained protein gel and Western blot (FIG. 20A). Proper folding of FGF1 was confirmed by observation of specific binding to a yeast-displayed FGFR3 construct (FIG. 20B).

Proteolytic Stability of FGF1 Mutant BS4M1 in Plasmin

To measure the proteolytic stability of wild type FGF1 and the FGF1 mutant BS4M1 (D28N/L131R), 100 ng of soluble FGFs was incubated in plasmin for various incubation times. Then, their degradation rate was evaluated by running the samples on a Western blot and staining for anti-FGF. The amount of remaining FGF was calculated by measuring the band intensity for each condition and normalizing by the band intensity of protein without plasmin incubation. It was found that the BS4M1 (D28N, L131R) mutant exhibited lower levels of degradation at all incubation time points in plasmin, as compared to wild type FGF1 (FIG. 24). Thus, it was confirmed that the screen for increasing the proteolytic stability of FGF1 against plasmin was successful.

The mutations from BS4M1 (D28N and L131R) were incorporated into the stabilized PM2 (Q40P, S47I, H93G) mutant to create PM3 (D28N, Q40P, S47I, H93G, L131R). We measured the degradation of each construct at different plasmin concentrations after a 48-hour incubation. It was found that introducing the mutations from BS4M1 to the mutations from PM2 led to a marked increase in the resistance to proteolytic degradation at all tested concentrations (FIG. 25). Thus, it was concluded that the newly identified mutations in BS4M1 had an additive effect on proteolytic stability when combined with the mutations from PM2.

Proteolytic Stability of Engineered FGF Mutants in Trypsin

The proteolytic stability of wild type FGF1 and FGF1 mutant BS4M1 were measured in trypsin in a similar manner. It was hypothesized that engineering for proteolytic stability against plasmin could increase proteolytic stability in trypsin because plasmin and trypsin share the same primary specificity of lysine and arginine. In addition, it was confirmed in that the FGF1 mutant PM2 (Q40P, S47I, H93G), which is more resistant to degradation by trypsin, is also more resistant to cleavage by plasmin. it found that the BS4M1 (D28N, L131R) mutant exhibited lower levels of degradation at all incubation time points in trypsin, as compared to wild type FGF1 (FIG. 26). Thus, it was concluded that engineering for proteolytic stability of FGF1 in plasmin was successful in increasing proteolytic stability in trypsin as well.

Significance of Mutations in FGF1 Mutant BS4M1

In order to determine whether both the D28N and L131R mutations were important for conferring proteolytic stability to the BS4M1 mutant, versions of FGF1 with only the D28N or L131R mutation were created. The proteolytic stability of these mutants by evaluating their degradation rate in plasmin over time was measured. It was found that the L131R mutant exhibited comparable proteolytic stability as compared to the BS4M1 (D28N/L131R) mutant, but that the D28N mutant exhibited much lower proteolytic stability even as compared to the wild type FGF1 (FIG. 27). It was concluded that the D28N mutation did not translate to significantly increasing the proteolytic stability of FGF1 when incorporated into the solubly expressed protein. Thus, further characterizations with the L131R mutant were continued.

We also wanted to determine whether the mutation at position 131 to arginine was unique for conferring proteolytic stability, or if the mutation away from leucine was significant. Thus, position 131 was alternatively mutated to either alanine (L131A) or lysine (L13T1K) to see if these single mutants maintained or lost their enhancement in proteolytic stability. Their degradation rates were evaluated in plasmin; it was found that the L13T1K maintained similar levels of degradation as compared to L131R, while L131A exhibited higher levels of degradation even as compared to the wild type FGF1 (FIG. 28).

Thermal Stability of Wild Type FGF1 and FGF1 L131R Mutant

In order to determine whether the improvement in proteolytic stability of the FGF1 L131R mutant is attributable to an improvement in thermal stability, we measured the melting temperature of the wild type FGF1 and the FGF L131R mutant. We used the ThermoFluor assay with a hydrophobic dye to measure the unfolding of each protein as the temperature is gradually increased[54,55]. It was found that while the L131R mutation leads to a slight increase in the melting temperature as compared to the wild type FGF1, the difference is not statistically significant (FIG. 29). Thus, it was concluded that the thermal stability does not contribute significantly to the increase in proteolytic stability for the FGF1 L131R mutant.

Stability of FGF1 L131R Mutant in Cell Culture

The stability of the FGF1 L131R mutant was tested in culture with MDA-MB-231, a breast cancer cell line that expresses urokinase plasminogen activator (uPA) to activate plasminogen and convert it into plasmin. 500 ng of protein was incubated for various incubation times with MDA-MB-231 in culture. All of the protein for each condition was concentrated and loaded each condition into a separate well for analysis by Western blot. The amount of protein left was quantified by measuring the band intensity and normalizing by 500 ng of protein that was not incubated in culture. It was found that the FGF1 L131R mutant exhibited increased stability in culture as compared to the wild type protein (FIG. 30).

FGF1 L131R Mutant is an FGFR Antagonist

To characterize the ability of FGF1 L131R to modulate the FGF pathway, we evaluated its ability to modulate phosphorylation of ERK (MAPK), a key signaling molecule that is downstream of FGFR activation and is important for induction of cell proliferation[56,57]. NIH3T3 cells, which express FGFRs, were incubated with wild type FGF1 alone, the FGF1 L131R mutant alone, or wild type FGF1 with various concentrations of the FGF1 L131R mutant. It was found that while the FGF1 L131R mutant is unable to induce ERK phosphorylation, the mutant can effectively inhibit ERK phosphorylation by wild-type FGF1 (FIG. 31). For 1 nM wild type FGF1, we generated a dose-response curve for the inhibition of ERK phosphorylation by the FGF1 L131R mutant and found that its IC50 (1 nM) is equimolar to the concentration of wild type FGF1 (FIG. 32).

Binding of FGF1 L131R Mutant to NIH3T3 Cells

The binding affinity of the FGF1 L131R mutant was characterized and compared to that of wild-type FGF1. NIH3T3 cells which express FGFRs were incubated with varying concentrations of FGF1 at 4° C. to prevent incubation. The cells were labeled with a fluorescently tagged anti-His antibody to detect bound His-tagged FGF1. It was found that both FGF1 WT and the FGF1 L131R mutant exhibit a binding affinity of 10 nM for NIH3T3 cells (FIG. 33).

Discussion

In this example, we solubly expressed and characterized the FGF mutants that were identified in the screen for proteolytic stability in plasmin from Example 2. Upon recombinant expression, it was found that FGF1 was expressed and purified easily. However, it was found that the yield of the expressions was fairly low at 1-3 mg/L of expression. This low protein yield may be due to the poor stability of FGF1.

The soluble FGF1 BS4M1 (D28N, L131R) mutant was successfully confirmed to exhibit increased proteolytic stability in plasmin as compared to wild-type FGF1. When the mutations D28N and L131R were combined with the mutations from the stabilized FGF1 PM2 mutant (Q40P, S47I, H93G) from Zakrzewska et al.[14], it was found that new mutations further enhanced the proteolytic stability of FGF1 in plasmin. In addition, the BS4M1 mutant was found to be more stable in trypsin, a protease that cleaves after lysine and arginine in a manner similar to plasmin[58]. This demonstrates the ability of the screen to increase the protein's proteolytic stability in the presence of other proteases that share primary specificity with the protease used for selection. For example, the BS4M1 mutant may also be more proteolytically stable in the presence of cathepsins, which are responsible for lysosomal degradation and share primary specificity with plasmin.

Through characterization of the FGF1 D28N and L131R single mutants, it was found that most of the increased proteolytic stability was attributable to L131R, while the D28N single mutant was even less proteolytically stable than the wild-type. The difference in the significance of the D28N mutation between the yeast-displayed FGF1 and the soluble *E. coli*-derived FGF1 may be attributable to glycosylation which only occurs in the yeast displayed protein. Mutation of the aspartic acid to asparagine leads to the introduction of an NGx glycosylation site for eukaryotes[59]. Thus, FGF1 BS4M1 mutant that is expressed in yeast or mammalian cells may have additional proteolytic stability.

The L131R mutation is a counter-intuitive one, as plasmin has primary specificity for arginine. Indeed, no rational design strategy would involve introducing new potential cleavage sites to the protein. However, as discussed in Example 1, primary specificity is not the only determinant of whether protein cleavage occurs at a potential cleavage site; multiple amino acids around the site and the steric accessibility of the site to the protease also contribute greatly. To probe further into whether the mutation away from leucine or the mutation to arginine at position 131 is important for increasing proteolytic stability, FGF1 L131A and L131K single mutants were characterized. It was found that changing leucine 131 to an alanine, an amino acid commonly used for substitution of a protease cleavage site by rational design, led to a decrease in proteolytic stability even as compared to the wild-type FGF1. However, mutation of leucine 131 to a lysine, the other amino acid that plasmin has primary specificity for, led to a retention in the increased proteolytic stability in plasmin. While it was considered whether cleavage of the FGF1 protein at position 131 by plasmin leads to an increased proteolytic stability of the resulting protein fragment, it was concluded that the screen could not have selected for such a mutation. Any cleavage within the yeast displayed FGF1 would have led to a loss of c-myc signal and selection away from this mutant. Because lysine and arginine are both positively charged amino acids, it may instead be possible that the addition of a positive charge to this position is important for increasing the proteolytic stability of FGF1. We found that there was no statistically significant difference in melting temperature between wild-type FGF1 and the FGF1 L131R mutant, suggesting that an increase in thermal stability does not explain the increase in proteolytic stability. Thus, further studies would be required to definitively find the mechanism of L131R for increasing proteolytic stability.

It was also found that the FGF1 L131R mutant appears to be more stable than wild-type FGF1 in cell culture with MDA-MB-231 breast cancer cells. These cells express urokinase plasminogen activator (uPA), which cleaves and activates plasminogen into plasmin. That result was significant for demonstrating that the FGF1 L131R mutant exhibits increased stability in a more biologically relevant context.

Finally, using the ERK phosphorylation assay in NIH3T3 cells, it was found that the L131R mutation turns FGF1 into an FGF pathway antagonist. This result is interesting while reasonable, given that the screen for increasing proteolytic stability only selects for mutants that bind to FGFR but does not select for whether the protein acts as an agonist or an antagonist. The binding affinity of the FGF1 L131R mutant to NIH3T3 cells is roughly equivalent to that of wild-type FGF1, which explains why the IC50 of the FGF1 L131R mutant is roughly equimolar to the concentration of wild-type FGF1 used in the inhibition assay. The inhibition of ERK phosphorylation by the FGF1 L131R mutant is not complete, as the samples treated with the highest concentrations of the FGF L13R mutant in the presence of wild-type FGF1 show a low level of ERK phosphorylation that is above that of untreated cells. However, this phenomenon is also observed in the FGF1 R50E mutant, which is the only other FGF1 mutant that is reported to act an antagonist in the literature[60]. It is reported that sustained, high levels of ERK phosphorylation for the induction of FGF pathway-associated cell proliferation and the activation of downstream effector proteins such as cyclin D1[57,61]. The FGF1 R50E mutant is defective in its binding to integrin $\alpha v \beta$, and it also shows incomplete inhibition of ERK phosphorylation. However, in a follow-up study by Mori et al., they successfully show that their FGF1 R50E antagonist is able to inhibit FGF1-induced cell migration, HUVEC tube formation, angiogenesis in Matrigel plug assays, and the outgrowth of cells in aorta ring assays[41]. Thus, this example provides good evidence that the FGF1 L131R can similarly act as an FGF pathway antagonist in functional biological assays.

In conclusion, the results described in this Examples 2 and 3 show that we were able to successfully utilize our high-throughput screen for increasing the proteolytic stability of FGF1 in plasmin and identify key proteolytically stabilized candidates for FGF2. It was shown that the FGF1 mutants exhibit increased proteolytic stability in plasmin and trypsin, and increased stability in culture. It was demonstrated that the FGF1 L131R mutant acts as a potent FGF pathway antagonist that can be used to inhibit FGF1-induced ERK phosphorylation in NIH3T3 cells. The FGF1 mutants demonstrate their promise for development of a proteolytically stabilized therapeutic molecule for anti-angiogenesis therapy in the treatment of diseases such as cancer and unwanted neovascularization in the eye.

Materials & Methods

Recombinant FGF1 Expression and Purification

FGF1 was expressed using Rosetta (DE3) competent cells (Novagen). The gene was cloned from human FGF1 cDNA (Dharmacon) into the pBAD/His B vector (Invitrogen) with an N-terminal 6× His tag and an arabinose-inducible promoter. The restriction sites XhoI and HindIII were used for cloning. The pBAD FGF1-His plasmid was transformed into chemically competent Rosetta (DE3) cells, recovered in 1 mL LB at 37° C. with shaking at 235 rpm, and plated on LB plates with ampicillin (Amp) selection. Colonies were inoculated into 5 mL LB Amp and grown at 37° C. overnight. 1 mL of the overnight culture was used to inoculate a 100 mL LB Amp expression culture. Cells were grown at 37° C. with shaking at 235 rpm for 2 to 2.5 hours. At an OD600 of ~0.5, the cells were induced with 0.2% L-arabinose (Sigma Aldrich). The proteins were expressed and maintained in the cell cytoplasm. The expression culture was grown for 6 hours at 37° C. before the cells were spun down and collected.

The cells were lysed in B-PER Bacterial Protein Extraction Reagent (Thermo Scientific) with lysozyme, DNase I, and heparin sulfate for 30 minutes. The extraction mixture was spun down at 15,000 g for 10 minutes, and the supernatant was collected and filtered through a 0.22 μm filter. The supernatant containing the FGF1 was diluted in a 1:10 dilution with binding buffer for Ni-NTA affinity purification, as detailed in Section 2.5.6.1. The supernatant and binding buffer mixture was loaded onto the Ni-NTA column. The elution from Ni-NTA affinity purification was concentrated and buffer exchanged into PBS using the Amicon Ultra-4 Centrifugal Filter Unit with 10 kDa cutoff. Size exclusion chromatography with the Superdex 75 column was used to purify the final FGF1-His protein, as described in Section 2.5.6.1.

Cloning of FGF1 Single Mutants

Overlap extension PCR was used to mutate wild-type FGF1 into single amino acid mutants[62]. The codon mutations are as follows: D28N-GAT to AAT; L131R-CTA to CGA; L131A-CTA to GCA; L131K-CTA to AAA. The site-specific mutagenesis primers incorporated the codon mutations as well as 20 bp overhangs on each side that overlap with the wild-type FGF1 sequence.

Proteolytic Stability Assay

For each condition, 125 ng of protein was incubated in 20 μL of plasmin digest buffer (100 mM Tris-HCl, 0.01% BSA, pH 8.5) with varying concentrations of plasmin or for varying incubation times at 37° C. At the end of the appropriate incubation time for each sample, the protease digestion was stopped by storage of the sample at −20° C. After the completion of all incubations, samples were thawed on ice for analysis. Each 20 μL sample was mixed with 5 μL of NuPAGE LDS Sample Buffer and 2 μL of NuPAGE Sample Reducing Agent. The samples were heated to 95° C. for 10 minutes prior to running SDS-PAGE gels. Gels were incubated with 20% ethanol for 10 minutes prior to blotting onto a nitrocellulose membrane using the Invitrogen iBlot Gel Transfer Device (Program 0, 7 minutes).

The Western blots were blocked with 5% nonfat dry milk (Bio-Rad) in TBST (137 mM NaCl, 2.7 mM KCl, 25 mM Tris, 0.1% Tween 20) for one hour. Primary staining was done with 1:1000 dilution of mouse anti-FGF1 (Sigma Aldrich, clone 2E12) in 5% milk in TBST for one hour. After washing three times in TBST for 15 minutes, secondary staining was done with 1:2500 dilution of goat anti-mouse HRP (ThermoFisher Scientific) for 2 hours. After washing three more times in TBST for 15 minutes, the blots were imaged by BioRad ChemiDoc XRS System in Chemi Hi Sensitivity mode. Band intensities were quantified using ImageJ and normalized band intensities were plotted using GraphPad Prism 6.

ThermoFluor Assay for Measuring Melting Temperature

50 μL of 1.2 mg/mL protein was loaded into a 96-well, thin-wall PCR plate (Bio-Rad). 0.5 μL of SYPRO Orange (Molecular Probes) was added to the sample and mixed thoroughly. The plate was sealed with a plastic cover prior to plate analysis with BioRad CFX96 RT System C1000 Touch. The plate was cooled to 4° C. for 5 minutes and then the plate was heated slowly up to 100° C. at a rate of 1° C. per minute. Fluorescence changes were monitored and measured at each ° C. The fluorescence over temperature was plotted on Microsoft Excel and the melting temperature was calculated by finding the temperature at which the fluorescence equals the average of the maximum and minimum fluorescence signals.

Cell Culture Stability Assay

MDA-MB-231 cells were seeded on 6-well plates (Sigma Aldrich) at a density of 100,000 cells/well in Dulbecco's Modified Eagle Medium (DMEM) (Gibco) with 10% fetal bovine serum (FBS) (Gibco) and grown at 37° C. in 5% $CO_2$. After 24 hours, the media was aspirated and replaced with DMEM for serum starvation. After 24 hours, the DMEM was aspirated. For each sample, 500 ng of protein in 1 mL of DMEM was added to each well and incubated at 37° C. in 5% $CO_2$ for varying incubation times. At the end of each incubation, the supernatant was collected, filtered with 0.22 μm filter, and frozen down at −20° C. prior to analysis.

After all incubations were complete, supernatants were thawed on ice. Each supernatant sample was concentrated down to 50 μL volume using Amicon 3K MWCO Ultra-0.5 mL Centrifugal Filters. 15 μL of the concentrated sample was mixed with 5 μL of NuPAGE LDS Sample Buffer and 2 μL of NuPAGE Sample Reducing Agent. The samples were heated to 95° C. for 10 minutes prior to running SDS-PAGE gels. Gels were incubated with 20% ethanol for 10 minutes prior to blotting onto a nitrocellulose membrane using the Invitrogen iBlot Gel Transfer Device (Program 0, 7 minutes).

The Western blots were blocked with 5% nonfat dry milk (Bio-Rad) in TBST (137 mM NaCl, 2.7 mM KCl, 25 mM Tris, 0.1% Tween 20) for one hour. Primary staining was done with 1:1000 dilution of mouse anti-FGF1 (Sigma Aldrich, clone 2E12) in 5% milk in TBST for one hour. After washing three times in TBST for 15 minutes, secondary staining was done with 1:2500 dilution of goat anti-mouse HRP (ThermoFisher Scientific) for 2 hours. After washing three more times in TBST for 15 minutes, the blots were imaged by BioRad ChemiDoc XRS System in Chemi Hi Sensitivity mode. Band intensities were quantified using ImageJ and normalized band intensities were plotted using GraphPad Prism 6.

NIH3T3 ERK Phosphorylation Assay

MDA-MB-231 cells were seeded on 6-well plates (Sigma Aldrich) at a density of 100,000 cells/well in Dulbecco's Modified Eagle Medium (DMEM) (Gibco) with 10% new-born calf serum (NBCS) (Gibco) and grown at 37° C. in 5% $CO_2$. After 24 hours, the media was aspirated and replaced with DMEM for serum starvation. After 24 hours, the DMEM was aspirated. Cells were stimulated with wild-type FGF1 and/or varying concentrations of FGF1 L131R mutant for 15 to 18 hours at 37° C. without any phosphatase inhibitors. After stimulation, cells were washed with ice-cold PBS and treated with 100 μl of lysis buffer (20 mM Tris-HCl, pH 8.0, 137 mM NaCl, 10% Glycerol, 1% Noni-det P-40) with 1X phosphatase inhibitor cocktail 2 and 1X protease inhibitor cocktail 2 (Sigma) for 1 hour at 4° C. Lysates were frozen down at −80° C. prior to analysis. Lysates were thawed on ice and clarified by centrifugation. Protein concentrations were quantified with Pierce BCA Protein Assay. 2 μg of protein lysate for each sample was diluted to 14.6 μL with MilliQ $H_2O$. Each diluted sample was mixed with 5.6 μL of NuPAGE LDS Sample Buffer and 2.25 μL of NUPAGE Sample Reducing Agent. The samples were heated to 95° C. for 10 minutes prior to running SDS-PAGE gels. Gels were incubated with 20% ethanol for 10 minutes prior to blotting onto a nitrocellulose membrane using the Invitrogen iBlot Gel Transfer Device (Program 0, 7 minutes).

The Western blots were blocked with 5% nonfat dry milk (Bio-Rad) in TBST (137 mM NaCl, 2.7 mM KCl, 25 mM Tris, 0.1% Tween 20) for one hour. Primary staining was done with 1:1000 dilution of rabbit anti-phospho-ERK1/2 (Y202/Y204) antibody (Cell Signaling) or rabbit anti-ERK1/2 (Cell Signaling) in 5% milk in TBST for one hour. After washing three times in TBST for 15 minutes, second-ary staining was done with 1:2500 dilution of goat anti-rabbit HRP (Santa Cruz Biotechnology) for 2 hours. After washing three more times in TBST for 15 minutes, the blots were imaged by BioRad ChemiDoc XRS System in Chemi Hi Sensitivity mode. Band intensities were quantified using ImageJ and plotted using GraphPad Prism 6.

NIH3T3 Cell Binding Assay

NIH3T3 cells were incubated with varying concentrations of wild-type FGF1 or FGF1 BS4M1 mutant in binding buffer (20 mM Tris-HCl (pH 7.5) with 1 mM $MgCl_2$, 1 mM $MnCl_2$, 2 mM $CaCl_2$), 100 mM NaCl, and 0.1% BSA) for 3 hours at 4° C. Cells were incubated in sufficiently large volumes to avoid ligand depletion. After incubation with FGF, the cells were washed and incubated with 1:100 dilution of anti-His Hilyte Fluor 488 (Anaspec) on ice for 15 min. The cells were washed, pelleted, and resuspended in binding buffer immediately before analysis by flow cytom-etry using EMD Millipore Guava EasyCyte. Flow cytometry data were analyzed using FlowJo (v7.6.1). Binding curves were plotted and $K_d$ values were obtained using GraphPad Prism 6.

REFERENCES

1. Turner, N. & Grose, R. Fibroblast growth factor signal-ling: From development to cancer. *Nat. Rev. Cancer* 10, 116-129 (2010).
2. Behm, B., Babilas, P., Landthaler, M. & Schreml, S. Cytokines, chemokines and growth factors in wound healing. *J Eur. Acad. Dermatology Venereol.* 26, 812-820 (2012).
3. Andrae, J., Gallini, R. & Betsholtz, C. Role of platelet-derived growth factors in physiology and medicine. *Genes Dev.* 1276-1312 (2008). doi:10.1101/gad.1653708.revealing
4. Carmeliet, P. VEGF as a key mediator of angiogenesis in cancer. *Oncology* 69, 4-10 (2005).
5. Anitua, E., Sinchez, M., Orive, G. & Andia, I. Delivering growth factors for therapeutics. *Trends Pharmacol. Sci.* 29, 37-41 (2008).
6. Papo, N., Silverman, A. P., Lahti, J. L. & Cochran, J. R. Antagonistic VEGF variants engineered to simultane-ously bind to and inhibit VEGFR2 and v 3 integrin. *Proc. Natl. Acad. Sci.* 108, 14067-14072 (2011).
7. Kapur, S. et al. Engineered ligand-based VEGFR antago-nists with increased receptor binding affinity more effec-tively inhibit angiogenesis. *Bioeng. Transl. Med.* 2, 81-91 (2017).
8. Steed, D. L. Clinical evaluation of recombinant human platelet-derived growth factor for the treatment of lower extremity diabetic ulcers. *J. Vasc. surgeryl* 21, 71-78 (1995).
9. Kitamura, M. et al. Randomized Placebo-Controlled and Controlled Non-Inferiority Phase III Trials Comparing Trafermin, a Recombinant Human Fibroblast Growth Factor 2, and Enamel Matrix Derivative in Periodontal Regeneration in Intrabony Defects. *J. Bone Miner. Res.* 31, 806-814 (2016).
10. Boontheekul, T. & Mooney, D. J. Protein-based signal-ing systems in tissue engineering. *Curr. Opin. Biotechnol.* 14, 559-565 (2003).
11. Werb, Z., Vu, T. H., Rinkenberger, J. L. & Coussens, L. M. Matrix-degrading proteases and angiogenesis during development and tumor formation. *Apmis* 107, 11-18 (1999).
12. Copeland, R. a et al. The structure of human acidic fibroblast growth factor and its interaction with heparin. *Arch. Biochem. Biophys.* 289, 53-61 (1991).
13. Mignatti, P., Rifkin, D. B., Welgus, H. G. & Parks, W. C. Proteinases and tissue remodeling. in *The Molecular and Cellular Biology of Wound Repair* (ed. Clark, R. A. F.) (Springer, 1988).
14. Zakrzewska, M. et al. Increased protein stability of FGF1 can compensate for its reduced affinity for heparin. *J Biol. Chem.* 284, 25388-25403 (2009).

15. Motomura, K. et al. An FGF1:FGF2 chimeric growth factor exhibits universal FGF receptor specificity, enhanced stability and augmented activity useful for epithelial proliferation and radioprotection. *Biochim. Biophys. Acta-Gen. Subj.* 1780, 1432-1440 (2008).

16. Lee, J. & Blaber, M. Increased Functional Half-life of Fibroblast Growth Factor-1 by Recovering a Vestigial Disulfide Bond. *Proteins and Proteomics* 1, 37-42 (2010).

17. Kobielak, A. et al. Protease Resistant Variants of FGF1 with Prolonged Biological Activity. *Protein Pept. Lett.* 434-443 (2014).

18. Draghia-Akli, R. et al. Myogenic expression of an injectable protease-resistant growth hormone-releasing hormone augments long-term growth in pigs. *Nat. Biotechnol.* 17, 1179-1183 (1999).

19. Cook, a L. et al. Purification and analysis of proteinase-resistant mutants of recombinant platelet-derived growth factor-BB exhibiting improved biological activity. *Biochem. J.* 281, 57-65 (1992).

20. Gosalia, D. N., Salisbury, C. M., Ellman, J. A. & Diamond, S. L. High Throughput Substrate Specificity Profiling of Serine and Cysteine Proteases Using Solution-phase Fluorogenic Peptide Microarrays. *Mol. Cell. Proteomics* 4, 626-636 (2005).

21. Buchtova, M. et al. Instability restricts signaling of multiple fibroblast growth factors. *Cell. Mol. Life Sci.* 72, 2445-2459 (2015).

22. Boottger, R., Hoffmann, R. & Knappe, D. Differential stability of therapeutic peptides with different proteolytic cleavage sites in blood, plasma and serum. *PLoS One* 12, 1-15 (2017).

23. Romero, N., Tinker, D., Hyde, D. & Rucker, R. B. Role of plasma and serum proteases in the degradation of elastin. *Arch. Biochem. Biophys.* 244, 161-168 (1986).

24. Wagner, I. et al. Serum Proteases Potentiate BMP-Induced Cell Cycle Re-entry of Dedifferentiating Muscle Cells during Newt Limb Regeneration. *Dev. Cell* 40, 608-617 (2017).

25. Rosengart, T. K., Johnson, W. V., Friesel, R., Clark, R. & Maciag, T. Heparin protects heparin-binding growth factor-I from proteolytic inactivation in vitro. *Biochem. Biophys. Res. Commun.* 152, 432-440 (1988).

26. Cochran, J. R., Kim, Y. S., Lippow, S. M., Rao, B. & Wittrup, K. D. Improved mutants from directed evolution are biased to orthologous substitutions. *Protein Eng. Des. Sel.* 19, 245-253 (2006).

27. Jones, D. S., Tsai, P.-C. & Cochran, J. R. Engineering hepatocyte growth factor fragments with high stability and activity as Met receptor agonists and antagonists. *Proc. Natl. Acad. Sci.* 108, 13035-13040 (2011).

28. Zheng, X. et al. Proteomic analysis for the assessment of different lots of fetal bovine serum as a raw material for cell culture. Part IV. Application of proteomics to the manufacture of biological drugs. *Biotechnol. Prog.* 22, 1294-1300 (2006).

29. INAGAMI, T. & STURTEVANT, J. M. Nonspecific catalyses by alpha-chymotrypsin and trypsin. J. Biol. Chem. 235, 1019-23 (1960).

30. Lauer, G. et al. Expression and proteolysis of vascular endothelial growth factor is increased in chronic wounds. *J. Invest. Dermatol.* 115, 12-18 (2000).

31. Korc, M. & Friesel, R. E. The role of fibroblast growth factors in tumor growth. *Curr. Cancer Drug Targets* 9, 639-51 (2009).

32. Beenken, A. & Mohammadi, M. The FGF family: biology, pathophysiology and therapy. *Nat Rev Drug Discov.* 8, 235-253 (2009).

33. Mason, I. Initiation to end point: The multiple roles of fibroblast growth factors in neural development. *Nat. Rev. Neurosci.* 8, 583-596 (2007).

34. Teven, C. M., Farina, E. M., Rivas, J. & Reid, R. R. Fibroblast growth factor (FGF) signaling in development and skeletal diseases. *Genes Dis.* 1, 199-213 (2014).

35. Eswarakumar, V. P., Lax, I. & Schlessinger, J. Cellular signaling by fibroblast growth factor receptors. *Cytokine Growth Factor Rev.* 16, 139-149 (2005).

36. Knights, V. & Cook, S. J. De-regulated FGF receptors as therapeutic targets in cancer. *Pharmacol. Ther.* 125, 105-117 (2010).

37. Zhang, J. & Li, Y. Therapeutic uses of FGFs. *Semin. Cell Dev. Biol.* 53, 144-154 (2016).

38. Presta, M. et al. Fibroblast growth factor/fibroblast growth factor receptor system in angiogenesis. *Cytokine Growth Factor Rev.* 16, 159-178 (2005).

39. Carmeliet, P. Fibroblast growth factor-1 stimulates branching and survival of myocardial arteries: A goal for therapeutic angiogenesis?*Circ. Res.* 87, 176-178 (2000).

40. Schumacher, B., Pecher, P., von Specht, B. U. & Stegmann, T. Induction of neoangiogenesis in ischemic myocardium by human growth factors: first clinical results of a new treatment of coronary heart disease. *Circulation* 97, 645-650 (1998).

41. Mon, S. et al. A Dominant-Negative FGF1 Mutant (the R50E Mutant) Suppresses Tumorigenesis and Angiogenesis. *PLoS One* 8, (2013).

42. Comerota, A. J. et al. Naked plasmid DNA encoding fibroblast growth factor type 1 for the treatment of end-stage unreconstructible lower extremity ischemia: Preliminary results of a phase I trial. *J. Vasc. Surg.* 35, 930-936 (2002).

43. Nikol, S. et al. Therapeutic angiogenesis with intramuscular NV1FGF improves amputation-free survival in patients with critical limb ischemia. *Mol. Ther.* 16, 972-978 (2008).

44. Belch, J. et al. Effect of fibroblast growth factor NV1FGF on amputation and death: A randomised placebo-controlled trial of gene therapy in critical limb ischaemia. *Lancet* 377, 1929-1937 (2011).

45. Rask-Andersen, M., Zhang, J., Fabbro, D. & Schio, H. B. Advances in kinase targeting: current clinical use and clinical trials. *Trends Pharmacol. Sci* 35, 604-620 (2014).

46. Saksela, O., Moscatelli, D., Sommer, A. & Rifkin, D. B. Endothelial cell-derived heparan sulfate binds basic fibroblast growth factor and protects it from proteolytic degradation. *J Cell Biol.* 107, 743-51 (1988).

47. Whitelock, J. M., Murdoch, A. D., Iozzo, R. V. & Underwood, P. A. The degradation of human endothelial cell-derived perlecan and release of bound basic fibroblast growth factor by stromelysin, collagenase, plasmin, and heparanases. *J Biol. Chem.* 271, 10079-10086 (1996).

48. Park, S. et al. Limitations of yeast surface display in engineering proteins of high thermostability. *Protein Eng. Des. Sel.* 19, 211-217 (2006).

49. Kowalski, J. M., Parekh, R. N. & Wittrup, K. D. Secretion Efficiency in *Saccharomyces* cere V isiae of Bovine Pancreatic Trypsin Inhibitor Mutants Lacking Disulfide Bonds Is Correlated with Thermodynamic Stability. *Biochemistry* 37, 1264-1273 (1998).

50. Lee, J., Dubey, V. K., Longo, L. M. & Blaber, M. A Logical OR Redundancy within the Asx-Pro-Asx-Gly Type I??-Turn Motif. *J Mol. Biol.* 377, 1251-1264 (2008).

51. Dubey, V. K., Lee, J., Somasundaram, T., Blaber, S. & Blaber, M. Spackling the Crack: Stabilizing Human Fibroblast Growth Factor-1 by Targeting the N and C terminus (3-Strand Interactions. *J. Mol. Biol.* 371, 256-268 (2007).

52. Chao, G. et al. Isolating and engineering human antibodies using yeast surface display. *Nat. Protoc.* 1, 755-768 (2006).

53. Deventer, J. A. Van & Wittrup, K. D. Yeast surface display for antibody isolation: Library construction, library screening, and affinity maturation. *Methods Mol. Biol.* 1131, 151-181 (2014).

54. Lavinder, J. J., Hari, S. B., Sullivan, B. J. & Magliery, T. J. High-throughput thermal scanning: a general, rapid dye-binding thermal shift screen for protein engineering. *J Am Chem Soc.* 131, 3794-3795 (2009).

55. Ericsson, U. B., Hallberg, B. M., Detitta, G. T., Dekker, N. & Nordlund, P. Thermofluor-based high-throughput stability optimization of proteins for structural studies. *Anal. Biochem.* 357, 289-298 (2006).

56. Yun, Y. et al. Fibroblast Growth Factors: Biology, Function, and Application for Tissue Regeneration. *J. Tissue Eng.* (2010). doi:10.4061/2010/218142

57. Sharrocks, A. D. Cell Cycle: Sustained ERK Signalling Represses the Inhibitors. 16, 540-542

58. Hervio, L. S. et al. Negative selectivity and the evolution of protease cascades: the specificity of plasmin for peptide and protein substrates. *Chem. Biol.* 7, 443-453 (2000).

59. Breitling, J. & Aebi, M. N-Linked Protein Glycosylation in the Endoplasmic Reticulum. *Cold Spring Harb. Perspect. Biol.* (2013). doi:10.1101/cshperspect.a013359

60. Yamaji, S. et al. A Novel Fibroblast Growth Factor-1 (FGF1) Mutant that Acts as an FGF Antagonist. *PLoS One* 5, (2010).

61. Weber, J. D., Raben, D. M., Phillips, P. J. & Baldassare, J. J. Sustained activation of extracellular-signal-regulated kinase 1 (ERK1) is required for the continued expression of cyclin D1 in G 1 phase. *Biochem. J.* 68, 61-68 (1997).

62. Ho, S. N., Hunt, H. D., Horton, R. M., Pullen, J. K. & Peasea, L. R. Site-directed mutagenesis by overlap extension using the polymerase chain reaction. *Gene* 77, 51-59 (1989).

What is claimed is:

1. A variant of human fibroblast growth factor 1 (FGF1) of SEQ ID NO:1 comprising the amino acid substitution L131R, wherein the resulting FGF1 variant exhibits increased proteolytic stability as compared to wild-type FGF1 of SEQ ID NO:1, wherein said FGF1 variant is a fibroblast growth factor receptor (FGFR) antagonist.

2. The variant according to claim 1, wherein said FGF1 variant further comprises at least one amino acid substitution selected from the group consisting of D28N, Q40P, S47I, and H93G.

3. The variant according to claim 1, wherein said variant further comprises amino acid substitution D28N.

4. The variant according to claim 1, wherein said FGF1 variant further comprises amino acid substitutions Q40P, S47I, and H93G.

5. The variant according to claim 1, wherein said FGF1 variant further comprises amino acid substitutions D28N, Q40P, S47I, and H93G.

6. The variant according to claim 1, wherein said FGF1 variant is conjugated to a member selected from a detectable moiety, a water-soluble polymer, a water-insoluble polymer, a therapeutic moiety, a targeting moiety and a combination thereof.

7. The variant according to claim 6, wherein said FGF1 variant is conjugated to a detectable moiety selected from a radioisotope, a paramagnet, a fluorophore and combinations thereof.

8. The variant according to claim 6, wherein said FGF1 variant is conjugated to a detectable moiety to form a diagnostic imaging agent.

9. A pharmaceutical formulation comprising a FGF1 variant according to claim 1, wherein said variant is in combination with a pharmaceutically acceptable carrier.

\* \* \* \* \*